US009181311B2

(12) United States Patent
Spencer et al.

(10) Patent No.: US 9,181,311 B2
(45) Date of Patent: Nov. 10, 2015

(54) MYCOBACTERIAL VACCINES

(75) Inventors: Alexandra Jane Spencer, Oxford (GB); Matthew Guy Cottingham, Oxford (GB); Adrian Vivian Sinton Hill, Oxford (GB); Fergal Hill, Lyons (FR)

(73) Assignees: Isis Innovation Limited (GB); Imaxio SA (FR)

( * ) Notice: Subject to any disclaimer, the term of this patent is extended or adjusted under 35 U.S.C. 154(b) by 327 days.

(21) Appl. No.: 13/501,756

(22) PCT Filed: Oct. 15, 2010

(86) PCT No.: PCT/GB2010/051741
§ 371 (c)(1),
(2), (4) Date: Jul. 26, 2012

(87) PCT Pub. No.: WO2011/045612
PCT Pub. Date: Apr. 21, 2011

(65) Prior Publication Data

US 2012/0282290 A1 Nov. 8, 2012

(30) Foreign Application Priority Data

Oct. 16, 2009 (GB) .................................. 0918154.6

(51) Int. Cl.

| | |
|---|---|
| ***A61K 39/04*** | (2006.01) |
| ***A61K 39/02*** | (2006.01) |
| ***A61K 39/00*** | (2006.01) |
| ***C07K 14/435*** | (2006.01) |
| ***C07K 16/12*** | (2006.01) |
| ***C12N 15/62*** | (2006.01) |

(52) U.S. Cl.
CPC ............... *C07K 14/435* (2013.01); *A61K 39/04* (2013.01); *C07K 16/1289* (2013.01); *C12N 15/62* (2013.01)

(58) Field of Classification Search
CPC ....... A61K 39/00; A61K 39/02; A61K 39/04; C07H 21/04; C07K 2/00; C07K 7/00; C07K 14/00
USPC ................. 424/9.1, 9.2, 184.1, 185.1, 190.2, 424/192.1, 234.1, 248.1; 536/23.7, 23.1
See application file for complete search history.

(56) References Cited

U.S. PATENT DOCUMENTS 7,951,376 B2 * 5/2011 Hill et al. .................. 424/184.1

FOREIGN PATENT DOCUMENTS

| | | | |
|---|---|---|---|
| EP | 1795540 | A1 | 6/2007 |
| JP | 2007-528210 | A | 10/2007 |
| WO | 91/11461 | | 8/1991 |
| WO | 2005/014654 | A2 | 2/2005 |
| WO | 2008/122817 | A2 | 10/2008 |

OTHER PUBLICATIONS

International Search Report issued from corresponding PCTGB2010/051741, dated Dec. 3, 2010.

Abbink, Peter, et al., "Comparative Seroprevalence and Immunogenicity of Six Rare Serotype Recombinant Adenovirus Vaccine Vectors for Subgroups B and D," Journal of Virology, May 2007, pp. 4654-4663, vol. 81, No. 9, American Society for Microbiology.

Farina, Steven F., et al., "Replication-Defective Vector Based on a Chimpanzee Adenovirus," Journal of Virology, Dec. 2001, pp. 11603-11613. vol. 75, No. 23, American Society of Microbiology.

Geiser, Martin, et al., "Integration of PCR Fragments at Any Specific Site within Cloning Vectors without the Use of Restriction Enzymes and DNA Ligase," BioTechniques, Jul. 2001, pp. 88-92, vol. 31, No. 1, Novartis Pharma, Basel, Switzerland.

Henikoff, Steven, et al., "Amino Acid Substitution Matrices from Protein Blocks," Proc. Natl. Acad. Sci., Nov. 1992, pp. 10915-10919, vol. 89, Biochemistry, USA.

Lemckert, Angelique, et al., "Immunogenicity of Heterologous Prime-Boost Regimens Involving Recombinant Adenovirus Serotype 11 (Ad11) and Ad35 Vaccine Vectors in the Presence of Anti-Ad5 Immunity," Journal of Virology, Jul. 2005, pp. 9694-9701, vol. 79. No. 15, American Society for Microbiology.

McShane, Helen, et al., "Recombinant Modified Vaccinia Virus Ankara expressing antigen 85A boosts BCG-primed and naturally acquired antimycobacterial immunity in humans," Nature Medicne, Nov. 2004; pp. 1240-1244, vol. 10, No. 11.

Ogun, Solabomi A., "The Oligomerization Domain of C4-Binding Protein (C4bp) Acts as an Adjuvant, and the Fusion Protein Comprised of the 19-Kilodalton Merozoite Surface Protein 1 Fused with the Murine C4bp Domain Protects Mice against Malaria," Infection and Immunity, Aug. 2008, pp. 3817-3823, vol. 76, No. 8 American Society for Microbiology.

Puigbo, Pere, et al., "Optimizer: a web server for optimizing the codon usage of DNA sequences," Nucleic Acids Research, Mar. 28, 2007, pp. W126-W131, vol. 35.

Reyes-Sandoval, Arturo, et al.,"Prime-Boost Immunization with Adenoviral and Modified Vaccinia Virus Ankara Vectors Enhances the Durability and Polyfunctionality of Protective Malaria CD8 T-Cell Responses," Infection and Immunity, Jan. 2010, pp. 145-153, vol. 78, No. 1, American Society for Microbiology.

Roy, Soumitra, et al., "Characterization of a Family of Chiampanzee Adenoviruses and Development of Molecular Clones for Gene Transfer Vectors," Human Gene Therapy, 2004, pp. 519-530, vol. 15, No. 5, Mary Ann Liebert, Inc.

(Continued)

*Primary Examiner* — Rodeny P Swartz
(74) *Attorney, Agent, or Firm* — Banner & Witcoff, Ltd.

(57) ABSTRACT

There is provided a fusion protein or a polynucleotide sequence encoding said fusion protein that comprises first and second domains, wherein the first domain of the fusion protein comprises an amino acid sequence having at least 70% sequence identity to the amino acid sequence of SEQ ID NO: 1, or a fragment thereof comprising at least 20 consecutive amino acids thereof; and wherein the second domain of the fusion protein comprises a mycobacterial antigen or an antigenic fragment thereof. Also provided are corresponding therapeutic uses thereof for the protection of primates against mycobacterial infections.

15 Claims, 7 Drawing Sheets

(56) References Cited

OTHER PUBLICATIONS

Figure 1:
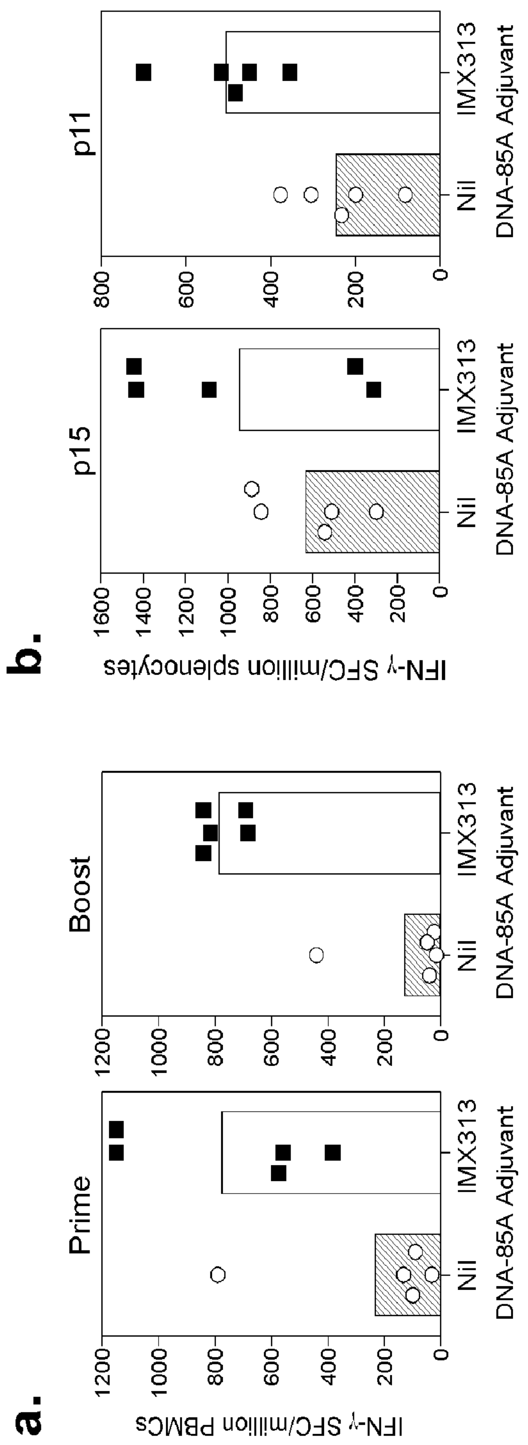

Sridhar, S., et al.,"Single-Dose Protection against Plasmodium berghei by a Simian Adenovirus Vector Using a Human Cytomegalovirus Promoter Containing Intron A," Journal of Virology, Apr. 2008, pp. 3811-3833, vol. 82, No. 8, American Society for Microbiology.

Taracha, Evans L. N., et al., "Heterologous Priming-Boosting Immunization of Cattle with Mycobacterium tuberculosis 85A Induces Antigen-Specific T-Cell Responses" Infection and Immunity, Dec. 2003, pp. 6906-6914, vol. 71, No. 12, American Society for Microbiology.

Jan. 30, 2015 (JP) Notification of Reason for Rejection—App. No. 2012-533696.

* cited by examiner a.
b.
c.
d.
p15
p11
IFN-γ SFC/million splenocytes
Nil
MVA-85A
IMX313 Adjuvant
Prime
Boost
% IFN-γ+ CD4+ cells
% IFN-γ+ CD8+ cells a.
3+
2+
1+
MVA-85a
MVA-85a 313
b.
% CD4+ cells
0.12
0.09
0.06
0.03
0
MVA-85a
MVA-85a 313
IFN-g
IL-2
TNF-a
(Pies)
c.
MVA-85a
MVA-85a 313
d.
% CD8+ cells
0.06
0.04
0.02
0
MVA-85a
MVA-85a 313
IFN-g
IL-2
TNF-a
(Pies)

SEQUENCE LISTING

```
<160> NUMBER OF SEQ ID NOS: 60

<210> SEQ ID NO 1
<211> LENGTH: 55
<212> TYPE: PRT
<213> ORGANISM: Artificial Sequence
<220> FEATURE:
<223> OTHER INFORMATION: Synthetic Sequence

<400> SEQUENCE: 1

Lys Lys Gln Gly Asp Ala Asp Val Cys Gly Glu Val Ala Tyr Ile Gln
1               5                   10                  15

Ser Val Val Ser Asp Cys His Val Pro Thr Ala Glu Leu Arg Thr Leu
            20                  25                  30

Leu Glu Ile Arg Lys Leu Phe Leu Glu Ile Gln Lys Leu Lys Val Glu
        35                  40                  45

Leu Gln Gly Leu Ser Lys Glu
    50                  55


<210> SEQ ID NO 2
<211> LENGTH: 171
<212> TYPE: DNA
<213> ORGANISM: Artificial Sequence
<220> FEATURE:
<223> OTHER INFORMATION: Synthetic sequence

<400> SEQUENCE: 2

aagaagcaag gtgatgctga tgtgtgcgga gaggttgctt atattcagag cgtcgtctcc      60

gattgccacg tgcctacagc ggaactgcgt actctgctgg aaatacgaaa actcttcctg     120

gagattcaaa aactgaaggt ggaattgcaa ggactgagca aggagtaata a              171


<210> SEQ ID NO 3
<211> LENGTH: 338
<212> TYPE: PRT
<213> ORGANISM: Mycobacterium tuberculosis

<400> SEQUENCE: 3

Met Gln Leu Val Asp Arg Val Arg Gly Ala Val Thr Gly Met Ser Arg
1               5                   10                  15

Arg Leu Val Val Gly Ala Val Gly Ala Ala Leu Val Ser Gly Leu Val
            20                  25                  30

Gly Ala Val Gly Gly Thr Ala Thr Ala Gly Ala Phe Ser Arg Pro Gly
        35                  40                  45
```

```
Leu Pro Val Glu Tyr Leu Gln Val Pro Ser Pro Ser Met Gly Arg Asp
    50                  55                  60

Ile Lys Val Gln Phe Gln Ser Gly Gly Ala Asn Ser Pro Ala Leu Tyr
65                  70                  75                  80

Leu Leu Asp Gly Leu Arg Ala Gln Asp Asp Phe Ser Gly Trp Asp Ile
                85                  90                  95

Asn Thr Pro Ala Phe Glu Trp Tyr Asp Gln Ser Gly Leu Ser Val Val
            100                 105                 110

Met Pro Val Gly Gly Gln Ser Ser Phe Tyr Ser Asp Trp Tyr Gln Pro
        115                 120                 125

Ala Cys Gly Lys Ala Gly Cys Gln Thr Tyr Lys Trp Glu Thr Phe Leu
    130                 135                 140

Thr Ser Glu Leu Pro Gly Trp Leu Gln Ala Asn Arg His Val Lys Pro
145                 150                 155                 160

Thr Gly Ser Ala Val Val Gly Leu Ser Met Ala Ala Ser Ser Ala Leu
                165                 170                 175

Thr Leu Ala Ile Tyr His Pro Gln Gln Phe Val Tyr Ala Gly Ala Met
            180                 185                 190

Ser Gly Leu Leu Asp Pro Ser Gln Ala Met Gly Pro Thr Leu Ile Gly
        195                 200                 205

Leu Ala Met Gly Asp Ala Gly Gly Tyr Lys Ala Ser Asp Met Trp Gly
    210                 215                 220

Pro Lys Glu Asp Pro Ala Trp Gln Arg Asn Asp Pro Leu Leu Asn Val
225                 230                 235                 240

Gly Lys Leu Ile Ala Asn Asn Thr Arg Val Trp Val Tyr Cys Gly Asn
                245                 250                 255

Gly Lys Pro Ser Asp Leu Gly Gly Asn Asn Leu Pro Ala Lys Phe Leu
            260                 265                 270

Glu Gly Phe Val Arg Thr Ser Asn Ile Lys Phe Gln Asp Ala Tyr Asn
        275                 280                 285

Ala Gly Gly Gly His Asn Gly Val Phe Asp Phe Pro Asp Ser Gly Thr
    290                 295                 300

His Ser Trp Glu Tyr Trp Gly Ala Gln Leu Asn Ala Met Lys Pro Asp
305                 310                 315                 320

Leu Gln Arg Ala Leu Gly Ala Thr Pro Asn Thr Gly Pro Ala Pro Gln
                325                 330                 335

Gly Ala


<210> SEQ ID NO 4
<211> LENGTH: 325
<212> TYPE: PRT
<213> ORGANISM: Mycobacterium tuberculosis

<400> SEQUENCE: 4

Met Thr Asp Val Ser Arg Lys Ile Arg Ala Trp Gly Arg Arg Leu Met
1               5                   10                  15

Ile Gly Thr Ala Ala Ala Val Val Leu Pro Gly Leu Val Gly Leu Ala
            20                  25                  30

Gly Gly Ala Ala Thr Ala Gly Ala Phe Ser Arg Pro Gly Leu Pro Val
        35                  40                  45

Glu Tyr Leu Gln Val Pro Ser Pro Ser Met Gly Arg Asp Ile Lys Val
    50                  55                  60

Gln Phe Gln Ser Gly Gly Asn Asn Ser Pro Ala Val Tyr Leu Leu Asp
65                  70                  75                  80
```

```
Gly Leu Arg Ala Gln Asp Asp Tyr Asn Gly Trp Asp Ile Asn Thr Pro
                85                  90                  95

Ala Phe Glu Trp Tyr Tyr Gln Ser Gly Leu Ser Ile Val Met Pro Val
            100                 105                 110

Gly Gly Gln Ser Ser Phe Tyr Ser Asp Trp Tyr Ser Pro Ala Cys Gly
        115                 120                 125

Lys Ala Gly Cys Gln Thr Tyr Lys Trp Glu Thr Phe Leu Thr Ser Glu
    130                 135                 140

Leu Pro Gln Trp Leu Ser Ala Asn Arg Ala Val Lys Pro Thr Gly Ser
145                 150                 155                 160

Ala Ala Ile Gly Leu Ser Met Ala Gly Ser Ser Ala Met Ile Leu Ala
                165                 170                 175

Ala Tyr His Pro Gln Gln Phe Ile Tyr Ala Gly Ser Leu Ser Ala Leu
            180                 185                 190

Leu Asp Pro Ser Gln Gly Met Gly Pro Ser Leu Ile Gly Leu Ala Met
        195                 200                 205

Gly Asp Ala Gly Gly Tyr Lys Ala Ala Asp Met Trp Gly Pro Ser Ser
    210                 215                 220

Asp Pro Ala Trp Glu Arg Asn Asp Pro Thr Gln Gln Ile Pro Lys Leu
225                 230                 235                 240

Val Ala Asn Asn Thr Arg Leu Trp Val Tyr Cys Gly Asn Gly Thr Pro
                245                 250                 255

Asn Glu Leu Gly Gly Ala Asn Ile Pro Ala Glu Phe Leu Glu Asn Phe
            260                 265                 270

Val Arg Ser Ser Asn Leu Lys Phe Gln Asp Ala Tyr Asn Ala Ala Gly
        275                 280                 285

Gly His Asn Ala Val Phe Asn Phe Pro Pro Asn Gly Thr His Ser Trp
    290                 295                 300

Glu Tyr Trp Gly Ala Gln Leu Asn Ala Met Lys Gly Asp Leu Gln Ser
305                 310                 315                 320

Ser Leu Gly Ala Gly
                325


<210> SEQ ID NO 5
<211> LENGTH: 340
<212> TYPE: PRT
<213> ORGANISM: Mycobacterium tuberculosis

<400> SEQUENCE: 5

Met Thr Phe Phe Glu Gln Val Arg Arg Leu Arg Ser Ala Ala Thr Thr
1               5                   10                  15

Leu Pro Arg Arg Leu Ala Ile Ala Ala Met Gly Ala Val Leu Val Tyr
            20                  25                  30

Gly Leu Val Gly Thr Phe Gly Gly Pro Ala Thr Ala Gly Ala Phe Ser
        35                  40                  45

Arg Pro Gly Leu Pro Val Glu Tyr Leu Gln Val Pro Ser Ala Ser Met
    50                  55                  60

Gly Arg Asp Ile Lys Val Gln Phe Gln Gly Gly Gly Pro His Ala Val
65                  70                  75                  80

Tyr Leu Leu Asp Gly Leu Arg Ala Gln Asp Asp Tyr Asn Gly Trp Asp
                85                  90                  95

Ile Asn Thr Pro Ala Phe Glu Glu Tyr Tyr Gln Ser Gly Leu Ser Val
            100                 105                 110

Ile Met Pro Val Gly Gly Gln Ser Ser Phe Tyr Thr Asp Trp Tyr Gln
        115                 120                 125
```

```
Pro Ser Gln Ser Asn Gly Gln Asn Tyr Thr Tyr Lys Trp Glu Thr Phe
    130                 135                 140

Leu Thr Arg Glu Met Pro Ala Trp Leu Gln Ala Asn Lys Gly Val Ser
145                 150                 155                 160

Pro Thr Gly Asn Ala Ala Val Gly Leu Ser Met Ser Gly Gly Ser Ala
                165                 170                 175

Leu Ile Leu Ala Ala Tyr Tyr Pro Gln Gln Phe Pro Tyr Ala Ala Ser
            180                 185                 190

Leu Ser Gly Phe Leu Asn Pro Ser Glu Gly Trp Trp Pro Thr Leu Ile
        195                 200                 205

Gly Leu Ala Met Asn Asp Ser Gly Gly Tyr Asn Ala Asn Ser Met Trp
    210                 215                 220

Gly Pro Ser Ser Asp Pro Ala Trp Lys Arg Asn Asp Pro Met Val Gln
225                 230                 235                 240

Ile Pro Arg Leu Val Ala Asn Asn Thr Arg Ile Trp Val Tyr Cys Gly
                245                 250                 255

Asn Gly Thr Pro Ser Asp Leu Gly Gly Asp Asn Ile Pro Ala Lys Phe
            260                 265                 270

Leu Glu Gly Leu Thr Leu Arg Thr Asn Gln Thr Phe Arg Asp Thr Tyr
        275                 280                 285

Ala Ala Asp Gly Gly Arg Asn Gly Val Phe Asn Phe Pro Pro Asn Gly
    290                 295                 300

Thr His Ser Trp Pro Tyr Trp Asn Glu Gln Leu Val Ala Met Lys Ala
305                 310                 315                 320

Asp Ile Gln His Val Leu Asn Gly Ala Thr Pro Pro Ala Ala Pro Ala
                325                 330                 335

Ala Pro Ala Ala
            340


<210> SEQ ID NO 6
<211> LENGTH: 95
<212> TYPE: PRT
<213> ORGANISM: Mycobacterium tuberculosis

<400> SEQUENCE: 6

Met Thr Glu Gln Gln Trp Asn Phe Ala Gly Ile Glu Ala Ala Ala Ser
1               5                   10                  15

Ala Ile Gln Gly Asn Val Thr Ser Ile His Ser Leu Leu Asp Glu Gly
            20                  25                  30

Lys Gln Ser Leu Thr Lys Leu Ala Ala Ala Trp Gly Gly Ser Gly Ser
        35                  40                  45

Glu Ala Tyr Gln Gly Val Gln Gln Lys Trp Asp Ala Thr Ala Thr Glu
    50                  55                  60

Leu Asn Asn Ala Leu Gln Asn Leu Ala Arg Thr Ile Ser Glu Ala Gly
65                  70                  75                  80

Gln Ala Met Ala Ser Thr Glu Gly Asn Val Thr Gly Met Phe Ala
                85                  90                  95


<210> SEQ ID NO 7
<211> LENGTH: 96
<212> TYPE: PRT
<213> ORGANISM: Mycobacterium tuberculosis

<400> SEQUENCE: 7

Met Ser Gln Ile Met Tyr Asn Tyr Pro Ala Met Leu Gly His Ala Gly
1               5                   10                  15
```

```
Asp Met Ala Gly Tyr Ala Gly Thr Leu Gln Ser Leu Gly Ala Glu Ile
            20                  25                  30

Ala Val Glu Gln Ala Ala Leu Gln Ser Ala Trp Gln Gly Asp Thr Gly
        35                  40                  45

Ile Thr Tyr Gln Ala Trp Gln Ala Gln Trp Asn Gln Ala Met Glu Asp
    50                  55                  60

Leu Val Arg Ala Tyr His Ala Met Ser Ser Thr His Glu Ala Asn Thr
65                  70                  75                  80

Met Ala Met Met Ala Arg Asp Thr Ala Glu Ala Ala Lys Trp Gly Gly
                85                  90                  95


<210> SEQ ID NO 8
<211> LENGTH: 355
<212> TYPE: PRT
<213> ORGANISM: Mycobacterium tuberculosis

<400> SEQUENCE: 8

Met Ser Asn Ser Arg Arg Arg Ser Leu Arg Trp Ser Trp Leu Leu Ser
1               5                   10                  15

Val Leu Ala Ala Val Gly Leu Gly Leu Ala Thr Ala Pro Ala Gln Ala
            20                  25                  30

Ala Pro Pro Ala Leu Ser Gln Asp Arg Phe Ala Asp Phe Pro Ala Leu
        35                  40                  45

Pro Leu Asp Pro Ser Ala Met Val Ala Gln Val Gly Pro Gln Val Val
    50                  55                  60

Asn Ile Asn Thr Lys Leu Gly Tyr Asn Asn Ala Val Gly Ala Gly Thr
65                  70                  75                  80

Gly Ile Val Ile Asp Pro Asn Gly Val Val Leu Thr Asn Asn His Val
                85                  90                  95

Ile Ala Gly Ala Thr Asp Ile Asn Ala Phe Ser Val Gly Ser Gly Gln
            100                 105                 110

Thr Tyr Gly Val Asp Val Val Gly Tyr Asp Arg Thr Gln Asp Val Ala
        115                 120                 125

Val Leu Gln Leu Arg Gly Ala Gly Gly Leu Pro Ser Ala Ala Ile Gly
    130                 135                 140

Gly Gly Val Ala Val Gly Glu Pro Val Val Ala Met Gly Asn Ser Gly
145                 150                 155                 160

Gly Gln Gly Gly Thr Pro Arg Ala Val Pro Gly Arg Val Val Ala Leu
                165                 170                 175

Gly Gln Thr Val Gln Ala Ser Asp Ser Leu Thr Gly Ala Glu Glu Thr
            180                 185                 190

Leu Asn Gly Leu Ile Gln Phe Asp Ala Ala Ile Gln Pro Gly Asp Ser
        195                 200                 205

Gly Gly Pro Val Val Asn Gly Leu Gly Gln Val Val Gly Met Asn Thr
    210                 215                 220

Ala Ala Ser Asp Asn Phe Gln Leu Ser Gln Gly Gly Gln Gly Phe Ala
225                 230                 235                 240

Ile Pro Ile Gly Gln Ala Met Ala Ile Ala Gly Gln Ile Arg Ser Gly
                245                 250                 255

Gly Gly Ser Pro Thr Val His Ile Gly Pro Thr Ala Phe Leu Gly Leu
            260                 265                 270

Gly Val Val Asp Asn Asn Gly Asn Gly Ala Arg Val Gln Arg Val Val
        275                 280                 285

Gly Ser Ala Pro Ala Ala Ser Leu Gly Ile Ser Thr Gly Asp Val Ile
```

```
    290                 295                 300

Thr Ala Val Asp Gly Ala Pro Ile Asn Ser Ala Thr Ala Met Ala Asp
305                 310                 315                 320

Ala Leu Asn Gly His His Pro Gly Asp Val Ile Ser Val Thr Trp Gln
                325                 330                 335

Thr Lys Ser Gly Gly Thr Arg Thr Gly Asn Val Thr Leu Ala Glu Gly
            340                 345                 350

Pro Pro Ala
        355


<210> SEQ ID NO 9
<211> LENGTH: 391
<212> TYPE: PRT
<213> ORGANISM: Mycobacterium tuberculosis

<400> SEQUENCE: 9

Met Val Asp Phe Gly Ala Leu Pro Pro Glu Ile Asn Ser Ala Arg Met
1               5                   10                  15

Tyr Ala Gly Pro Gly Ser Ala Ser Leu Val Ala Ala Ala Gln Met Trp
            20                  25                  30

Asp Ser Val Ala Ser Asp Leu Phe Ser Ala Ala Ser Ala Phe Gln Ser
        35                  40                  45

Val Val Trp Gly Leu Thr Val Gly Ser Trp Ile Gly Ser Ser Ala Gly
    50                  55                  60

Leu Met Val Ala Ala Ala Ser Pro Tyr Val Ala Trp Met Ser Val Thr
65                  70                  75                  80

Ala Gly Gln Ala Glu Leu Thr Ala Ala Gln Val Arg Val Ala Ala Ala
                85                  90                  95

Ala Tyr Glu Thr Ala Tyr Gly Leu Thr Val Pro Pro Pro Val Ile Ala
            100                 105                 110

Glu Asn Arg Ala Glu Leu Met Ile Leu Ile Ala Thr Asn Leu Leu Gly
        115                 120                 125

Gln Asn Thr Pro Ala Ile Ala Val Asn Glu Ala Glu Tyr Gly Glu Met
    130                 135                 140

Trp Ala Gln Asp Ala Ala Ala Met Phe Gly Tyr Ala Ala Ala Thr Ala
145                 150                 155                 160

Thr Ala Thr Ala Thr Leu Leu Pro Phe Glu Glu Ala Pro Glu Met Thr
                165                 170                 175

Ser Ala Gly Gly Leu Leu Glu Gln Ala Ala Ala Val Glu Glu Ala Ser
            180                 185                 190

Asp Thr Ala Ala Ala Asn Gln Leu Met Asn Asn Val Pro Gln Ala Leu
        195                 200                 205

Gln Gln Leu Ala Gln Pro Thr Gln Gly Thr Thr Pro Ser Ser Lys Leu
    210                 215                 220

Gly Gly Leu Trp Lys Thr Val Ser Pro His Arg Ser Pro Ile Ser Asn
225                 230                 235                 240

Met Val Ser Met Ala Asn Asn His Met Ser Met Thr Asn Ser Gly Val
                245                 250                 255

Ser Met Thr Asn Thr Leu Ser Ser Met Leu Lys Gly Phe Ala Pro Ala
            260                 265                 270

Ala Ala Ala Gln Ala Val Gln Thr Ala Ala Gln Asn Gly Val Arg Ala
        275                 280                 285

Met Ser Ser Leu Gly Ser Ser Leu Gly Ser Ser Gly Leu Gly Gly Gly
    290                 295                 300
```

```
Val Ala Ala Asn Leu Gly Arg Ala Ala Ser Val Gly Ser Leu Ser Val
305                 310                 315                 320

Pro Gln Ala Trp Ala Ala Ala Asn Gln Ala Val Thr Pro Ala Ala Arg
                325                 330                 335

Ala Leu Pro Leu Thr Ser Leu Thr Ser Ala Ala Glu Arg Gly Pro Gly
            340                 345                 350

Gln Met Leu Gly Gly Leu Pro Val Gly Gln Met Gly Ala Arg Ala Gly
        355                 360                 365

Gly Gly Leu Ser Gly Val Leu Arg Val Pro Pro Arg Pro Tyr Val Met
    370                 375                 380

Pro His Ser Pro Ala Ala Gly
385                 390


<210> SEQ ID NO 10
<211> LENGTH: 236
<212> TYPE: PRT
<213> ORGANISM: Mycobacterium tuberculosis

<400> SEQUENCE: 10

Met Arg Thr Pro Arg Arg His Cys Arg Arg Ile Ala Val Leu Ala Ala
1               5                   10                  15

Val Ser Ile Ala Ala Thr Val Val Ala Gly Cys Ser Ser Gly Ser Lys
            20                  25                  30

Pro Ser Gly Gly Pro Leu Pro Asp Ala Lys Pro Leu Val Glu Glu Ala
        35                  40                  45

Thr Ala Gln Thr Lys Ala Leu Lys Ser Ala His Met Val Leu Thr Val
    50                  55                  60

Asn Gly Lys Ile Pro Gly Leu Ser Leu Lys Thr Leu Ser Gly Asp Leu
65                  70                  75                  80

Thr Thr Asn Pro Thr Ala Ala Thr Gly Asn Val Lys Leu Thr Leu Gly
                85                  90                  95

Gly Ser Asp Ile Asp Ala Asp Phe Val Val Phe Asp Gly Ile Leu Tyr
            100                 105                 110

Ala Thr Leu Thr Pro Asn Gln Trp Ser Asp Phe Gly Pro Ala Ala Asp
        115                 120                 125

Ile Tyr Asp Pro Ala Gln Val Leu Asn Pro Asp Thr Gly Leu Ala Asn
    130                 135                 140

Val Leu Ala Asn Phe Ala Asp Ala Lys Ala Glu Gly Arg Asp Thr Ile
145                 150                 155                 160

Asn Gly Gln Asn Thr Ile Arg Ile Ser Gly Lys Val Ser Ala Gln Ala
                165                 170                 175

Val Asn Gln Ile Ala Pro Pro Phe Asn Ala Thr Gln Pro Val Pro Ala
            180                 185                 190

Thr Val Trp Ile Gln Glu Thr Gly Asp His Gln Leu Ala Gln Ala Gln
        195                 200                 205

Leu Asp Arg Gly Ser Gly Asn Ser Val Gln Met Thr Leu Ser Lys Trp
    210                 215                 220

Gly Glu Lys Val Gln Val Thr Lys Pro Pro Val Ser
225                 230                 235


<210> SEQ ID NO 11
<211> LENGTH: 540
<212> TYPE: PRT
<213> ORGANISM: Mycobacterium tuberculosis

<400> SEQUENCE: 11
```

-continued

```
Met Ala Lys Thr Ile Ala Tyr Asp Glu Glu Ala Arg Arg Gly Leu Glu
1               5                   10                  15

Arg Gly Leu Asn Ala Leu Ala Asp Ala Val Lys Val Thr Leu Gly Pro
            20                  25                  30

Lys Gly Arg Asn Val Val Leu Glu Lys Lys Trp Gly Ala Pro Thr Ile
        35                  40                  45

Thr Asn Asp Gly Val Ser Ile Ala Lys Glu Ile Glu Leu Glu Asp Pro
    50                  55                  60

Tyr Glu Lys Ile Gly Ala Glu Leu Val Lys Glu Val Ala Lys Lys Thr
65                  70                  75                  80

Asp Asp Val Ala Gly Asp Gly Thr Thr Thr Ala Thr Val Leu Ala Gln
                85                  90                  95

Ala Leu Val Arg Glu Gly Leu Arg Asn Val Ala Ala Gly Ala Asn Pro
            100                 105                 110

Leu Gly Leu Lys Arg Gly Ile Glu Lys Ala Val Glu Lys Val Thr Glu
        115                 120                 125

Thr Leu Leu Lys Gly Ala Lys Glu Val Glu Thr Lys Glu Gln Ile Ala
    130                 135                 140

Ala Thr Ala Ala Ile Ser Ala Gly Asp Gln Ser Ile Gly Asp Leu Ile
145                 150                 155                 160

Ala Glu Ala Met Asp Lys Val Gly Asn Glu Gly Val Ile Thr Val Glu
                165                 170                 175

Glu Ser Asn Thr Phe Gly Leu Gln Leu Glu Leu Thr Glu Gly Met Arg
            180                 185                 190

Phe Asp Lys Gly Tyr Ile Ser Gly Tyr Phe Val Thr Asp Pro Glu Arg
        195                 200                 205

Gln Glu Ala Val Leu Glu Asp Pro Tyr Ile Leu Leu Val Ser Ser Lys
    210                 215                 220

Val Ser Thr Val Lys Asp Leu Leu Pro Leu Leu Glu Lys Val Ile Gly
225                 230                 235                 240

Ala Gly Lys Pro Leu Leu Ile Ile Ala Glu Asp Val Glu Gly Glu Ala
                245                 250                 255

Leu Ser Thr Leu Val Val Asn Lys Ile Arg Gly Thr Phe Lys Ser Val
            260                 265                 270

Ala Val Lys Ala Pro Gly Phe Gly Asp Arg Arg Lys Ala Met Leu Gln
        275                 280                 285

Asp Met Ala Ile Leu Thr Gly Gly Gln Val Ile Ser Glu Glu Val Gly
    290                 295                 300

Leu Thr Leu Glu Asn Ala Asp Leu Ser Leu Leu Gly Lys Ala Arg Lys
305                 310                 315                 320

Val Val Val Thr Lys Asp Glu Thr Thr Ile Val Glu Gly Ala Gly Asp
                325                 330                 335

Thr Asp Ala Ile Ala Gly Arg Val Ala Gln Ile Arg Gln Glu Ile Glu
            340                 345                 350

Asn Ser Asp Ser Asp Tyr Asp Arg Glu Lys Leu Gln Glu Arg Leu Ala
        355                 360                 365

Lys Leu Ala Gly Gly Val Ala Val Ile Lys Ala Gly Ala Ala Thr Glu
    370                 375                 380

Val Glu Leu Lys Glu Arg Lys His Arg Ile Glu Asp Ala Val Arg Asn
385                 390                 395                 400

Ala Lys Ala Ala Val Glu Glu Gly Ile Val Ala Gly Gly Gly Val Thr
                405                 410                 415

Leu Leu Gln Ala Ala Pro Thr Leu Asp Glu Leu Lys Leu Glu Gly Asp
```

```
            420                 425                 430

Glu Ala Thr Gly Ala Asn Ile Val Lys Val Ala Leu Glu Ala Pro Leu
        435                 440                 445

Lys Gln Ile Ala Phe Asn Ser Gly Leu Glu Pro Gly Val Val Ala Glu
    450                 455                 460

Lys Val Arg Asn Leu Pro Ala Gly His Gly Leu Asn Ala Gln Thr Gly
465                 470                 475                 480

Val Tyr Glu Asp Leu Leu Ala Ala Gly Val Ala Asp Pro Val Lys Val
                485                 490                 495

Thr Arg Ser Ala Leu Gln Asn Ala Ala Ser Ile Ala Gly Leu Phe Leu
            500                 505                 510

Thr Thr Glu Ala Val Val Ala Asp Lys Pro Glu Lys Glu Lys Ala Ser
        515                 520                 525

Val Pro Gly Gly Gly Asp Met Gly Gly Met Asp Phe
    530                 535                 540


<210> SEQ ID NO 12
<211> LENGTH: 199
<212> TYPE: PRT
<213> ORGANISM: Mycobacterium tuberculosis

<400> SEQUENCE: 12

Met Ala Glu Asn Ser Asn Ile Asp Asp Ile Lys Ala Pro Leu Leu Ala
1               5                   10                  15

Ala Leu Gly Ala Ala Asp Leu Ala Leu Ala Thr Val Asn Glu Leu Ile
            20                  25                  30

Thr Asn Leu Arg Glu Arg Ala Glu Glu Thr Arg Thr Asp Thr Arg Ser
        35                  40                  45

Arg Val Glu Glu Ser Arg Ala Arg Leu Thr Lys Leu Gln Glu Asp Leu
    50                  55                  60

Pro Glu Gln Leu Thr Glu Leu Arg Glu Lys Phe Thr Ala Glu Glu Leu
65                  70                  75                  80

Arg Lys Ala Ala Glu Gly Tyr Leu Glu Ala Ala Thr Ser Arg Tyr Asn
                85                  90                  95

Glu Leu Val Glu Arg Gly Glu Ala Ala Leu Glu Arg Leu Arg Ser Gln
            100                 105                 110

Gln Ser Phe Glu Glu Val Ser Ala Arg Ala Glu Gly Tyr Val Asp Gln
        115                 120                 125

Ala Val Glu Leu Thr Gln Glu Ala Leu Gly Thr Val Ala Ser Gln Thr
    130                 135                 140

Arg Ala Val Gly Glu Arg Ala Ala Lys Leu Val Gly Ile Glu Leu Pro
145                 150                 155                 160

Lys Lys Ala Ala Pro Ala Lys Lys Ala Ala Pro Ala Lys Lys Ala Ala
                165                 170                 175

Pro Ala Lys Lys Ala Ala Ala Lys Lys Ala Pro Ala Lys Lys Ala Ala
            180                 185                 190

Ala Lys Lys Val Thr Gln Lys
        195


<210> SEQ ID NO 13
<211> LENGTH: 375
<212> TYPE: PRT
<213> ORGANISM: Mycobacterium tuberculosis

<400> SEQUENCE: 13

Val Thr Gln Thr Gly Lys Arg Gln Arg Arg Lys Phe Gly Arg Ile Arg
```

```
1               5                   10                  15

Gln Phe Asn Ser Gly Arg Trp Gln Ala Ser Tyr Thr Gly Pro Asp Gly
            20                  25                  30

Arg Val Tyr Ile Ala Pro Lys Thr Phe Asn Ala Lys Ile Asp Ala Glu
        35                  40                  45

Ala Trp Leu Thr Asp Arg Arg Arg Glu Ile Asp Arg Gln Leu Trp Ser
    50                  55                  60

Pro Ala Ser Gly Gln Glu Asp Arg Pro Gly Ala Pro Phe Gly Glu Tyr
65                  70                  75                  80

Ala Glu Gly Trp Leu Lys Gln Arg Gly Ile Lys Asp Arg Thr Arg Ala
                85                  90                  95

His Tyr Arg Lys Leu Leu Asp Asn His Ile Leu Ala Thr Phe Ala Asp
            100                 105                 110

Thr Asp Leu Arg Asp Ile Thr Pro Ala Ala Val Arg Arg Trp Tyr Ala
        115                 120                 125

Thr Thr Ala Val Gly Thr Pro Thr Met Arg Ala His Ser Tyr Ser Leu
    130                 135                 140

Leu Arg Ala Ile Met Gln Thr Ala Leu Ala Asp Asp Leu Ile Asp Ser
145                 150                 155                 160

Asn Pro Cys Arg Ile Ser Gly Ala Ser Thr Ala Arg Arg Val His Lys
                165                 170                 175

Ile Arg Pro Ala Thr Leu Asp Glu Leu Glu Thr Ile Thr Lys Ala Met
            180                 185                 190

Pro Asp Pro Tyr Gln Ala Phe Val Leu Met Ala Ala Trp Leu Ala Met
        195                 200                 205

Arg Tyr Gly Glu Leu Thr Glu Leu Arg Arg Lys Asp Ile Asp Leu His
    210                 215                 220

Gly Glu Val Ala Arg Val Arg Arg Ala Val Val Arg Val Gly Glu Gly
225                 230                 235                 240

Phe Lys Val Thr Thr Pro Lys Ser Asp Ala Gly Val Arg Asp Ile Ser
                245                 250                 255

Ile Pro Pro His Leu Ile Pro Ala Ile Glu Asp His Leu His Lys His
            260                 265                 270

Val Asn Pro Gly Arg Glu Ser Leu Leu Phe Pro Ser Val Asn Asp Pro
        275                 280                 285

Asn Arg His Leu Ala Pro Ser Ala Leu Tyr Arg Met Phe Tyr Lys Ala
    290                 295                 300

Arg Lys Ala Ala Gly Arg Pro Asp Leu Arg Val His Asp Leu Arg His
305                 310                 315                 320

Ser Gly Ala Val Leu Ala Ala Ser Thr Gly Ala Thr Leu Ala Glu Leu
                325                 330                 335

Met Gln Arg Leu Gly His Ser Thr Ala Gly Ala Ala Leu Arg Tyr Gln
            340                 345                 350

His Ala Ala Lys Gly Arg Asp Arg Glu Ile Ala Ala Leu Leu Ser Lys
        355                 360                 365

Leu Ala Glu Asn Gln Glu Met
    370                 375


<210> SEQ ID NO 14
<211> LENGTH: 75
<212> TYPE: PRT
<213> ORGANISM: Mycobacterium tuberculosis

<400> SEQUENCE: 14
```

```
Val Ile Ala Gly Val Asp Gln Ala Leu Ala Ala Thr Gly Gln Ala Ser
1               5                   10                  15

Gln Arg Ala Ala Gly Ala Ser Gly Gly Val Thr Val Gly Val Gly Val
            20                  25                  30

Gly Thr Glu Gln Arg Asn Leu Ser Val Val Ala Pro Ser Gln Phe Thr
        35                  40                  45

Phe Ser Ser Arg Ser Pro Asp Phe Val Asp Glu Thr Ala Gly Gln Ser
    50                  55                  60

Trp Cys Ala Ile Leu Gly Leu Asn Gln Phe His
65                  70                  75


<210> SEQ ID NO 15
<211> LENGTH: 144
<212> TYPE: PRT
<213> ORGANISM: Mycobacterium tuberculosis

<400> SEQUENCE: 15

Met Ala Thr Thr Leu Pro Val Gln Arg His Pro Arg Ser Leu Phe Pro
1               5                   10                  15

Glu Phe Ser Glu Leu Phe Ala Ala Phe Pro Ser Phe Ala Gly Leu Arg
            20                  25                  30

Pro Thr Phe Asp Thr Arg Leu Met Arg Leu Glu Asp Glu Met Lys Glu
        35                  40                  45

Gly Arg Tyr Glu Val Arg Ala Glu Leu Pro Gly Val Asp Pro Asp Lys
    50                  55                  60

Asp Val Asp Ile Met Val Arg Asp Gly Gln Leu Thr Ile Lys Ala Glu
65                  70                  75                  80

Arg Thr Glu Gln Lys Asp Phe Asp Gly Arg Ser Glu Phe Ala Tyr Gly
                85                  90                  95

Ser Phe Val Arg Thr Val Ser Leu Pro Val Gly Ala Asp Glu Asp Asp
            100                 105                 110

Ile Lys Ala Thr Tyr Asp Lys Gly Ile Leu Thr Val Ser Val Ala Val
        115                 120                 125

Ser Glu Gly Lys Pro Thr Glu Lys His Ile Gln Ile Arg Ser Thr Asn
    130                 135                 140


<210> SEQ ID NO 16
<211> LENGTH: 407
<212> TYPE: PRT
<213> ORGANISM: Mycobacterium tuberculosis

<400> SEQUENCE: 16

Met Ser Gly Arg His Arg Lys Pro Thr Thr Ser Asn Val Ser Val Ala
1               5                   10                  15

Lys Ile Ala Phe Thr Gly Ala Val Leu Gly Gly Gly Gly Ile Ala Met
            20                  25                  30

Ala Ala Gln Ala Thr Ala Ala Thr Asp Gly Glu Trp Asp Gln Val Ala
        35                  40                  45

Arg Cys Glu Ser Gly Gly Asn Trp Ser Ile Asn Thr Gly Asn Gly Tyr
    50                  55                  60

Leu Gly Gly Leu Gln Phe Thr Gln Ser Thr Trp Ala Ala His Gly Gly
65                  70                  75                  80

Gly Glu Phe Ala Pro Ser Ala Gln Leu Ala Ser Arg Glu Gln Gln Ile
                85                  90                  95

Ala Val Gly Glu Arg Val Leu Ala Thr Gln Gly Arg Gly Ala Trp Pro
            100                 105                 110
```

```
Val Cys Gly Arg Gly Leu Ser Asn Ala Thr Pro Arg Glu Val Leu Pro
        115                 120                 125

Ala Ser Ala Ala Met Asp Ala Pro Leu Asp Ala Ala Ala Val Asn Gly
    130                 135                 140

Glu Pro Ala Pro Leu Ala Pro Pro Pro Ala Asp Pro Ala Pro Pro Val
145                 150                 155                 160

Glu Leu Ala Ala Asn Asp Leu Pro Ala Pro Leu Gly Glu Pro Leu Pro
                165                 170                 175

Ala Ala Pro Ala Asp Pro Ala Pro Pro Ala Asp Leu Ala Pro Pro Ala
            180                 185                 190

Pro Ala Asp Val Ala Pro Pro Val Glu Leu Ala Val Asn Asp Leu Pro
        195                 200                 205

Ala Pro Leu Gly Glu Pro Leu Pro Ala Ala Pro Ala Asp Pro Ala Pro
    210                 215                 220

Pro Ala Asp Leu Ala Pro Pro Ala Pro Ala Asp Leu Ala Pro Pro Ala
225                 230                 235                 240

Pro Ala Asp Leu Ala Pro Pro Ala Pro Ala Asp Leu Ala Pro Pro Val
                245                 250                 255

Glu Leu Ala Val Asn Asp Leu Pro Ala Pro Leu Gly Glu Pro Leu Pro
            260                 265                 270

Ala Ala Pro Ala Glu Leu Ala Pro Pro Ala Asp Leu Ala Pro Ala Ser
        275                 280                 285

Ala Asp Leu Ala Pro Pro Ala Pro Ala Asp Leu Ala Pro Pro Ala Pro
    290                 295                 300

Ala Glu Leu Ala Pro Pro Ala Pro Ala Asp Leu Ala Pro Pro Ala Ala
305                 310                 315                 320

Val Asn Glu Gln Thr Ala Pro Gly Asp Gln Pro Ala Thr Ala Pro Gly
                325                 330                 335

Gly Pro Val Gly Leu Ala Thr Asp Leu Glu Leu Pro Glu Pro Asp Pro
            340                 345                 350

Gln Pro Ala Asp Ala Pro Pro Pro Gly Asp Val Thr Glu Ala Pro Ala
        355                 360                 365

Glu Thr Pro Gln Val Ser Asn Ile Ala Tyr Thr Lys Lys Leu Trp Gln
    370                 375                 380

Ala Ile Arg Ala Gln Asp Val Cys Gly Asn Asp Ala Leu Asp Ser Leu
385                 390                 395                 400

Ala Gln Pro Tyr Val Ile Gly
                405


<210> SEQ ID NO 17
<211> LENGTH: 362
<212> TYPE: PRT
<213> ORGANISM: Mycobacterium tuberculosis

<400> SEQUENCE: 17

Met Leu Arg Leu Val Val Gly Ala Leu Leu Leu Val Leu Ala Phe Ala
1               5                   10                  15

Gly Gly Tyr Ala Val Ala Ala Cys Lys Thr Val Thr Leu Thr Val Asp
            20                  25                  30

Gly Thr Ala Met Arg Val Thr Thr Met Lys Ser Arg Val Ile Asp Ile
        35                  40                  45

Val Glu Glu Asn Gly Phe Ser Val Asp Asp Arg Asp Asp Leu Tyr Pro
    50                  55                  60

Ala Ala Gly Val Gln Val His Asp Ala Asp Thr Ile Val Leu Arg Arg
65                  70                  75                  80
```

```
Ser Arg Pro Leu Gln Ile Ser Leu Asp Gly His Asp Ala Lys Gln Val
                85                  90                  95

Trp Thr Thr Ala Ser Thr Val Asp Glu Ala Leu Ala Gln Leu Ala Met
            100                 105                 110

Thr Asp Thr Ala Pro Ala Ala Ala Ser Arg Ala Ser Arg Val Pro Leu
        115                 120                 125

Ser Gly Met Ala Leu Pro Val Val Ser Ala Lys Thr Val Gln Leu Asn
    130                 135                 140

Asp Gly Gly Leu Val Arg Thr Val His Leu Pro Ala Pro Asn Val Ala
145                 150                 155                 160

Gly Leu Leu Ser Ala Ala Gly Val Pro Leu Leu Gln Ser Asp His Val
                165                 170                 175

Val Pro Ala Ala Thr Ala Pro Ile Val Glu Gly Met Gln Ile Gln Val
            180                 185                 190

Thr Arg Asn Arg Ile Lys Lys Val Thr Glu Arg Leu Pro Leu Pro Pro
        195                 200                 205

Asn Ala Arg Arg Val Glu Asp Pro Glu Met Asn Met Ser Arg Glu Val
    210                 215                 220

Val Glu Asp Pro Gly Val Pro Gly Thr Gln Asp Val Thr Phe Ala Val
225                 230                 235                 240

Ala Glu Val Asn Gly Val Glu Thr Gly Arg Leu Pro Val Ala Asn Val
                245                 250                 255

Val Val Thr Pro Ala His Glu Ala Val Val Arg Val Gly Thr Lys Pro
            260                 265                 270

Gly Thr Glu Val Pro Pro Val Ile Asp Gly Ser Ile Trp Asp Ala Ile
        275                 280                 285

Ala Gly Cys Glu Ala Gly Gly Asn Trp Ala Ile Asn Thr Gly Asn Gly
    290                 295                 300

Tyr Tyr Gly Gly Val Gln Phe Asp Gln Gly Thr Trp Glu Ala Asn Gly
305                 310                 315                 320

Gly Leu Arg Tyr Ala Pro Arg Ala Asp Leu Ala Thr Arg Glu Glu Gln
                325                 330                 335

Ile Ala Val Ala Glu Val Thr Arg Leu Arg Gln Gly Trp Gly Ala Trp
            340                 345                 350

Pro Val Cys Ala Ala Arg Ala Gly Ala Arg
        355                 360


<210> SEQ ID NO 18
<211> LENGTH: 176
<212> TYPE: PRT
<213> ORGANISM: Mycobacterium tuberculosis

<400> SEQUENCE: 18

Val His Pro Leu Pro Ala Asp His Gly Arg Ser Arg Cys Asn Arg His
1               5                   10                  15

Pro Ile Ser Pro Leu Ser Leu Ile Gly Asn Ala Ser Ala Thr Ser Gly
            20                  25                  30

Asp Met Ser Ser Met Thr Arg Ile Ala Lys Pro Leu Ile Lys Ser Ala
        35                  40                  45

Met Ala Ala Gly Leu Val Thr Ala Ser Met Ser Leu Ser Thr Ala Val
    50                  55                  60

Ala His Ala Gly Pro Ser Pro Asn Trp Asp Ala Val Ala Gln Cys Glu
65                  70                  75                  80

Ser Gly Gly Asn Trp Ala Ala Asn Thr Gly Asn Gly Lys Tyr Gly Gly
```

```
                85                  90                  95

Leu Gln Phe Lys Pro Ala Thr Trp Ala Ala Phe Gly Gly Val Gly Asn
            100                 105                 110

Pro Ala Ala Ala Ser Arg Glu Gln Gln Ile Ala Val Ala Asn Arg Val
        115                 120                 125

Leu Ala Glu Gln Gly Leu Asp Ala Trp Pro Thr Cys Gly Ala Ala Ser
    130                 135                 140

Gly Leu Pro Ile Ala Leu Trp Ser Lys Pro Ala Gln Gly Ile Lys Gln
145                 150                 155                 160

Ile Ile Asn Glu Ile Ile Trp Ala Gly Ile Gln Ala Ser Ile Pro Arg
                165                 170                 175


<210> SEQ ID NO 19
<211> LENGTH: 154
<212> TYPE: PRT
<213> ORGANISM: Mycobacterium tuberculosis

<400> SEQUENCE: 19

Met Thr Pro Gly Leu Leu Thr Thr Ala Gly Ala Gly Arg Pro Arg Asp
1               5                   10                  15

Arg Cys Ala Arg Ile Val Cys Thr Val Phe Ile Glu Thr Ala Val Val
            20                  25                  30

Ala Thr Met Phe Val Ala Leu Leu Gly Leu Ser Thr Ile Ser Ser Lys
        35                  40                  45

Ala Asp Asp Ile Asp Trp Asp Ala Ile Ala Gln Cys Glu Ser Gly Gly
    50                  55                  60

Asn Trp Ala Ala Asn Thr Gly Asn Gly Leu Tyr Gly Gly Leu Gln Ile
65                  70                  75                  80

Ser Gln Ala Thr Trp Asp Ser Asn Gly Gly Val Gly Ser Pro Ala Ala
                85                  90                  95

Ala Ser Pro Gln Gln Gln Ile Glu Val Ala Asp Asn Ile Met Lys Thr
            100                 105                 110

Gln Gly Pro Gly Ala Trp Pro Lys Cys Ser Ser Cys Ser Gln Gly Asp
        115                 120                 125

Ala Pro Leu Gly Ser Leu Thr His Ile Leu Thr Phe Leu Ala Ala Glu
    130                 135                 140

Thr Gly Gly Cys Ser Gly Ser Arg Asp Asp
145                 150


<210> SEQ ID NO 20
<211> LENGTH: 172
<212> TYPE: PRT
<213> ORGANISM: Mycobacterium tuberculosis

<400> SEQUENCE: 20

Leu Lys Asn Ala Arg Thr Thr Leu Ile Ala Ala Ala Ile Ala Gly Thr
1               5                   10                  15

Leu Val Thr Thr Ser Pro Ala Gly Ile Ala Asn Ala Asp Asp Ala Gly
            20                  25                  30

Leu Asp Pro Asn Ala Ala Ala Gly Pro Asp Ala Val Gly Phe Asp Pro
        35                  40                  45

Asn Leu Pro Pro Ala Pro Asp Ala Ala Pro Val Asp Thr Pro Pro Ala
    50                  55                  60

Pro Glu Asp Ala Gly Phe Asp Pro Asn Leu Pro Pro Pro Leu Ala Pro
65                  70                  75                  80

Asp Phe Leu Ser Pro Pro Ala Glu Glu Ala Pro Pro Val Pro Val Ala
```

```
                85                  90                  95

Tyr Ser Val Asn Trp Asp Ala Ile Ala Gln Cys Glu Ser Gly Gly Asn
            100                 105                 110

Trp Ser Ile Asn Thr Gly Asn Gly Tyr Tyr Gly Gly Leu Arg Phe Thr
        115                 120                 125

Ala Gly Thr Trp Arg Ala Asn Gly Gly Ser Gly Ser Ala Ala Asn Ala
    130                 135                 140

Ser Arg Glu Glu Gln Ile Arg Val Ala Glu Asn Val Leu Arg Ser Gln
145                 150                 155                 160

Gly Ile Arg Ala Trp Pro Val Cys Gly Arg Arg Gly
                165                 170


<210> SEQ ID NO 21
<211> LENGTH: 210
<212> TYPE: PRT
<213> ORGANISM: Mycobacterium tuberculosis

<400> SEQUENCE: 21

Met Ile Ala Thr Thr Arg Asp Arg Glu Gly Ala Thr Met Ile Thr Phe
1               5                   10                  15

Arg Leu Arg Leu Pro Cys Arg Thr Ile Leu Arg Val Phe Ser Arg Asn
            20                  25                  30

Pro Leu Val Arg Gly Thr Asp Arg Leu Glu Ala Val Val Met Leu Leu
        35                  40                  45

Ala Val Thr Val Ser Leu Leu Thr Ile Pro Phe Ala Ala Ala Ala Gly
    50                  55                  60

Thr Ala Val Gln Asp Ser Arg Ser His Val Tyr Ala His Gln Ala Gln
65                  70                  75                  80

Thr Arg His Pro Ala Thr Ala Thr Val Ile Asp His Glu Gly Val Ile
                85                  90                  95

Asp Ser Asn Thr Thr Ala Thr Ser Ala Pro Pro Arg Thr Lys Ile Thr
            100                 105                 110

Val Pro Ala Arg Trp Val Val Asn Gly Ile Glu Arg Ser Gly Glu Val
        115                 120                 125

Asn Ala Lys Pro Gly Thr Lys Ser Gly Asp Arg Val Gly Ile Trp Val
    130                 135                 140

Asp Ser Ala Gly Gln Leu Val Asp Glu Pro Ala Pro Pro Ala Arg Ala
145                 150                 155                 160

Ile Ala Asp Ala Ala Leu Ala Ala Leu Gly Leu Trp Leu Ser Val Ala
                165                 170                 175

Ala Val Ala Gly Ala Leu Leu Ala Leu Thr Arg Ala Ile Leu Ile Arg
            180                 185                 190

Val Arg Asn Ala Ser Trp Gln His Asp Ile Asp Ser Leu Phe Cys Thr
        195                 200                 205

Gln Arg
    210


<210> SEQ ID NO 22
<211> LENGTH: 339
<212> TYPE: PRT
<213> ORGANISM: Mycobacterium tuberculosis

<400> SEQUENCE: 22

Met Thr Glu Pro Ala Ala Trp Asp Glu Gly Lys Pro Arg Ile Ile Thr
1               5                   10                  15

Leu Thr Met Asn Pro Ala Leu Asp Ile Thr Thr Ser Val Asp Val Val
```

-continued

```
            20                  25                  30

Arg Pro Thr Glu Lys Met Arg Cys Gly Ala Pro Arg Tyr Asp Pro Gly
        35                  40                  45

Gly Gly Gly Ile Asn Val Ala Arg Ile Val His Val Leu Gly Gly Cys
    50                  55                  60

Ser Thr Ala Leu Phe Pro Ala Gly Gly Ser Thr Gly Ser Leu Leu Met
65                  70                  75                  80

Ala Leu Leu Gly Asp Ala Gly Val Pro Phe Arg Val Ile Pro Ile Ala
                85                  90                  95

Ala Ser Thr Arg Glu Ser Phe Thr Val Asn Glu Ser Arg Thr Ala Lys
            100                 105                 110

Gln Tyr Arg Phe Val Leu Pro Gly Pro Ser Leu Thr Val Ala Glu Gln
        115                 120                 125

Glu Gln Cys Leu Asp Glu Leu Arg Gly Ala Ala Ala Ser Ala Ala Phe
    130                 135                 140

Val Val Ala Ser Gly Ser Leu Pro Pro Gly Val Ala Ala Asp Tyr Tyr
145                 150                 155                 160

Gln Arg Val Ala Asp Ile Cys Arg Arg Ser Ser Thr Pro Leu Ile Leu
                165                 170                 175

Asp Thr Ser Gly Gly Gly Leu Gln His Ile Ser Ser Gly Val Phe Leu
            180                 185                 190

Leu Lys Ala Ser Val Arg Glu Leu Arg Glu Cys Val Gly Ser Glu Leu
        195                 200                 205

Leu Thr Glu Pro Glu Gln Leu Ala Ala Ala His Glu Leu Ile Asp Arg
    210                 215                 220

Gly Arg Ala Glu Val Val Val Val Ser Leu Gly Ser Gln Gly Ala Leu
225                 230                 235                 240

Leu Ala Thr Arg His Ala Ser His Arg Phe Ser Ser Ile Pro Met Thr
                245                 250                 255

Ala Val Ser Gly Val Gly Ala Gly Asp Ala Met Val Ala Ala Ile Thr
            260                 265                 270

Val Gly Leu Ser Arg Gly Trp Ser Leu Ile Lys Ser Val Arg Leu Gly
        275                 280                 285

Asn Ala Ala Gly Ala Ala Met Leu Leu Thr Pro Gly Thr Ala Ala Cys
    290                 295                 300

Asn Arg Asp Asp Val Glu Arg Phe Phe Glu Leu Ala Ala Glu Pro Thr
305                 310                 315                 320

Glu Val Gly Gln Asp Gln Tyr Val Trp His Pro Ile Val Asn Pro Glu
                325                 330                 335

Ala Ser Pro


<210> SEQ ID NO 23
<211> LENGTH: 331
<212> TYPE: PRT
<213> ORGANISM: Mycobacterium tuberculosis

<400> SEQUENCE: 23

Met Pro Asp Thr Met Val Thr Thr Asp Val Ile Lys Ser Ala Val Gln
1               5                   10                  15

Leu Ala Cys Arg Ala Pro Ser Leu His Asn Ser Gln Pro Trp Arg Trp
            20                  25                  30

Ile Ala Glu Asp His Thr Val Ala Leu Phe Leu Asp Lys Asp Arg Val
        35                  40                  45

Leu Tyr Ala Thr Asp His Ser Gly Arg Glu Ala Leu Leu Gly Cys Gly
```

```
    50                  55                  60

Ala Val Leu Asp His Phe Arg Val Ala Met Ala Ala Ala Gly Thr Thr
65                  70                  75                  80

Ala Asn Val Glu Arg Phe Pro Asn Pro Asn Asp Pro Leu His Leu Ala
                85                  90                  95

Ser Ile Asp Phe Ser Pro Ala Asp Phe Val Thr Glu Gly His Arg Leu
            100                 105                 110

Arg Ala Asp Ala Ile Leu Leu Arg Arg Thr Asp Arg Leu Pro Phe Ala
        115                 120                 125

Glu Pro Pro Asp Trp Asp Leu Val Glu Ser Gln Leu Arg Thr Thr Val
    130                 135                 140

Thr Ala Asp Thr Val Arg Ile Asp Val Ile Ala Asp Asp Met Arg Pro
145                 150                 155                 160

Glu Leu Ala Ala Ala Ser Lys Leu Thr Glu Ser Leu Arg Leu Tyr Asp
                165                 170                 175

Ser Ser Tyr His Ala Glu Leu Phe Trp Trp Thr Gly Ala Phe Glu Thr
            180                 185                 190

Ser Glu Gly Ile Pro His Ser Ser Leu Val Ser Ala Ala Glu Ser Asp
        195                 200                 205

Arg Val Thr Phe Gly Arg Asp Phe Pro Val Val Ala Asn Thr Asp Arg
    210                 215                 220

Arg Pro Glu Phe Gly His Asp Arg Ser Lys Val Leu Val Leu Ser Thr
225                 230                 235                 240

Tyr Asp Asn Glu Arg Ala Ser Leu Leu Arg Cys Gly Glu Met Leu Ser
                245                 250                 255

Ala Val Leu Leu Asp Ala Thr Met Ala Gly Leu Ala Thr Cys Thr Leu
            260                 265                 270

Thr His Ile Thr Glu Leu His Ala Ser Arg Asp Leu Val Ala Ala Leu
        275                 280                 285

Ile Gly Gln Pro Ala Thr Pro Gln Ala Leu Val Arg Val Gly Leu Ala
    290                 295                 300

Pro Glu Met Glu Glu Pro Pro Pro Ala Thr Pro Arg Arg Pro Ile Asp
305                 310                 315                 320

Glu Val Phe His Val Arg Ala Lys Asp His Arg
                325                 330


<210> SEQ ID NO 24
<211> LENGTH: 143
<212> TYPE: PRT
<213> ORGANISM: Mycobacterium tuberculosis

<400> SEQUENCE: 24

Met Thr Thr Ala Arg Asp Ile Met Asn Ala Gly Val Thr Cys Val Gly
1               5                   10                  15

Glu His Glu Thr Leu Thr Ala Ala Ala Gln Tyr Met Arg Glu His Asp
            20                  25                  30

Ile Gly Ala Leu Pro Ile Cys Gly Asp Asp Asp Arg Leu His Gly Met
        35                  40                  45

Leu Thr Asp Arg Asp Ile Val Ile Lys Gly Leu Ala Ala Gly Leu Asp
    50                  55                  60

Pro Asn Thr Ala Thr Ala Gly Glu Leu Ala Arg Asp Ser Ile Tyr Tyr
65                  70                  75                  80

Val Asp Ala Asn Ala Ser Ile Gln Glu Met Leu Asn Val Met Glu Glu
                85                  90                  95
```

```
His Gln Val Arg Arg Val Pro Val Ile Ser Glu His Arg Leu Val Gly
            100                 105                 110

Ile Val Thr Glu Ala Asp Ile Ala Arg His Leu Pro Glu His Ala Ile
        115                 120                 125

Val Gln Phe Val Lys Ala Ile Cys Ser Pro Met Ala Leu Ala Ser
    130                 135                 140


<210> SEQ ID NO 25
<211> LENGTH: 413
<212> TYPE: PRT
<213> ORGANISM: Mycobacterium tuberculosis

<400> SEQUENCE: 25

Met Ala Ser Ser Ala Ser Asp Gly Thr His Glu Arg Ser Ala Phe Arg
1               5                   10                  15

Leu Ser Pro Pro Val Leu Ser Gly Ala Met Gly Pro Phe Met His Thr
            20                  25                  30

Gly Leu Tyr Val Ala Gln Ser Trp Arg Asp Tyr Leu Gly Gln Gln Pro
        35                  40                  45

Asp Lys Leu Pro Ile Ala Arg Pro Thr Ile Ala Leu Ala Ala Gln Ala
    50                  55                  60

Phe Arg Asp Glu Ile Val Leu Leu Gly Leu Lys Ala Arg Arg Pro Val
65                  70                  75                  80

Ser Asn His Arg Val Phe Glu Arg Ile Ser Gln Glu Val Ala Ala Gly
                85                  90                  95

Leu Glu Phe Tyr Gly Asn Arg Arg Trp Leu Glu Lys Pro Ser Gly Phe
            100                 105                 110

Phe Ala Gln Pro Pro Pro Leu Thr Glu Val Ala Val Arg Lys Val Lys
        115                 120                 125

Asp Arg Arg Arg Ser Phe Tyr Arg Ile Phe Phe Asp Ser Gly Phe Thr
    130                 135                 140

Pro His Pro Gly Glu Pro Gly Ser Gln Arg Trp Leu Ser Tyr Thr Ala
145                 150                 155                 160

Asn Asn Arg Glu Tyr Ala Leu Leu Leu Arg His Pro Glu Pro Arg Pro
                165                 170                 175

Trp Leu Val Cys Val His Gly Thr Glu Met Gly Arg Ala Pro Leu Asp
            180                 185                 190

Leu Ala Val Phe Arg Ala Trp Lys Leu His Asp Glu Leu Gly Leu Asn
        195                 200                 205

Ile Val Met Pro Val Leu Pro Met His Gly Pro Arg Gly Gln Gly Leu
    210                 215                 220

Pro Lys Gly Ala Val Phe Pro Gly Glu Asp Val Leu Asp Asp Val His
225                 230                 235                 240

Gly Thr Ala Gln Ala Val Trp Asp Ile Arg Arg Leu Leu Ser Trp Ile
                245                 250                 255

Arg Ser Gln Glu Glu Glu Ser Leu Ile Gly Leu Asn Gly Leu Ser Leu
            260                 265                 270

Gly Gly Tyr Ile Ala Ser Leu Val Ala Ser Leu Glu Glu Gly Leu Ala
        275                 280                 285

Cys Ala Ile Leu Gly Val Pro Val Ala Asp Leu Ile Glu Leu Leu Gly
    290                 295                 300

Arg His Cys Gly Leu Arg His Lys Asp Pro Arg Arg His Thr Val Lys
305                 310                 315                 320

Met Ala Glu Pro Ile Gly Arg Met Ile Ser Pro Leu Ser Leu Thr Pro
                325                 330                 335
```

```
Leu Val Pro Met Pro Gly Arg Phe Ile Tyr Ala Gly Ile Ala Asp Arg
            340                 345                 350

Leu Val His Pro Arg Glu Gln Val Thr Arg Leu Trp Glu His Trp Gly
        355                 360                 365

Lys Pro Glu Ile Val Trp Tyr Pro Gly Gly His Thr Gly Phe Phe Gln
    370                 375                 380

Ser Arg Pro Val Arg Arg Phe Val Gln Ala Ala Leu Glu Gln Ser Gly
385                 390                 395                 400

Leu Leu Asp Ala Pro Arg Thr Gln Arg Asp Arg Ser Ala
                405                 410


<210> SEQ ID NO 26
<211> LENGTH: 120
<212> TYPE: PRT
<213> ORGANISM: Mycobacterium tuberculosis

<400> SEQUENCE: 26

Met Ser Thr Gln Arg Pro Arg His Ser Gly Ile Arg Ala Val Gly Pro
1               5                   10                  15

Tyr Ala Trp Ala Gly Arg Cys Gly Arg Ile Gly Arg Trp Gly Val His
            20                  25                  30

Gln Glu Ala Met Met Asn Leu Ala Ile Trp His Pro Arg Lys Val Gln
        35                  40                  45

Ser Ala Thr Ile Tyr Gln Val Thr Asp Arg Ser His Asp Gly Arg Thr
    50                  55                  60

Ala Arg Val Pro Gly Asp Glu Ile Thr Ser Thr Val Ser Gly Trp Leu
65                  70                  75                  80

Ser Glu Leu Gly Thr Gln Ser Pro Leu Ala Asp Glu Leu Ala Arg Ala
                85                  90                  95

Val Arg Ile Gly Asp Trp Pro Ala Ala Tyr Ala Ile Gly Glu His Leu
            100                 105                 110

Ser Val Glu Ile Ala Val Ala Val
        115                 120


<210> SEQ ID NO 27
<211> LENGTH: 1017
<212> TYPE: DNA
<213> ORGANISM: Mycobacterium tuberculosis

<400> SEQUENCE: 27

atgcagcttg ttgacagggt tcgtggcgcc gtcacgggta tgtcgcgtcg actcgtggtc      60

ggggccgtcg gcgcggccct agtgtcgggt ctggtcggcg ccgtcggtgg cacggcgacc     120

gcgggggcat tttcccggcc gggcttgccg gtggagtacc tgcaggtgcc gtcgccgtcg     180

atgggccgtg acatcaaggt ccaattccaa agtggtggtg ccaactcgcc cgccctgtac     240

ctgctcgacg gcctgcgcgc gcaggacgac ttcagcggct gggacatcaa caccccggcg     300

ttcgagtggt acgaccagtc gggcctgtcg gtggtcatgc cggtgggtgg ccagtcaagc     360

ttctactccg actggtacca gcccgcctgc ggcaaggccg gttgccagac ttacaagtgg     420

gagaccttcc tgaccagcga gctgccgggg tggctgcagg ccaacaggca cgtcaagccc     480

accggaagcg ccgtcgtcgg tctttcgatg gctgcttctt cggcgctgac gctggcgatc     540

tatcaccccc agcagttcgt ctacgcggga gcgatgtcgg gcctgttgga cccctcccag     600

gcgatgggtc ccaccctgat cggcctggcg atgggtgacg ctggcggcta caaggcctcc     660

gacatgtggg gcccgaagga ggacccggcg tggcagcgca acgacccgct gttgaacgtc     720
```

-continued

```
gggaagctga tcgccaacaa cacccgcgtc tgggtgtact gcggcaacgg caagccgtcg    780
gatctgggtg gcaacaacct gccggccaag ttcctcgagg gcttcgtgcg gaccagcaac    840
atcaagttcc aagacgccta caacgccggt ggcggccaca acggcgtgtt cgacttcccg    900
gacagcggta cgcacagctg ggagtactgg ggcgcgcagc tcaacgctat gaagcccgac    960
ctgcaacggg cactgggtgc cacgcccaac accgggcccg cgccccaggg cgcctag      1017
```

<210> SEQ ID NO 28
<211> LENGTH: 978
<212> TYPE: DNA
<213> ORGANISM: Mycobacterium tuberculosis

<400> SEQUENCE: 28

```
atgacagacg tgagccgaaa gattcgagct tggggacgcc gattgatgat cggcacggca     60
gcggctgtag tccttccggg cctggtgggg cttgccggcg gagcggcaac cgcgggcgcg    120
ttctcccggc cggggctgcc ggtcgagtac ctgcaggtgc cgtcgccgtc gatgggccgc    180
gacatcaagg ttcagttcca gagcggtggg aacaactcac ctgcggttta tctgctcgac    240
ggcctgcgcg cccaagacga ctacaacggc tgggatatca acaccccggc gttcgagtgg    300
tactaccagt cgggactgtc gatagtcatg ccggtcggcg ggcagtccag cttctacagc    360
gactggtaca gcccggcctg cggtaaggct ggctgccaga cttacaagtg ggaaaccttc    420
ctgaccagcg agctgccgca atggttgtcc gccaacaggg ccgtgaagcc caccggcagc    480
gctgcaatcg gcttgtcgat ggccggctcg tcggcaatga tcttggccgc ctaccacccc    540
cagcagttca tctacgccgg ctcgctgtcg gccctgctgg acccctctca ggggatgggg    600
cctagcctga tcggcctcgc gatgggtgac gccggcggtt acaaggccgc agacatgtgg    660
ggtccctcga gtgacccggc atgggagcgc aacgacccta cgcagcagat ccccaagctg    720
gtcgcaaaca acacccggct atgggtttat tgcgggaacg gcaccccgaa cgagttgggc    780
ggtgccaaca tacccgccga gttcttggag aacttcgttc gtagcagcaa cctgaagttc    840
caggatgcgt acaacgccgc gggcgggcac aacgccgtgt tcaacttccc gcccaacggc    900
acgcacagct gggagtactg gggcgctcag ctcaacgcca tgaagggtga cctgcagagt    960
tcgttaggcg ccggctga                                                  978
```

<210> SEQ ID NO 29
<211> LENGTH: 1023
<212> TYPE: DNA
<213> ORGANISM: Mycobacterium tuberculosis

<400> SEQUENCE: 29

```
atgacgttct tcgaacaggt gcgaaggttg cggagcgcag cgacaaccct gccgcgccgc     60
gtggctatcg cggctatggg ggctgtcctg gtttacggtc tggtcggtac cttcggcggg    120
ccggccaccg cgggcgcatt ctctaggccc ggtcttccag tggaatatct gcaggtgcca    180
tccgcgtcga tgggccgcga catcaaggtc cagttccagg gcggcggacc gcacgcggtc    240
tacctgctcg acggtctgcg ggcccaggat gactacaacg gctgggacat caacaccccg    300
gccttcgagg agtactacca gtcagggttg tcggtgatca tgcccgtggg cggccaatcc    360
agtttctaca ccgactggta tcagccctcg cagagcaacg gccagaacta cacctacaag    420
tgggagacct tccttaccag agagatgccc gcctggctac aggccaacaa gggcgtgtcc    480
ccgacaggca acgcggcggt gggtctttcg atgtcgggcg gttccgcgct gatcctggcc    540
```

```
gcgtactacc cgcagcagtt cccgtacgcc gcgtcgttgt cgggcttcct caacccgtcc    600
gagggctggt ggccgacgct gatcggcctg gcgatgaacg actcgggcgg ttacaacgcc    660
aacagcatgt ggggtccgtc cagcgacccg gcctggaagc gcaacgaccc aatggttcag    720
attccccgcc tggtcgccaa caacacccgg atctgggtgt actgcggtaa cggcacaccc    780
agcgacctcg gcggcgacaa cataccggcg aagttcctgg aaggcctcac cctgcgcacc    840
aaccagacct tccgggacac ctacgcggcc gacggtggac gcaacggggt gtttaacttc    900
ccgcccaacg gaacacactc gtggccctac tggaacgagc agctggtcgc catgaaggcc    960
gatatccagc atgtgctcaa cggcgcgaca cccccggccg cccctgctgc gccggccgcc   1020
tga                                                                 1023
```

<210> SEQ ID NO 30
<211> LENGTH: 288
<212> TYPE: DNA
<213> ORGANISM: Mycobacterium tuberculosis

<400> SEQUENCE: 30

```
atgacagagc agcagtggaa tttcgcgggt atcgaggccg cggcaagcgc aatccaggga     60
aatgtcacgt ccattcattc cctccttgac gaggggaagc agtccctgac caagctcgca    120
gcggcctggg gcggtagcgg ttcggaggcg taccagggtg tccagcaaaa atgggacgcc    180
acggctaccg agctgaacaa cgcgctgcag aacctggcgc ggacgatcag cgaagccggt    240
caggcaatgg cttcgaccga aggcaacgtc actgggatgt tcgcatag                288
```

<210> SEQ ID NO 31
<211> LENGTH: 291
<212> TYPE: DNA
<213> ORGANISM: Mycobacterium tuberculosis

<400> SEQUENCE: 31

```
atgtcgcaaa tcatgtacaa ctaccccgcg atgttgggtc acgccgggga tatggccgga     60
tatgccggca cgctgcagag cttgggtgcc gagatcgccg tggagcaggc cgcgttgcag    120
agtgcgtggc agggcgatac cgggatcacg tatcaggcgt ggcaggcaca gtggaaccag    180
gccatggaag atttggtgcg ggcctatcat gcgatgtcca gcacccatga agccaacacc    240
atggcgatga tggcccgcga cacggccgaa gccgccaaat ggggcggcta g             291
```

<210> SEQ ID NO 32
<211> LENGTH: 1068
<212> TYPE: DNA
<213> ORGANISM: Mycobacterium tuberculosis

<400> SEQUENCE: 32

```
atgagcaatt cgcgccgccg ctcactcagg tggtcatggt tgctgagcgt gctggctgcc     60
gtcgggctgg gcctggccac ggcgccggcc caggcggccc cgccggcctt gtcgcaggac    120
cggttcgccg acttccccgc gctgcccctc gacccgtccg cgatggtcgc ccaagtgggg    180
ccacaggtgg tcaacatcaa caccaaactg ggctacaaca acgccgtggg cgccgggacc    240
ggcatcgtca tcgatcccaa cggtgtcgtg ctgaccaaca accacgtgat cgcgggcgcc    300
accgacatca atgcgttcag cgtcggctcc ggccaaacct acggcgtcga tgtggtcggg    360
tatgaccgca cccaggatgt cgcggtgctg cagctgcgcg gtgccggtgg cctgccgtcg    420
gcggcgatcg gtggcggcgt cgcggttggt gagcccgtcg tcgcgatggg caacagcggt    480
gggcagggcg gaacgccccg tgcggtgcct ggcagggtgg tcgcgctcgg ccaaaccgtg    540
```

```
caggcgtcgg attcgctgac cggtgccgaa gagacattga acgggttgat ccagttcgat    600

gccgcgatcc agcccggtga ttcgggcggg cccgtcgtca acggcctagg acaggtggtc    660

ggtatgaaca cggccgcgtc cgataacttc cagctgtccc agggtgggca gggattcgcc    720

attccgatcg ggcaggcgat ggcgatcgcg ggccagatcc gatcgggtgg ggggtcaccc    780

accgttcata tcgggcctac cgccttcctc ggcttgggtg ttgtcgacaa caacggcaac    840

ggcgcacgag tccaacgcgt ggtcgggagc gctccggcgg caagtctcgg catctccacc    900

ggcgacgtga tcaccgcggt cgacggcgct ccgatcaact cggccaccgc gatggcggac    960

gcgcttaacg ggcatcatcc cggtgacgtc atctcggtga cctggcaaac caagtcgggc   1020

ggcacgcgta cagggaacgt gacattggcc gagggacccc cggcctga               1068
```

<210> SEQ ID NO 33
<211> LENGTH: 1176
<212> TYPE: DNA
<213> ORGANISM: Mycobacterium tuberculosis

<400> SEQUENCE: 33

```
atggtggatt tcggggcgtt accaccggag atcaactccg cgaggatgta cgccggcccg     60

ggttcggcct cgctggtggc cgcggctcag atgtgggaca gcgtggcgag tgacctgttt    120

tcggccgcgt cggcgtttca gtcggtggtc tggggtctga cggtggggtc gtggataggt    180

tcgtcggcgg gtctgatggt ggcggcggcc tcgccgtatg tggcgtggat gagcgtcacc    240

gcggggcagg ccgagctgac cgccgcccag gtccgggttg ctgcggcggc ctacgagacg    300

gcgtatgggc tgacggtgcc cccgccggtg atcgccgaga accgtgctga actgatgatt    360

ctgatagcga ccaacctctt ggggcaaaac accccggcga tcgcggtcaa cgaggccgaa    420

tacggcgaga tgtgggccca agacgccgcc gcgatgtttg gctacgccgc ggcgacggcg    480

acggcgacgg cgacgttgct gccgttcgag gaggcgccgg agatgaccag cgcgggtggg    540

ctcctcgagc aggccgccgc ggtcgaggag gcctccgaca ccgccgcggc gaaccagttg    600

atgaacaatg tgccccaggc gctgcaacag ctggcccagc ccacgcaggg caccacgcct    660

tcttccaagc tgggtggcct gtggaagacg gtctcgccgc atcggtcgcc gatcagcaac    720

atggtgtcga tggccaacaa ccacatgtcg atgaccaact cgggtgtgtc gatgaccaac    780

accttgagct cgatgttgaa gggctttgct ccggcggcgg ccgcccaggc cgtgcaaacc    840

gcggcgcaaa acggggtccg ggcgatgagc tcgctgggca gctcgctggg ttcttcgggt    900

ctgggcggtg ggtggccgc caacttgggt cgggcggcct cggtcggttc gttgtcggtg    960

ccgcaggcct gggccgcggc caaccaggca gtcaccccgg cggcgcgggc gctgccgctg   1020

accagcctga ccagcgccgc ggaaagaggg cccgggcaga tgctgggcgg gctgccggtg   1080

gggcagatgg gcgccagggc cggtggtggg ctcagtggtg tgctgcgtgt tccgccgcga   1140

ccctatgtga tgccgcattc tccggcggcc ggctag                             1176
```

<210> SEQ ID NO 34
<211> LENGTH: 711
<212> TYPE: DNA
<213> ORGANISM: Mycobacterium tuberculosis

<400> SEQUENCE: 34

```
atgcggaccc ccagacgcca ctgccgtcgc atcgccgtcc tcgccgccgt tagcatcgcc     60

gccactgtcg ttgccggctg ctcgtcgggc tcgaagccaa gcggcggacc acttccggac    120
```

```
gcgaagccgc tggtcgagga ggccaccgcg cagaccaagg ctctcaagag cgcgcacatg    180

gtgctgacgg tcaacggcaa gatcccggga ctgtctctga agacgctgag cggcgatctc    240

accaccaacc ccaccgccgc gacgggaaac gtcaagctca cgctgggtgg gtctgatatc    300

gatgccgact tcgtggtgtt cgacgggatc ctgtacgcca ccctgacgcc caaccagtgg    360

agcgatttcg gtcccgccgc cgacatctac gaccccgccc aggtgctgaa tccggatacc    420

ggcctggcca acgtgctggc gaatttcgcc gacgcaaaag ccgaagggcg ggataccatc    480

aacggccaga acaccatccg catcagcggg aaggtatcgg cacaggcggt gaaccagata    540

gcgccgccgt tcaacgcgac gcagccggtg ccggcgaccg tctggattca ggagaccggc    600

gatcatcaac tggcacaggc ccagttggac cgcggctcgg gcaattccgt ccagatgacc    660

ttgtcgaaat ggggcgagaa ggtccaggtc acgaagcccc cggtgagctg a             711
```

```
<210> SEQ ID NO 35
<211> LENGTH: 1623
<212> TYPE: DNA
<213> ORGANISM: Mycobacterium tuberculosis

<400> SEQUENCE: 35

atggccaaga caattgcgta cgacgaagag gcccgtcgcg gcctcgagcg gggcttgaac     60

gccctcgccg atgcggtaaa ggtgacattg ggccccaagg gccgcaacgt cgtcctggaa    120

aagaagtggg gtgcccccac gatcaccaac gatggtgtgt ccatcgccaa ggagatcgag    180

ctggaggatc cgtacgagaa gatcggcgcc gagctggtca aagaggtagc caagaagacc    240

gatgacgtcg ccggtgacgg caccacgacg gccaccgtgc tggcccaggc gttggttcgc    300

gagggcctgc gcaacgtcgc ggccggcgcc aacccgctcg gtctcaaacg cggcatcgaa    360

aaggccgtgg agaaggtcac cgagaccctg ctcaagggcg ccaaggaggt cgagaccaag    420

gagcagattg cggccaccgc agcgatttcg gcgggtgacc agtccatcgg tgacctgatc    480

gccgaggcga tggacaaggt gggcaacgag ggcgtcatca ccgtcgagga gtccaacacc    540

tttgggctgc agctcgagct caccgagggt atgcggttcg acaagggcta catctcgggg    600

tacttcgtga ccgacccgga gcgtcaggag gcggtcctgg aggaccccta catcctgctg    660

gtcagctcca aggtgtccac tgtcaaggat ctgctgccgc tgctcgagaa ggtcatcgga    720

gccggtaagc cgctgctgat catcgccgag gacgtcgagg gcgaggcgct gtccaccctg    780

gtcgtcaaca agatccgcgg caccttcaag tcggtggcgg tcaaggctcc cggcttcggc    840

gaccgccgca aggcgatgct gcaggatatg gccattctca ccggtggtca ggtgatcagc    900

gaagaggtcg gcctgacgct ggagaacgcc gacctgtcgc tgctaggcaa ggcccgcaag    960

gtcgtggtca ccaaggacga gaccaccatc gtcgagggcg ccggtgacac cgacgccatc   1020

gccggacgag tggcccagat ccgccaggag atcgagaaca gcgactccga ctacgaccgt   1080

gagaagctgc aggagcggct ggccaagctg gccggtggtg tcgcggtgat caaggccggt   1140

gccgccaccg aggtcgaact caaggagcgc aagcaccgca tcgaggatgc ggttcgcaat   1200

gccaaggccg ccgtcgagga gggcatcgtc gccggtgggg gtgtgacgct gttgcaagcg   1260

gccccgaccc tggacgagct gaagctcgaa ggcgacgagg cgaccggcgc caacatcgtg   1320

aaggtggcgc tggaggcccc gctgaagcag atcgccttca actccgggct ggagccgggc   1380

gtggtggccg agaaggtgcg caacctgccg gctggccacg gactgaacgc tcagaccggt   1440

gtctacgagg atctgctcgc tgccggcgtt gctgacccgg tcaaggtgac ccgttcggcg   1500

ctgcagaatg cggcgtccat cgcggggctg ttcctgacca ccgaggccgt cgttgccgac   1560
```

aagccggaaa aggagaaggc ttccgttccc ggtggcggcg acatgggtgg catggatttc 1620
tga 1623

<210> SEQ ID NO 36
<211> LENGTH: 600
<212> TYPE: DNA
<213> ORGANISM: Mycobacterium tuberculosis

<400> SEQUENCE: 36
atggctgaaa actcgaacat tgatgacatc aaggctccgt tgcttgccgc gcttggagcg 60
gccgacctgg ccttggccac tgtcaacgag ttgatcacga acctgcgtga gcgtgcggag 120
gagactcgta cggacacccg cagccgggtc gaggagagcc gtgctcgcct gaccaagctg 180
caggaagatc tgcccgagca gctcaccgag ctgcgtgaga agttcaccgc cgaggagctg 240
cgtaaggccg ccgagggcta cctcgaggcc gcgactagcc ggtacaacga gctggtcgag 300
cgcggtgagg ccgctctaga gcggctgcgc agccagcaga gcttcgagga agtgtcggcg 360
cgcgccgaag gctacgtgga ccaggcggtg gagttgaccc aggaggcgtt gggtacggtc 420
gcatcgcaga cccgcgcggt cggtgagcgt gccgccaagc tggtcggcat cgagctgcct 480
aagaaggctg ctccggccaa gaaggccgct ccggccaaga aggccgctcc ggccaagaag 540
gcggcggcca agaaggcgcc cgcgaagaag gcggcggcca agaaggtcac ccagaagtag 600

<210> SEQ ID NO 37
<211> LENGTH: 1128
<212> TYPE: DNA
<213> ORGANISM: Mycobacterium tuberculosis

<400> SEQUENCE: 37
gtgacgcaaa ccggcaagcg tcagagacgc aaattcggtc gcatccgaca gttcaactcc 60
ggccgctggc aagccagcta caccggcccc gacggccgcg tgtacatcgc cccaaaacc 120 ttcaacgcca agatcgacgc cgaagcatgg ctcaccgacc gccgccgcga aatcgaccga 180
caactatggt ccccggcatc gggtcaggaa gaccgccccg gagccccatt cggtgagtac 240
gccgaaggat ggctgaagca gcgtggaatc aaggaccgca cccgcgccca ctatcgcaaa 300
ctgctggaca accacatcct ggccaccttc gctgacaccg acctacgcga catcaccccg 360
gccgccgtgc gccgctggta cgccaccacc gccgtgggca caccgaccat gcgggcacac 420
tcctacagct tgctgcgcgc aatcatgcag accgccttgg ccgacgacct gatcgactcc 480
aacccctgcc gcatctcagg cgcgtccacc gcccgccgcg tccacaagat caggcccgcc 540
accctcgacg agctggaaac catcaccaaa gccatgcccg acccctacca ggcgttcgtg 600
ctgatggcgg catggctggc catgcgctac ggcgagctga ccgaattacg ccgcaaagac 660
atcgacctgc acggcgaggt tgcgcgggtg cggcgggctg tcgttcgggt gggcgaaggc 720
ttcaaggtga cgacaccgaa aagcgatgcg ggagtgcgcg acataagtat cccgccacat 780
ctgatacccg ccatcgaaga ccaccttcac aaacacgtca accccggccg ggagtccctg 840
ctgttcccat cggtcaacga ccccaaccgt cacctagcac cctcggcgct gtaccgcatg 900
ttctacaagg cccgaaaagc cgccggccga ccagacttac gggtgcacga ccttcgacac 960
tccggcgccg tgttggctgc atccaccggc gccacactgg ccgaactgat gcagcggcta 1020
ggacacagca cagccggcgc cgcactccgc taccagcacg ccgccaaggg ccgggaccgc 1080
gaaatcgccg cactgttaag caaactggcc gagaaccagg agatgtga 1128

<210> SEQ ID NO 38
<211> LENGTH: 228
<212> TYPE: DNA
<213> ORGANISM: Mycobacterium tuberculosis

<400> SEQUENCE: 38
gtgatagcgg gcgtcgacca ggcgcttgca gcaacaggcc aggctagcca gcgggcggca 60
ggcgcatctg gtggggtcac cgtcggtgtc ggcgtgggca cggaacagag gaacctttcg 120
gtggttgcac cgagtcagtt cacatttagt tcacgcagcc cagattttgt ggatgaaacc 180
gcaggtcaat cgtggtgcgc gatactggga ttgaaccagt ttcactag 228

<210> SEQ ID NO 39
<211> LENGTH: 435
<212> TYPE: DNA
<213> ORGANISM: Mycobacterium tuberculosis

<400> SEQUENCE: 39
atggccacca cccttcccgt tcagcgccac ccgcggtccc tcttccccga gttttctgag 60
ctgttcgcgg ccttcccgtc attcgccgga ctccggccca ccttcgacac ccggttgatg 120
cggctggaag acgagatgaa agaggggcgc tacgaggtac gcgcggagct tcccggggtc 180
gaccccgaca aggacgtcga cattatggtc cgcgatggtc agctgaccat caaggccgag 240
cgcaccgagc agaaggactt cgacggtcgc tcggaattcg cgtacggttc cttcgttcgc 300
acggtgtcgc tgccggtagg tgctgacgag gacgacatta aggccaccta cgacaagggc 360
attcttactg tgtcggtggc ggtttcggaa gggaagccaa ccgaaaagca cattcagatc 420
cggtccacca actga 435

<210> SEQ ID NO 40
<211> LENGTH: 1224
<212> TYPE: DNA
<213> ORGANISM: Mycobacterium tuberculosis

<400> SEQUENCE: 40
atgagtggac gccaccgtaa gcccaccaca tccaacgtca gcgtcgccaa gatcgccttt 60
accggcgcag tactcggtgg cggcggcatc gccatggccg ctcaggcgac cgcggccacc 120
gacggggaat gggatcaggt ggcccgctgc gagtcgggcg gcaactggtc gatcaacacc 180
ggcaacggtt acctcggtgg cttgcagttc actcaaagca cctgggccgc acatggtggc 240
ggcgagttcg ccccgtcggc tcagctggcc agccgggagc agcagattgc cgtcggtgag 300
cgggtgctgg ccacccaggg tcgcggcgcc tggccggtgt gcggccgcgg gttatcgaac 360
gcaacacccc gcgaagtgct tcccgcttcg gcagcgatgg acgctccgtt ggacgcggcc 420
gcggtcaacg gcgaaccagc accgctggcc ccgccgcccg ccgacccggc gccacccgtg 480
gaacttgccg ctaacgacct gcccgcaccg ctgggtgaac ccctcccggc agctcccgcc 540
gacccggcac cacccgccga cctggcacca cccgcgcccg ccgacgtcgc gccacccgtg 600
gaacttgccg taaacgacct gcccgcaccg ctgggtgaac ccctcccggc agctcccgcc 660
gacccggcac cacccgccga cctggcacca cccgcgcccg ccgacctggc gccacccgcg 720
cccgccgacc tggcgccacc cgcgcccgcc gacctggcac cacccgtgga acttgccgta 780
aacgacctgc ccgcgccgct gggtgaaccc ctcccggcag ctcccgccga actggcgcca 840
cccgccgatc tggcacccgc gtccgccgac ctggcgccac ccgcgcccgc cgacctggcg 900
ccacccgcgc ccgccgaact ggcgccaccc gcgcccgccg acctggcacc acccgctgcg 960
gtgaacgagc aaaccgcgcc gggcgatcag cccgccacag ctccaggcgg cccggttggc 1020
cttgccaccg atttggaact ccccgagccc gaccccccaac cagctgacgc accgccgccc 1080
ggcgacgtca ccgaggcgcc cgccgaaacg ccccaagtct cgaacatcgc ctatacgaag 1140
aagctgtggc aggcgattcg ggcccaggac gtctgcggca acgatgcgct ggactcgctc 1200
gcacagccgt acgtcatcgg ctga 1224

<210> SEQ ID NO 41
<211> LENGTH: 1089
<212> TYPE: DNA
<213> ORGANISM: Mycobacterium tuberculosis

<400> SEQUENCE: 41
atgttgcgcc tggtagtcgg tgcgctgctg ctggtgttgg cgttcgccgg tggctatgcg 60
gtcgccgcat gcaaaacggt gacgttgacc gtcgacggaa ccgcgatgcg ggtgaccacg 120
atgaaatcgc gggtgatcga catcgtcgaa gagaacgggt tctcagtcga cgaccgcgac 180
gacctgtatc ccgcggccgg cgtgcaggtc catgacgccg acaccatcgt gctgcggcgt 240
agccgtccgc tgcagatctc gctggatggt cacgacgcta agcaggtgtg gacgaccgcg 300
tcgacggtgg acgaggcgct ggcccaactc gcgatgaccg acacggcgcc ggccgcggct 360
tctcgcgcca gccgcgtccc gctgtccggg atggcgctac cggtcgtcag cgccaagacg 420
gtgcagctca acgacggcgg gttggtgcgc acggtgcact tgccggcccc caatgtcgcg 480
gggctgctga gtgcggccgg cgtgccgctg ttgcaaagcg accacgtggt gcccgccgcg 540
acggccccga tcgtcgaagg catgcagatc caggtgaccc gcaatcggat caagaaggtc 600
accgagcggc tgccgctgcc gccgaacgcg cgtcgtgtcg aggacccgga gatgaacatg 660
agccgggagg tcgtcgaaga cccgggggtt ccggggaccc aggatgtgac gttcgcggta 720
gctgaggtca acggcgtcga gaccggccgt ttgcccgtcg ccaacgtcgt ggtgaccccg 780
gcccacgaag ccgtggtgcg ggtgggcacc aagcccggta ccgaggtgcc cccggtgatc 840
gacggaagca tctgggacgc gatcgccggc tgtgaggccg gtggcaactg ggcgatcaac 900
accggcaacg ggtattacgg tggtgtgcag tttgaccagg gcacctggga ggccaacggc 960
gggctgcggt atgcaccccg cgctgacctc gccacccgcg aagagcagat cgccgttgcc 1020
gaggtgaccc gactgcgtca aggttggggc gcctggccgg tatgtgctgc acgagcgggt 1080
gcgcgctga 1089

<210> SEQ ID NO 42
<211> LENGTH: 531
<212> TYPE: DNA
<213> ORGANISM: Mycobacterium tuberculosis

<400> SEQUENCE: 42
gtgcatcctt tgccggccga ccacggccgg tcgcggtgca atagacaccc gatctcacca 60
ctctctctaa tcggtaacgc ttcggccact tccggcgata tgtcgagcat gacaagaatc 120
gccaagccgc tcatcaagtc cgccatggcc gcaggactcg tcacggcatc catgtcgctc 180
tccaccgccg ttgcccacgc cggtcccagc ccgaactggg acgccgtcgc gcagtgcgaa 240
tccgggggca actgggcggc caacaccgga aacggcaaat acggcggact gcagttcaag 300
ccggccacct gggccgcatt cggcggtgtc ggcaacccag cagctgcctc tcgggaacaa 360
caaatcgcag ttgccaatcg ggttctcgcc gaacagggat tggacgcgtg gccgacgtgc 420
ggcgccgcct ctggccttcc gatcgcactg tggtcgaaac ccgcgcaggg catcaagcaa 480
atcatcaacg agatcatttg ggcaggcatt caggcaagta ttccgcgctg a 531

<210> SEQ ID NO 43
<211> LENGTH: 465
<212> TYPE: DNA
<213> ORGANISM: Mycobacterium tuberculosis

<400> SEQUENCE: 43
atgacaccgg gtttgcttac tactgcgggt gctggccgac cacgtgacag gtgcgccagg 60
atcgtatgca cggtgttcat cgaaaccgcc gttgtcgcga ccatgtttgt cgcgttgttg 120
ggtctgtcca ccatcagctc gaaagccgac gacatcgatt gggacgccat cgcgcaatgc 180
gaatccggcg gcaattgggc ggccaacacc ggtaacgggt tatacggtgg tctgcagatc 240
agccaggcga cgtgggattc caacggtggt gtcgggtcgc cggcggccgc gagtccccag 300
caacagatcg aggtcgcaga caacattatg aaaacccaag gcccgggtgc gtggccgaaa 360
tgtagttctt gtagtcaggg agacgcaccg ctgggctcgc tcacccacat cctgacgttc 420
ctcgcggccg agactggagg ttgttcgggg agcagggacg attga 465

<210> SEQ ID NO 44
<211> LENGTH: 519
<212> TYPE: DNA
<213> ORGANISM: Mycobacterium tuberculosis

<400> SEQUENCE: 44
ttgaagaacg cccgtacgac gctcatcgcc gccgcgattg ccgggacgtt ggtgaccacg 60
tcaccagccg gtatcgccaa tgccgacgac gcgggcttgg acccaaacgc cgcagccggc 120
ccggatgccg tgggctttga cccgaacctg ccgccggccc cggacgctgc acccgtcgat 180
actccgccgg ctccggagga cgcgggcttt gatcccaacc tccccccgcc gctggccccg 240
gacttcctgt ccccgcctgc ggaggaagcg cctcccgtgc ccgtggccta cagcgtgaac 300
tgggacgcga tcgcgcagtg cgagtccggt ggaaactggt cgatcaacac cggtaacggt 360
tactacggcg gcctgcggtt caccgccggc acctggcgtg ccaacggtgg ctcggggtcc 420
gcggccaacg cgagccggga ggagcagatc cgggtggctg agaacgtgct gcgttcgcag 480
ggtatccgcg cctggccggt ctgcggccgc cgcggctga 519

<210> SEQ ID NO 45
<211> LENGTH: 633
<212> TYPE: DNA
<213> ORGANISM: Mycobacterium tuberculosis

<400> SEQUENCE: 45
atgatcgcca caacccgcga tcgtgaagga gccaccatga tcacgtttag gctgcgcttg 60
ccgtgccgga cgatactgcg ggtgttcagc cgcaatccgc tggtgcgtgg gacggatcga 120
ctcgaggcgg tcgtcatgct gctggccgtc acggtctcgc tgctgactat cccgttcgcc 180
gccgcggccg gcaccgcagt ccaggattcc cgcagccacg tctatgccca ccaggcccag 240
acccgccatc ccgcaaccgc gaccgtgatc gatcacgagg gggtgatcga cagcaacacg 300
accgccacgt cagcgccgcc gcgcacgaag atcaccgtgc ctgcccgatg ggtcgtgaac 360
ggaatagaac gcagcggtga ggtcaacgcg aagccgggaa ccaaatccgg tgaccgcgtc 420
ggcatttggg tcgacagtgc cggtcagctg gtcgatgaac cagctccgcc ggcccgtgcc 480
attgcggatg cggccctggc cgccttggga ctctggttga gcgtcgccgc ggttgcgggc 540

```
gccctgctgg cgctcactcg ggcgattctg atccgcgttc gcaacgccag ttggcaacac    600

gacatcgaca gcctgttctg cacgcagcgg tga                                 633
```

<210> SEQ ID NO 46
<211> LENGTH: 1020
<212> TYPE: DNA
<213> ORGANISM: Mycobacterium tuberculosis

<400> SEQUENCE: 46

```
atgacggagc cagcggcgtg ggacgaaggc aagccgcgaa tcatcacttt gaccatgaac     60

cccgccttgg acatcacgac gagcgtcgac gtggtgcgcc cgaccgagaa aatgcgttgt    120

ggcgcacctc gctacgatcc cggcggcggc ggtatcaatg tcgcccgcat tgtgcatgtc    180

ctcggcggtt gctcgacagc actgttcccg gccggcgggt cgaccgggag cctgctgatg    240

gcgctgctcg gtgatgcggg agtgccattt cgcgtcattc cgatcgcggc ctcgacgcgg    300

gagagcttca cggtcaacga gtccaggacc gccaagcagt atcgtttcgt gcttccgggg    360

ccgtcgctga ccgtcgcgga gcaggagcaa tgcctcgacg aactgcgcgg tgcggcggct    420

tcggccgcct ttgtggtggc cagtggcagc ctgccgccag gtgtggctgc cgactactat    480

cagcgggttg ccgacatctg ccgccgatcg agcactccgc tgatcctgga tacatctggt    540

ggcgggttgc agcacatttc gtccggggtg tttcttctca aggcgagcgt gcgggaactg    600

cgcgagtgcg tcggatccga actgctgacc gagcccgaac aactggccgc cgcacacgaa    660

ctcattgacc gtgggcgcgc cgaggtcgtg gtggtctcgc ttggatctca gggcgcgcta    720

ttggccacac gacatgcgag ccatcgattt tcgtcgattc cgatgaccgc ggttagcggt    780

gtcggcgccg gcgacgcgat ggtggccgcg attaccgtgg gcctcagccg tggctggtcg    840

ctcatcaagt ccgttcgctt gggaaacgcg gcaggtgcag ccatgctgct gacgccaggc    900

accgcggcct gcaatcgcga cgatgtggag aggttcttcg agctggcggc cgaacccacc    960

gaagtcgggc aggatcaata cgtttggcac ccgatcgtta acccggaagc ctcgccatga   1020
```

<210> SEQ ID NO 47
<211> LENGTH: 996
<212> TYPE: DNA
<213> ORGANISM: Mycobacterium tuberculosis

<400> SEQUENCE: 47

```
atgccggaca ccatggtgac caccgatgtc atcaagagcg cggtgcagtt ggcctgccgc     60

gcaccgtcgc tccacaacag ccagccctgg cgctggatag ccgaggacca cacggttgcg    120

ctgttcctcg acaaggatcg ggtgctttac gcgaccgacc actccggccg ggaagcgctg    180

ctggggtgcg gcgccgtact cgaccacttt cgggtggcga tggcggccgc gggtaccacc    240

gccaatgtgg aacggtttcc caaccccaac gatcctttgc atctggcgtc aattgacttc    300

agcccggccg atttcgtcac cgagggccac cgtctaaggg cggatgcgat cctactgcgc    360

cgtaccgacc ggctgccttt cgccgagccg ccggattggg acttggtgga gtcgcagttg    420

cgcacgaccg tcaccgccga cacggtgcgc atcgacgtca tcgccgacga tatgcgtccc    480

gaactggcgg cggcgtccaa actcaccgaa tcgctgcggc tctacgattc gtcgtatcat    540

gccgaactct tttggtggac aggggctttt gagacttctg agggcatacc gcacagttca    600

ttggtatcgg cggccgaaag tgaccgggtc accttcggac gcgacttccc ggtcgtcgcc    660

aacaccgata ggcgcccgga gtttggccac gaccgctcta aggtcctggt gctctccacc    720
```

```
tacgacaacg aacgcgccag cctactgcgc tgcggcgaga tgctttccgc cgtattgctt    780

gacgccacca tggctgggct tgccacctgc acgctgaccc acatcaccga actgcacgcc    840

agccgagacc tggtcgcagc gctgattggg cagcccgcaa ctccgcaagc cttggttcgc    900

gtcggtctgg ccccggagat ggaagagccg ccaccggcaa cgcctcggcg accaatcgat    960

gaagtgtttc acgttcgggc taaggatcac cggtag                              996
```

<210> SEQ ID NO 48
<211> LENGTH: 432
<212> TYPE: DNA
<213> ORGANISM: Mycobacterium tuberculosis

<400> SEQUENCE: 48

```
atgaccaccg cacgcgacat catgaacgca ggtgtgacct gtgttggcga acacgagacg     60

ctaaccgctg ccgctcaata catgcgtgag cacgacatcg gcgcgttgcc gatctgcggg    120

gacgacgacc ggctgcacgg catgctcacc gaccgcgaca ttgtgatcaa aggcctggct    180

gcgggcctag acccgaatac cgccacggct ggcgagttgg cccgggacag catctactac    240

gtcgatgcga acgcaagcat ccaggagatg ctcaacgtca tggaagaaca tcaggtccgc    300

cgtgttccgg tcatctcaga gcaccgcttg gtcggaatcg tcaccgaagc cgacatcgcc    360

cgacacctgc ccgagcacgc cattgtgcag ttcgtcaagg caatctgctc gcccatggcc    420

ctcgccagct ag                                                        432
```

<210> SEQ ID NO 49
<211> LENGTH: 1242
<212> TYPE: DNA
<213> ORGANISM: Mycobacterium tuberculosis

<400> SEQUENCE: 49

```
atggcaagtt ctgcgagcga cggcacccac gaacgctcgg cttttcgcct gagtccaccg     60

gtcttgagcg gcgccatggg accgttcatg cacaccggtc tgtacgtcgc tcaatcgtgg    120

cgcgactatc tgggtcaaca gcccgataaa ctgccgatcg cacggcccac tattgcctta    180

gcggcgcaag cctttcgaga cgaaatcgtc ctgctgggcc tcaaggcacg acgtccggtc    240

agcaatcatc gagtgttcga gcgcatcagc caagaagtgg ccgctggact ggagttctat    300

gggaatcgca gatggctgga gaagcctagc ggattttttg cccagccccc accgctcacc    360

gaggtcgcgg tccgaaaggt caaggaccgc agacgctcct tttatcgcat cttcttcgac    420

agtgggttta cgccgcatcc gggtgaaccg ggcagccaac ggtggctctc atacactgcg    480

aacaatcgcg agtacgccct gttactgcgg cacccagagc cgcgtccctg gctggtttgt    540

gtacacggca ccgagatggg cagggccccg ttggatctcg cggtgttccg cgcctggaag    600

ctgcatgacg aactcggcct gaacattgtc atgccggttc ttccgatgca tggtccccgc    660

gggcaaggtc tgccgaaggg cgccgttttt cccggagaag atgttctcga cgatgtgcat    720

gggacggctc aagcggtgtg ggatatccgg cggctgttgt cctggatacg atcgcaggag    780

gaggagtcgc tgatcgggtt gaacggtctc tcgctgggcg gctacatcgc gtcattggtc    840

gccagcctcg aagaaggtct cgcctgcgcg attctcggtg tcccagtggc tgatctgatc    900

gagttgttgg gccgccactg cggtcttcgg cacaaagacc cccgccgcca caccgtcaag    960

atggccgaac cgatcggccg aatgatctcg ccgctctcac ttacgccact ggtgcccatg   1020

ccgggccgct ttatctacgc gggcattgcc gaccgactcg tgcatccacg cgaacaggtg   1080

actcgcctct gggagcactg gggcaaaccc gaaatcgtgt ggtatccagg cggtcacact   1140
```

```
ggcttcttcc agtcgcggcc ggtacgacgg tttgtccagg ctgcgctgga gcagtcgggc   1200

ctgttggacg cgccacggac acagcgcgac cgttccgcct aa                      1242


<210> SEQ ID NO 50
<211> LENGTH: 363
<212> TYPE: DNA
<213> ORGANISM: Mycobacterium tuberculosis

<400> SEQUENCE: 50

atgtccacgc aacgaccgag gcactccggt attcgggctg ttggccccta cgcatgggcc     60

ggccgatgtg gtcggatagg caggtggggg gtgcaccagg aggcgatgat gaatctagcg    120

atatggcacc cgcgcaaggt gcaatccgcc accatctatc aggtgaccga tcgctcgcac    180

gacgggcgca cagcacgggt gcctggtgac gagatcacta gcaccgtgtc cggttggttg    240

tcggagttgg gcacccaaag cccgttggcc gatgagcttg cgcgtgcggt gcggatcggc    300

gactggcccg ctgcgtacgc aatcggtgag cacctgtccg ttgagattgc cgttgcggtc    360

taa                                                                  363


<210> SEQ ID NO 51
<211> LENGTH: 1119
<212> TYPE: DNA
<213> ORGANISM: Artificial sequence
<220> FEATURE:
<223> OTHER INFORMATION: Synthetic sequence

<400> SEQUENCE: 51

atggacgcca tgaagagggg cctgtgctgc gtgctgctgc tgtgtggcgc cgtgttcgtg     60

tcccccagcc aggaaatcca cgcccggttc agacggggca gcatgcagct ggtggacaga    120

gtcagaggcg ccgtgaccgg catgagcaga cggctggtcg tgggagctgt cggagccgct    180

ctggtgtctg gactcgtggg agccgtgggc ggaacagcta cagccggcgc tttcagcaga    240

cccggcctgc ccgtggaata tctgcaggtc cccagcccca gcatgggccg ggacatcaag    300

gtgcagttcc agtctggcgg agccaacagc cctgctctgt acctgctgga cggcctgaga    360

gcccaggacg acttcagcgg ctgggacatc aacacccccg ccttcgagtg gtacgaccag    420

agcggcctgt ctgtggtcat gcctgtgggc ggccagagca gcttctacag cgactggtat    480

cagcccgctt gtggcaaggc cggctgccag acctacaagt gggagacatt cctgaccagc    540

gagctgcccg gctggctgca ggccaacaga cacgtgaagc ccaccggctc tgccgtcgtg    600

ggcctgtcta tggctgccag ctctgccctg accctggcca tctaccaccc ccagcagttc    660

gtgtacgctg gcgccatgtc tggcctgctg gatccttctc aggccatggg acccaccctg    720

atcggactgg ctatgggaga tgccggcgga tacaaggcca gcgacatgtg ggggccctaaa    780

gaggaccccg cctggcagag aaacgacccc ctgctgaacg tgggcaagct gatcgccaac    840

aacaccagag tgtgggtgta ctgcggcaac ggcaagctga gcgacctggg cggcaacaac    900

ctgcccgcca agttcctgga aggcttcgtg cggaccagca acatcaagtt ccaggacgcc    960

tacaacgctg gcggcggaca caacggcgtg ttcgacttcc ccgacagcgg cacccacagc   1020

tgggagtatt ggggagccca gctgaatgcc atgaagcccg acctgcagag agccctgggc   1080

gccaccccta atactggacc tgctcctcag ggcgcatga                         1119


<210> SEQ ID NO 52
<211> LENGTH: 372
<212> TYPE: PRT
```

```
<213> ORGANISM: Mycobacterium tuberculosis

<400> SEQUENCE: 52

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

Gly Ser Met Gln Leu Val Asp Arg Val Arg Gly Ala Val Thr Gly Met
        35                  40                  45

Ser Arg Arg Leu Val Val Gly Ala Val Gly Ala Ala Leu Val Ser Gly
    50                  55                  60

Leu Val Gly Ala Val Gly Gly Thr Ala Thr Ala Gly Ala Phe Ser Arg
65                  70                  75                  80

Pro Gly Leu Pro Val Glu Tyr Leu Gln Val Pro Ser Pro Ser Met Gly
                85                  90                  95

Arg Asp Ile Lys Val Gln Phe Gln Ser Gly Gly Ala Asn Ser Pro Ala
            100                 105                 110

Leu Tyr Leu Leu Asp Gly Leu Arg Ala Gln Asp Asp Phe Ser Gly Trp
        115                 120                 125

Asp Ile Asn Thr Pro Ala Phe Glu Trp Tyr Asp Gln Ser Gly Leu Ser
    130                 135                 140

Val Val Met Pro Val Gly Gly Gln Ser Ser Phe Tyr Ser Asp Trp Tyr
145                 150                 155                 160

Gln Pro Ala Cys Gly Lys Ala Gly Cys Gln Thr Tyr Lys Trp Glu Thr
                165                 170                 175

Phe Leu Thr Ser Glu Leu Pro Gly Trp Leu Gln Ala Asn Arg His Val
            180                 185                 190

Lys Pro Thr Gly Ser Ala Val Val Gly Leu Ser Met Ala Ala Ser Ser
        195                 200                 205

Ala Leu Thr Leu Ala Ile Tyr His Pro Gln Gln Phe Val Tyr Ala Gly
    210                 215                 220

Ala Met Ser Gly Leu Leu Asp Pro Ser Gln Ala Met Gly Pro Thr Leu
225                 230                 235                 240

Ile Gly Leu Ala Met Gly Asp Ala Gly Gly Tyr Lys Ala Ser Asp Met
                245                 250                 255

Trp Gly Pro Lys Glu Asp Pro Ala Trp Gln Arg Asn Asp Pro Leu Leu
            260                 265                 270

Asn Val Gly Lys Leu Ile Ala Asn Asn Thr Arg Val Trp Val Tyr Cys
        275                 280                 285

Gly Asn Gly Lys Leu Ser Asp Leu Gly Gly Asn Asn Leu Pro Ala Lys
    290                 295                 300

Phe Leu Glu Gly Phe Val Arg Thr Ser Asn Ile Lys Phe Gln Asp Ala
305                 310                 315                 320

Tyr Asn Ala Gly Gly Gly His Asn Gly Val Phe Asp Phe Pro Asp Ser
                325                 330                 335

Gly Thr His Ser Trp Glu Tyr Trp Gly Ala Gln Leu Asn Ala Met Lys
            340                 345                 350

Pro Asp Leu Gln Arg Ala Leu Gly Ala Thr Pro Asn Thr Gly Pro Ala
        355                 360                 365

Pro Gln Gly Ala
    370

<210> SEQ ID NO 53
<211> LENGTH: 168
```

<212> TYPE: DNA
<213> ORGANISM: Artificial sequence
<220> FEATURE:
<223> OTHER INFORMATION: Synthetic sequence

<400> SEQUENCE: 53
aagaagcagg gcgacgccga cgtgtgtggc gaggtggcct acatccagag cgtggtgtcc 60
gactgccacg tgccaaccgc cgagctgcgg accctgctgg aaatccggaa gctgttcctg 120
gaaatccaga aactgaaggt ggaactgcag ggcctgagca aagagtga 168

<210> SEQ ID NO 54
<211> LENGTH: 1245
<212> TYPE: DNA
<213> ORGANISM: Artificial sequence
<220> FEATURE:
<223> OTHER INFORMATION: Synthetic sequence

<400> SEQUENCE: 54
atggacgcca tgaagagggg cctgtgctgc gtgctgctgc tgtgtggcgc cgtgttcgtg 60
tcccccagcc aggaaatcca cgcccggttc agacggggca gcatgcagct ggtggacaga 120
gtcagaggcg ccgtgaccgg catgagcaga cggctggtcg tgggagctgt cggagccgct 180
ctggtgtctg gactcgtggg agccgtgggc ggaacagcta cagccggcgc tttcagcaga 240
cccggcctgc ccgtggaata tctgcaggtc cccagcccca gcatgggccg ggacatcaag 300
gtgcagttcc agtctggcgg agccaacagc cctgctctgt acctgctgga cggcctgaga 360
gcccaggacg acttcagcgg ctgggacatc aacacccccg ccttcgagtg gtacgaccag 420
agcggcctgt ctgtggtcat gcctgtgggc ggccagagca gcttctacag cgactggtat 480
cagcccgctt gtggcaaggc cggctgccag acctacaagt gggagacatt cctgaccagc 540
gagctgcccg gctggctgca ggccaacaga cacgtgaagc ccaccggctc tgccgtcgtg 600
ggcctgtcta tggctgccag ctctgccctg accctggcca tctaccaccc ccagcagttc 660
gtgtacgctg gcgccatgtc tggcctgctg gatccttctc aggccatggg acccaccctg 720
atcggactgg ctatgggaga tgccggcgga tacaaggcca gcgacatgtg gggccctaaa 780
gaggaccccg cctggcagag aaacgacccc ctgctgaacg tgggcaagct gatcgccaac 840
aacaccagag tgtgggtgta ctgcggcaac ggcaagctga gcgacctggg cggcaacaac 900
ctgcccgcca agttcctgga aggcttcgtg cggaccagca acatcaagtt ccaggacgcc 960
tacaacgctg gcggcggaca caacggcgtg ttcgacttcc ccgacagcgg cacccacagc 1020
tgggagtatt ggggagccca gctgaatgcc atgaagcccg acctgcagag aggcagcaag 1080
aagcagggcg acgccgacgt gtgtggcgag gtggcctaca tccagagcgt ggtgtccgac 1140
tgccacgtgc caaccgccga gctgcggacc ctgctggaaa tccggaagct gttcctggaa 1200
atccagaaac tgaaggtgga actgcagggc ctgagcaaag agtga 1245

<210> SEQ ID NO 55
<211> LENGTH: 414
<212> TYPE: PRT
<213> ORGANISM: Artificial sequence
<220> FEATURE:
<223> OTHER INFORMATION: Synthetic sequence

<400> SEQUENCE: 55

Met Asp Ala Met Lys Arg Gly Leu Cys Cys Val Leu Leu Leu Cys Gly
1 5 10 15

Ala Val Phe Val Ser Pro Ser Gln Glu Ile His Ala Arg Phe Arg Arg

```
            20                  25                  30

Gly Ser Met Gln Leu Val Asp Arg Val Arg Gly Ala Val Thr Gly Met
        35                  40                  45

Ser Arg Arg Leu Val Val Gly Ala Val Gly Ala Ala Leu Val Ser Gly
    50                  55                  60

Leu Val Gly Ala Val Gly Gly Thr Ala Thr Ala Gly Ala Phe Ser Arg
65                  70                  75                  80

Pro Gly Leu Pro Val Glu Tyr Leu Gln Val Pro Ser Pro Ser Met Gly
                85                  90                  95

Arg Asp Ile Lys Val Gln Phe Gln Ser Gly Gly Ala Asn Ser Pro Ala
            100                 105                 110

Leu Tyr Leu Leu Asp Gly Leu Arg Ala Gln Asp Asp Phe Ser Gly Trp
        115                 120                 125

Asp Ile Asn Thr Pro Ala Phe Glu Trp Tyr Asp Gln Ser Gly Leu Ser
    130                 135                 140

Val Val Met Pro Val Gly Gly Gln Ser Ser Phe Tyr Ser Asp Trp Tyr
145                 150                 155                 160

Gln Pro Ala Cys Gly Lys Ala Gly Cys Gln Thr Tyr Lys Trp Glu Thr
                165                 170                 175

Phe Leu Thr Ser Glu Leu Pro Gly Trp Leu Gln Ala Asn Arg His Val
            180                 185                 190

Lys Pro Thr Gly Ser Ala Val Val Gly Leu Ser Met Ala Ala Ser Ser
        195                 200                 205

Ala Leu Thr Leu Ala Ile Tyr His Pro Gln Gln Phe Val Tyr Ala Gly
    210                 215                 220

Ala Met Ser Gly Leu Leu Asp Pro Ser Gln Ala Met Gly Pro Thr Leu
225                 230                 235                 240

Ile Gly Leu Ala Met Gly Asp Ala Gly Gly Tyr Lys Ala Ser Asp Met
                245                 250                 255

Trp Gly Pro Lys Glu Asp Pro Ala Trp Gln Arg Asn Asp Pro Leu Leu
            260                 265                 270

Asn Val Gly Lys Leu Ile Ala Asn Asn Thr Arg Val Trp Val Tyr Cys
        275                 280                 285

Gly Asn Gly Lys Leu Ser Asp Leu Gly Gly Asn Asn Leu Pro Ala Lys
    290                 295                 300

Phe Leu Glu Gly Phe Val Arg Thr Ser Asn Ile Lys Phe Gln Asp Ala
305                 310                 315                 320

Tyr Asn Ala Gly Gly Gly His Asn Gly Val Phe Asp Phe Pro Asp Ser
                325                 330                 335

Gly Thr His Ser Trp Glu Tyr Trp Gly Ala Gln Leu Asn Ala Met Lys
            340                 345                 350

Pro Asp Leu Gln Arg Gly Ser Lys Lys Gln Gly Asp Ala Asp Val Cys
        355                 360                 365

Gly Glu Val Ala Tyr Ile Gln Ser Val Val Ser Asp Cys His Val Pro
    370                 375                 380

Thr Ala Glu Leu Arg Thr Leu Leu Glu Ile Arg Lys Leu Phe Leu Glu
385                 390                 395                 400

Ile Gln Lys Leu Lys Val Glu Leu Gln Gly Leu Ser Lys Glu
                405                 410
```

<210> SEQ ID NO 56
<211> LENGTH: 1017
<212> TYPE: DNA
<213> ORGANISM: Artificial sequence
<220> FEATURE:
<223> OTHER INFORMATION: Synthetic sequence

<400> SEQUENCE: 56
atgcagctgg tggacagagt cagaggcgcc gtgaccggca tgagcagacg gctggtcgtg 60
ggagctgtcg gagccgctct ggtgtctgga ctcgtgggag ccgtgggcgg aacagctaca 120
gccggcgctt tcagcagacc cggcctgccc gtggaatatc tgcaggtccc cagccccagc 180
atgggccggg acatcaaggt gcagttccag tctggcggag ccaacagccc tgctctgtac 240
ctgctggacg gcctgagagc ccaggacgac ttcagcggct gggacatcaa cacccccgcc 300
ttcgagtggt acgaccagag cggcctgtct gtggtcatgc ctgtgggcgg ccagagcagc 360
ttctacagcg actggtatca gcccgcttgt ggcaaggccg gctgccagac ctacaagtgg 420
gagacattcc tgaccagcga gctgcccggc tggctgcagg ccaacagaca cgtgaagccc 480
accggctctg ccgtcgtggg cctgtctatg gctgccagct ctgccctgac cctggccatc 540
taccaccccc agcagttcgt gtacgctggc gccatgtctg gcctgctgga tccttctcag 600
gccatgggac ccaccctgat cggactggct atgggagatg ccggcggata caaggccagc 660
gacatgtggg gccctaaaga ggacccogcc tggcagagaa acgacccccct gctgaacgtg 720 ggcaagctga tcgccaacaa caccagagtg tgggtgtact gcggcaacgg caagctgagc 780
gacctgggcg gcaacaacct gcccgccaag ttcctggaag gcttcgtgcg gaccagcaac 840
atcaagttcc aggacgccta caacgctggc ggcggacaca acggcgtgtt cgacttcccc 900
gacagcggca cccacagctg ggagtattgg ggagcccagc tgaatgccat gaagcccgac 960
ctgcagagag ccctgggcgc cacccctaat actggacctg ctcctcaggg cgcatga 1017

<210> SEQ ID NO 57
<211> LENGTH: 47
<212> TYPE: DNA
<213> ORGANISM: Artificial Sequence
<220> FEATURE:
<223> OTHER INFORMATION: Synthetic sequence

<400> SEQUENCE: 57
gaagcccgac ctgcaacgtg gatccaagaa gcaaggtgat gctgatg 47

<210> SEQ ID NO 58
<211> LENGTH: 57
<212> TYPE: DNA
<213> ORGANISM: Artificial Sequence
<220> FEATURE:
<223> OTHER INFORMATION: Synthetic sequence

<400> SEQUENCE: 58
agggccctct agatgcatgc tcgagcggcc gcttattact ccttgctcag tccttgc 57

<210> SEQ ID NO 59
<211> LENGTH: 35
<212> TYPE: DNA
<213> ORGANISM: Artificial Sequence
<220> FEATURE:
<223> OTHER INFORMATION: Synthetic sequence

<400> SEQUENCE: 59
ggggcatatg ttttcccggc cgggcttgcc ggtgg 35

<210> SEQ ID NO 60
<211> LENGTH: 37
<212> TYPE: DNA

```
<213> ORGANISM: Artificial Sequence
<220> FEATURE:
<223> OTHER INFORMATION: Synthetic sequence

<400> SEQUENCE: 60

ggggggatcc ggcgccctgg ggcgcgggcc cggtgtt                              37
```

MYCOBACTERIAL VACCINES

RELATED APPLICATION DATA

This application is a National Stage Application under 35 U.S.C. 371 of co-pending PCT application PCT/GB2010/051741 designating the U.S.and filed Oct. 15, 2010; which claims the benefit of GB patent application Ser. No. 0918154.6 and filed Oct. 16, 2009each of which are hereby incorporated by reference in their entireties.

The present invention relates to polynucleotides and fusion proteins, to vectors, to immunogenic compositions and to methods and uses thereof for the treatment or prevention of mycobacterial infections, particularly in primates such as man.

*Mycobacterium tuberculosis* (MTB) and closely related species make up a small group of mycobacteria known as the Mycobacterium tuberculosis complex (MTC). This group comprises five distinct species: *M. tuberculosis*, *M microti*, *M bovis*, *M. canetti*, and *M. africanum*.

As the aetiological agent of tuberculosis infection (TB), *Mycobacterium tuberculosis* (*M. tuberculosis*) is the leading cause of death by bacterial infectious disease worldwide—latent infection affecting as much as one third of the world's population. The World Health Organisation (WHO) estimates that nearly nine million new cases of TB, and nearly two million deaths, occur globally each year. The largest number of new TB cases in 2005 occurred in South-East Asia (34% of incident cases globally), and the estimated incidence rate in sub-Saharan Africa is nearly 350 cases per 100,000 population. However, TB infection is not limited to the developing world: the UK has seen a resurgence of tuberculosis since the late 1980s and there are currently over 8000 new cases each year—a rate of 14.0 per 100,000 population.

Other mycobacteria are also pathogenic in man and animals, for example *M. avium* subsp. *paratuberculosis* which causes Johne's disease in ruminants, *M. bovis* which causes tuberculosis in cattle, *M. avium* and *M. intracellulare* which cause tuberculosis in immunocompromised patients (eg. AIDS patients, and bone marrow transplant patients) and *M. leprae* which causes leprosy in humans. Another important mycobacterial species is *M. vaccae*.

The effectiveness of vaccine prevention against *M. tuberculosis* has varied widely. The current *M. tuberculosis* vaccine, BCG, is an attenuated strain of *M. bovis*. It is effective against severe complications of TB in children, but it varies greatly in its effectiveness in adults, particularly across ethnic groups. The efficacy of BCG appears to decline with age and as such it is not effective at preventing disease in adults, particularly in TB endemic areas. BCG vaccination has been used to prevent tuberculous meningitis and helps prevent the spread of *M. tuberculosis* to extra-pulmonary sites, but does not prevent infection. The limited efficacy of BCG and the global prevalence of TB has led to an international effort to generate new, more effective vaccines.

A number of tuberculosis subunit vaccines have been shown to induce strong immune responses with some degree of protection, however the level of efficacy when used alone is no greater than that conferred by BCG and these have been ruled out as replacements for BCG.

Most vaccines work by inducing antibodies that are protective against infection by the relevant pathogen. Adjuvants are sometimes used to accelerate, prolong, or enhance antigen-specific immune responses when used in combination with specific vaccine antigens. Commonly used immunological adjuvants include oils and aluminum salts.

One such adjuvant is the complement 4 binding protein (C4bp), which is a regulator of the complement pathway. C4bp is a large glycoprotein and has been isolated from a number of mammalian species. In humans, C4bp exists in the plasma in several isoforms, the main isoform being a heptamer consisting of seven α-chains and one β-chain linked together at the C-terminus. Because of its' "spider or octopus-like" structure and predicted long serum half-life, fusion of proteins to C4bp has been proposed as a delivery platform to enhance bioactivity and immunogenicity (WO91/11461). WO91/11461 is incorporated herein by reference thereto. Additional examples of C4bp-based vaccine approaches are described in EP 1795540, WO 08/122,817 and WO 05/014654, each of which is incorporated herein by reference thereto.

A different approach being explored to generate an immune response is to clone an antigen or epitope of interest into a vector. Plasmids as well as viral vectors are commonly used. For example, a modified vaccinia Ankara virus (MVA) expressing the *M. tuberculosis* antigen 85A has shown some ability to boost the BCG response and protection in a number of animal models. Clinical trials have shown the substantial capacity of MVA85A to boost the immune response to BCG (McShane et al. Nat Med 10, 1240; 2004).

In view of the increasing threat and global prevalence of mycobacterial infection, alternative/improved methods and compositions are required for prevention and treatment of mycobacterial infection.

In particular, whilst initial clinical data in rodents have provided some optimism, corresponding efficacy in primates (notably in humans) has been disappointing to date.

Similarly, whilst BCG vaccine remains the global "gold standard", efforts to provide improved protection by way of booster vaccines has proven disappointing to date, especially in animals (notably in primates such as humans).

The present invention solves one or more of the above problems.

The present invention provides a polynucleotide sequence encoding a fusion protein comprising first and second domains, wherein the first domain of the fusion protein comprises an amino acid sequence having at least 70% sequence identity to the amino acid sequence of SEQ ID NO: 1, or a fragment thereof comprising at least 20 consecutive amino acids thereof; and wherein the second domain of the fusion protein comprises a mycobacterial antigen or an antigenic fragment thereof.

The first domain of the present invention comprises a hybrid non-complement control protein (CCP)/oligomerization domain of a C4bp protein. It is most surprising that said hybrid C4bp-antigen fusion provides improves protection against mycobacterial infection, not only in animals such as rodents, but also in primates. This represents a major scientific breakthrough as many earlier studies, whilst encouraging in rodents have failed to deliver meaningful efficacy in primates.

The main C4bp isoform in humans consists of seven α-chains and one β-chain linked together at the C-terminus. The last exon of the α-chain encodes the only non-CCP (complement control protein) domain in the alpha chain. This domain is sufficient for the oligomerization of the seven C4bp alpha chains. The oligomerisation effect of this domain has been extended to other fused poly-peptides/proteins. Fusion of a malarial antigen to the oligomerisation domain of the mouse C4bp has recently been shown to enhance the induction of specific antibodies when administered as a fusion protein.

In one embodiment, the first domain comprises an amino acid sequence having at least 70% (such as at least 75, 80, 82, 84, 86, 88, 90, 92, 94, 96, 98, 99 or 100%) amino acid sequence identity to the amino acid sequence of SEQ ID NO: 1, or a fragment thereof comprising at least 20 consecutive amino acids thereof.

In one embodiment, the first domain consists of an amino acid sequence having at least 70% (such as at least 75, 80, 82, 84, 86, 88, 90, 92, 94, 96, 98, 99 or 100%) amino acid sequence identity to the amino acid sequence of SEQ ID NO: 1, or a fragment thereof comprising at least 20 consecutive amino acids thereof.

In one embodiment, the amino acid sequence identity exists over a region of the amino acid sequences that is at least 20 consecutive amino acid residues in length (eg. at least 25, 28, 30 35, 40, 45, 50, or 55 consecutive amino acid residues in length).

Conventional methods for determining amino acid sequence identity are discussed in more detail later in the specification.

In the context of the first domain, a fragment comprises (or consists of) at least 20 consecutive amino acid residues of said amino acid sequence (eg. at least 25, 28, 30, 35, 40, 42, 44, 46, 48, 50, 52 or 54 consecutive amino acid residues thereof).

In one embodiment, in the context of the first domain, a fragment of an amino acid sequence has a sequence length that is at least 40%, 50%, 60%, 70%, 80%, or 90% of that of the sequence of the full-length amino acid sequence.

SEQ ID NO: 1 (also referred to as IMX313) consists of 55 amino acid residues. Variants of SEQ ID NO: 1 are encompassed by the present invention and may include amino acid sequences with one or more amino acid substitutions, deletions or insertions. Substitutions are particularly envisaged, as are N- and C-terminal deletions. Substitutions include conservative substitutions. Conventional methods for selecting conservative substitutions and making deletions and insertions are discussed in more detail later in the specification.

Thus, in one embodiment, a variant of SEQ ID NO: 1 comprises an N-terminal deletion of at least 1 consecutive amino acid residues (eg. at least 2, 3, 4, 5, 6, 7, 8, 9, 10 consecutive amino acid residues) in length.

In one embodiment, a variant of SEQ ID NO: 1 comprises a C-terminal deletion of at least 1 consecutive amino acid residues (eg. at least 2, 3, 4, 5, 6, 7, 8, 9, 10 consecutive amino acid residues) in length.

In one embodiment, a variant of SEQ ID NO:1 retains at least 1 (eg. at least 2, 3, 4, 5, 6, 7, 8, 9, 10, 11, 12, 13, 14, 15, 16, 17, 18, 19, 20, 21, 22, 23, 24, 25, 26) of the following residues of SEQ ID NO: 1: Ala6; Glu11; Ala13; Asp21; Cys22; Pro25; Ala27; Glu28; Leu29; Arg30; Thr31; Leu32; Leu33; Glu34; Ile35; Lys37; Leu38; Leu40; Glu41; Ile42; Gln43; Lys44; Leu45; Glu48; Leu49; or Gln50.

In one embodiment, the first domain retains the amino acid motif "AELR" (i.e. positions 27-30 of SEQ ID NO: 1. Said motif may include one or more conservative amino acid substitutions, for example 1, 2, 3, or 4 conservative amino acid substitutions).

The second domain of the fusion protein comprises a mycobacterial antigen, or an antigenic fragment of said mycobacterial antigen.

As used herein, the term "mycobacterial" or "mycobacterium" embraces the species *M. phlei, M. smegmatis, M. africanum, M. canetti, M. fortuitum, M. marinum, M. ulcerans, M. tuberculosis, M. bovis, M. microti, M. avium, M. paratuberculosis, M. leprae, M. lepraemurium, M. intracellulare, M. scrofulaceum, M. xenopi, M. genavense, M. kansasii, M. simiae, M. szulgai, M. haemophilum, M. asiaticum, M. malmoense, M. vaccae*, and *M. shimoidei*. Of particular interest are the members of the MTC, such as *M. tuberculosis*.

The term antigen or antigenic fragment means any peptide-based sequence that can be recognized by the immune system and/or that stimulates a cell mediated immune response and/or stimulates the generation of antibodies.

The positive immunogenicity results achieved with polynucleotides of the invention (see Example 3 and FIGS. 1-6 below) are most surprising and unexpected. For example, in contrast to the present invention, fusions of SEQ ID NO: 1 with malarial antigens did not result in an enhanced immune response (see Example 3 and FIG. 7 below). Even more surprising is that the positive immunogenicity towards the mycobacterial antigen observed in mice was also observed in primates.

In one embodiment, the mycobacterial antigen or antigenic fragment thereof provides a cell mediated response to infection involving T cells (CD4+ and/or CD8+ T cells) and/or the ability to respond with Th1-type cytokines such as IFN-γ. In one embodiment, a mycobacterial antigen induces IFN-γ-secreting cells (eg. predominantly CD4+ T cells). In this regard, recent studies suggest that T cell immune responses (such as in the lung mucosa) may be critical for protection against pulmonary mycobacterial disease.

In one embodiment, the mycobacterial antigen or antigenic fragment thereof provides protection (such as long term protection) against challenge by mycobacteria such as *M. tuberculosis*.

By way of example, the mycobacterial antigen or antigenic fragment thereof may induce 'memory T cells', which can continue to stimulate protective immunity in the long term (eg. for decades). Memory immune responses have been attributed to the reactivation of long-lived, antigen-specific T lymphocytes that arise directly from differentiated effector T-cells and persist in a quiescent state. Memory T cells are heterogeneous; at least two subsets have been identified, having different migratory capacity and effector function. Memory T cells of the first subset are known as 'effector memory T cells' (TEM) because they resemble the effector T cells generated in the primary response, in that they lack the lymph node-homing receptors for migration into inflamed tissues. Upon re-encounter with antigen, the TEM rapidly produce IFN-γ or IL-4, or release pre-stored perforin. Memory T cells of the second subset (known as 'central memory cells' (TCM)) express L-selectin and CCR7 and lack immediate effector function. The TCM have a low activation threshold and proliferate and differentiate to effectors when re-stimulated in secondary lymphoid organs.

In one embodiment, the mycobacterial antigen or antigenic fragment thereof provides an antibody response (eg. a neutralizing antibody response) to mycobacterial (eg. *M. tuberculosis*) infection.

In one embodiment the second domain comprises a mycobacterial antigen selected from 85A/Rv3804c, 85B/Rv1886c, 85C/Rv0129c, ESAT6/Rv3875, TB10.4/Rv0288, Rv0125, PPE18/Rv1196, P27/Rv1411c, HSP65/Rv0440, HBHA/Rv0475, Rv2659c, Rv2660c, HspX/Rv2031c, RPFA/Rv0867c, RPFB/Rv1009, RPFC/Rv1884c, RPFD/Rv2389c, RPFE/Rv2450c, Rv1733c, Rv2029c, Rv2032, Rv2626c, Rv2627c, Rv2628, Rv0111, Rv1806/1807, Rv0198, or Rv3812 or antigenic fragments thereof.

In one embodiment, the second domain comprises an amino acid sequence having at least 70% (such as at least 75, 80, 82, 84, 86, 88, 90, 92, 94, 96, 98, 99 or 100%) amino acid sequence identity to an amino acid sequence selected from SEQ ID NOs: 3-26 or 52, or a fragment thereof comprising at least 10 consecutive amino acids thereof.

In one embodiment, the second domain consists of an amino acid sequence having at least 70% (such as at least 75, 80, 82, 84, 86, 88, 90, 92, 94, 96, 98, 99 or 100%) amino acid sequence identity to an amino acid sequence selected from SEQ ID NOs: 3-26 or 52, or a fragment thereof comprising at least 10 consecutive amino acids thereof.

In one embodiment, the amino acid sequence identity exists over a region of the amino acid sequences that is at least 10 consecutive amino acid residues in length (eg. at least 25, 50, 75, 100, 150, 200, 250, 300, 350, 400, or 413) consecutive amino acid residues in length).

Conventional methods for determining amino acid sequence identity are discussed in more detail later in the specification.

In the context of the second domain, a fragment comprises (or consists of) at least 10 consecutive amino acid residues of said amino acid sequence (eg. at least 25, 50, 75, 100, 150, 200, 250, 300, 350, 400, or 412 consecutive amino acid residues thereof).

In one embodiment, in the context of the second domain, a fragment of an amino acid sequence has a sequence length that is at least 5%, 10%, 20%, 30%, 40%, 50%, 60%, 70%, 80%, 90% or 95% of that of the sequence of the full-length amino acid sequence.

A fragment of a polypeptide may include at least one epitope of the polypeptide.

In one embodiment, the second domain comprises a mycobacterial antigen (or antigenic fragment thereof) selected from the family of mycobacterial antigens comprising Antigen 85A, Antigen 85B and Antigen 85C. This highly homologous family of proteins is secreted by *M. tuberculosis*, BCG, and many other species of mycobacteria.

Antigen 85A (Rv3804c) is represented by SEQ ID NO: 3, Antigen 85B (Rv1886c) is represented by SEQ ID NO: 4, and Antigen 85C(Rv0129c) is represented by SEQ ID NO: 5.

Thus, in one embodiment, the second domain comprises an amino acid sequence having at least 70% sequence identity (eg. at least 75, 80, 82, 84, 86, 88, 90, 92, 94, 96, 98, 99 or 100% sequence identity) to an amino acid sequence selected from SEQ ID NOs: 3, 4, 5, or 52 or a fragment thereof comprising at least 10 consecutive amino acids thereof.

In one embodiment, the polynucleotide sequence of the invention encodes a fusion protein comprising first and second domains, wherein the first domain of said fusion protein comprises an amino acid sequence having at least 70% sequence identity to SEQ ID NO: 1, or a fragment thereof comprising at least 20 consecutive amino acids thereof; and wherein the second domain of said fusion protein comprises an amino acid sequence having at least 70% sequence identity to an amino acid sequence selected from SEQ ID NOs: 3-5 or 52, or a fragment thereof comprising at least 10 consecutive amino acids thereof.

In one embodiment, the polynucleotide sequence of the invention encodes a fusion protein comprising a first domain and a second domain, wherein the first domain of said fusion protein is encoded by a nucleic acid sequence having at least 70% identity to the nucleic acid sequence of SEQ ID NO: 2 or SEQ ID NO: 53, or a fragment thereof comprising at least 60 consecutive nucleotides thereof.

In one embodiment, the polynucleotide sequence of the invention comprises a nucleic acid sequence encoding the first domain of the fusion protein, wherein said 'first domain' nucleic acid sequence comprises a nucleotide sequence having at least 70% (such as at least 75, 80, 82, 84, 86, 88, 90, 92, 94, 96, 98, 99 or 100%) nucleic acid sequence identity to the nucleic acid sequence of SEQ ID NO: 2 or SEQ ID NO: 53, or a fragment thereof comprising at least 60 consecutive nucleotides thereof.

In one embodiment, the polynucleotide sequence of the invention comprises a nucleic acid sequence encoding the first domain of the fusion protein, wherein said 'first domain' nucleic acid sequence consists of a nucleotide sequence having at least 70% (such as at least 75, 80, 82, 84, 86, 88, 90, 92, 94, 96, 98, 99 or 100%) nucleic acid sequence identity to the nucleic acid sequence of SEQ ID NO: 2 or SEQ ID NO: 53, or a fragment thereof comprising at least 60 consecutive nucleotides thereof.

In one embodiment, the nucleic acid sequence identity exists over a region of the nucleic acid sequences that is at least 60 consecutive nucleotides in length (eg. at least 65, 70, 75, 80, 84, 90, 100, 110, 120, 130, 140, 150, 155, 160, 165 consecutive nucleotides in length).

Conventional methods for determining nucleic acid sequence identity are discussed in more detail later in the specification.

In the context of the first domain, a nucleic acid sequence fragment comprises (or consists of) at least 60 consecutive nucleotides of said nucleic acid sequence (eg. at least 65, 70, 75, 80, 84, 90, 100, 110, 120, 130, 140, 145, 150, 152, 154, 156, 158, 160, 162 or 164 consecutive nucleotides thereof).

In one embodiment, in the context of the first domain, a fragment of a nucleic acid sequence has a sequence length that is at least 40%, 50%, 60%, 70%, 80%, or 90% of that of the sequence of the full-length nucleic acid sequence.

In one embodiment, in the context of the first domain, the polynucleotide sequence is codon-optimized for expression in a particular host/host cell. Thus, in one embodiment, said first domain is encoded by a codon-optimized polynucleotide comprising or consisting of a nucleotide sequence having at least 70% (such as at least 75, 80, 82, 84, 86, 88, 90, 92, 94, 96, 98, 99 or 100%) nucleic acid sequence identity to the nucleic acid sequence of SEQ ID NO: 2. In one embodiment, said codon-optimized nucleic acid encoding said first domain comprises or consists of SEQ ID NO: 53.

Conventional methods for codon-optimizing nucleic acid sequences are discussed in more detail later in the specification.

In one embodiment, the polynucleotide sequence of the invention encodes a fusion protein comprising a first domain and a second domain, wherein the second domain of said fusion protein is encoded by a nucleic acid sequence having at least 70% identity to the nucleic acid sequence selected from SEQ NOs: 27-51 or 56, or a fragment thereof comprising at least 30 consecutive nucleotides thereof.

Thus, in one embodiment, the polynucleotide sequence of the invention comprises a nucleic acid sequence encoding the second domain of the fusion protein, wherein said 'second domain' nucleic acid sequence comprises a nucleotide sequence having at least 70% (such as at least 75, 80, 82, 84, 86, 88, 90, 92, 94, 96, 98, 99 or 100%) nucleic acid sequence identity to the nucleic acid sequence of SEQ ID NO: 27-51 or 56, or a fragment thereof comprising at least 30 consecutive nucleotides thereof.

Thus, in one embodiment, the polynucleotide sequence of the invention comprises a nucleic acid sequence encoding the second domain of the fusion protein, wherein said 'second domain' nucleic acid sequence consists of a nucleic acid sequence having at least 70% (such as at least 75, 80, 82, 84, 86, 88, 90, 92, 94, 96, 98, 99 or 100%) nucleic acid sequence identity to the nucleic acid sequence of SEQ ID NOs: 27-51 or 56, or a fragment thereof comprising at least 30 consecutive nucleotides thereof.

In one embodiment, the nucleic acid sequence identity exists over a region of the nucleic acid sequences that is at least 30 consecutive nucleotides in length (eg. at least 50, 75, 100, 150, 200, 250, 300, 350, 400, 450, 500, 550, 600, 650, 700, 750, 800, 850, 900, 950, 1000, 1050, 1100, 1150 or 1200) consecutive nucleotides in length.

Conventional methods for determining nucleic acid sequence identity are discussed in more detail later in the specification.

In the context of the second domain, a nucleic acid sequence fragment comprises (or consists of) at least 30 consecutive nucleotides of said nucleic acid sequence (eg. at least 50, 75, 100, 150, 200, 250, 300, 350, 400, 450, 500, 550, 600, 650, 700, 750, 800, 850, 900, 950, 1000, 1050, 1100, 1150 or 1199 consecutive nucleotides thereof).

In one embodiment, in the context of the second domain, a fragment of a nucleic acid sequence has a sequence length that is at least 20%, 30%, 40%, 50%, 60%, 70%, 80%, or 90% of that of the sequence of the full-length nucleic acid sequence.

In one embodiment, in the context of the second domain, the polynucleotide sequence is codon-optimized for expression in a particular host/host cell. Thus, in one embodiment, the second domain comprises or consists of codon-optimized versions of the mycobacterial antigens (or antigenic fragments thereof) described herein. In one embodiment, said second domain is encoded by a codon-optimized polynucleotide comprising or consisting of a nucleotide sequence having at least 70% (such as at least 75, 80, 82, 84, 86, 88, 90, 92, 94, 96, 98, 99 or 100%) nucleic acid sequence identity to the nucleic acid sequence of SEQ ID NO: 27. In one embodiment, said codon-optimized nucleic acid encoding said second domain comprises or consists of SEQ ID NO: 51 or 56.

Conventional methods for codon-optimizing nucleic acid sequences are discussed in more detail later in the specification.

In one embodiment, the polynucleotide of the present invention encoding a fusion protein comprising first and second domains comprises or consists of a nucleotide sequence having at least 70% (such as at least 75, 80, 82, 84, 86, 88, 90, 92, 94, 96, 98, 99 or 100%) nucleic acid sequence identity to the nucleic acid sequence of SEQ ID NO: 54, or a fragment thereof.

In one embodiment, the nucleic acid sequence identity exists over a region of the nucleic acid sequences that is at least 30 consecutive nucleotides in length (eg. at least 50, 75, 100, 150, 200, 250, 300, 350, 400, 450, 500, 550, 600, 650, 700, 750, 800, 850, 900, 950, 1000, 1050, 1100, 1119, 1150 or 1200) consecutive nucleotides in length.

Conventional methods for determining nucleic acid sequence identity are discussed in more detail later in the specification.

In the context of the polynucleotide of the present invention, a nucleic acid sequence fragment comprises (or consists of) at least 30 consecutive nucleotides of said nucleic acid sequence (eg. at least 50, 75, 100, 150, 200, 250, 300, 350, 400, 450, 500, 550, 600, 650, 700, 750, 800, 850, 900, 950, 1000, 1050, 1100 or 1118 consecutive nucleotides thereof).

In one embodiment, in the contest of the polynucleotide of the present invention, a fragment of a nucleic acid sequence has a sequence length that is at least 20%, 30%, 40%, 50%, 60%, 70%, 80%, or 90% of that of the sequence of the full-length nucleic acid sequence.

In one embodiment, the polynucleotide sequence of the invention encodes a fusion protein comprising first and second domains, wherein the first domain of the fusion protein is arranged C-terminal of the second domain of the fusion protein. In an alternative embodiment, the polynucleotide of the invention encodes a fusion protein comprising first and second domains, wherein the first domain of the fusion protein is arranged N-terminal of the second domain.

Thus, in one embodiment, the polynucleotide sequence of the invention comprises nucleic acid sequences encoding the first domain and the second domain of the fusion protein, wherein the nucleic acid sequence encoding the first domain of the fusion protein is arranged 3' to the nucleic acid sequence encoding the second domain. In an alternative embodiment, the nucleic acid sequence encoding the first domain of the fusion protein is arranged 5' to the nucleic acid sequence encoding the second domain.

In one embodiment, the polynucleotide of the invention further comprises a nucleic acid sequence that encodes an intervening ‘linker’ sequence, located between the first and second domains of the fusion protein. In accordance with this embodiment, the ‘linker’ nucleic acid sequence is located between the nucleic acid sequence encoding the first domain of the fusion protein and the nucleic acid sequence encoding the second domain of the fusion protein. In one embodiment, said linker is a ‘glycine-serine’ (i.e. Gly-Ser) linker, for example a glycine-serine linker encoded by the nucleotide sequence “ggcagc”.

In general, the amino acids encoded by these linker sequences are not deleterious to the immunogenicity of the resultant fusion protein, and may even be beneficial to immunogenicity.

Alternatively, a fusion protein of the invention may be produced as an epitope string, by expression of polynucleotide sequences that are linked without intervening nucleotides. The absence of intervening linker sequence avoids the presence of unnecessary nucleic acid and/or amino acid material. Thus, in accordance with this embodiment, the polynucleotide sequence does not comprise any ‘linker’ intervening nucleotides between the nucleic acid sequences encoding the first and second domains of the fusion protein.

In one embodiment, the polynucleotide sequence of the invention encodes a fusion protein, wherein the encoded fusion protein comprises at least one additional domain (ie. in addition to the first and second domains defined above). For example, the fusion protein may comprise at least one additional antigen or antigenic fragment (such as 2, 3, 4, 6, 8, 10 additional antigens or antigenic fragments).

Thus, in one embodiment, the polynucleotide of the invention comprises additional nucleic acid sequences (in addition to the nucleic acid sequences encoding the first and second domains defined above) that encode at least one additional domain, such as at least one additional antigen or antigenic fragment (such as 2, 3, 4, 6, 8, 10 additional nucleic acid sequences encoding additional antigens or antigenic fragments).

As discussed above, the additional antigen(s) or fragments may be the same as mycobacterial antigen/antigenic fragment that is comprised in the second domain of the fusion protein. Alternatively, the additional antigen(s) or fragments may be different from the mycobacterial antigen/antigenic fragment that is comprised in the second domain of the fusion protein. By way of example, the additional antigen(s) or fragments may be a mycobacterial antigen (or antigenic fragment) or may be non-mycobacterial—eg. from a different pathogen such as a different pathogenic bacterium.

In another aspect, the invention provides a vector comprising a polynucleotide sequence of the invention that encodes a fusion protein comprising first and second domains (as defined above).

The positive immunogenicity results achieved with a vector of the invention (see Example 3 and FIGS. 1-6 below) are most surprising and unexpected. For example, in contrast to the present invention, vectors comprising a fusion of SEQ ID NO: 1 with malarial antigens did not result in an enhanced immune response (see Example 3 and FIG. 7 below). Even more surprising is that the positive immunogenicity towards the mycobacterial antigen observed in mice was also observed in primates.

In one embodiment, the vector is selected from a DNA vector, a RNA vector, a viral vector, a bacterial vector, a plasmid vector, a cosmid vector, an artificial chromosome vector, such as a yeast artificial chromosome vector.

In one embodiment of the invention, the vector is a DNA vector such as a plasmid DNA vector. In another embodiment the vector is a viral vector. In one embodiment, the viral vector is an adenovirus or a modified vaccinia Ankara (MVA) virus vector.

Viral vectors are usually non-replicating or replication-impaired vectors, which means that the viral vector cannot replicate to any significant extent in normal cells (eg. normal human cells), as measured by conventional means—eg. via measuring DNA synthesis and/or viral titre. Non-replicating or replication-impaired vectors may have become so naturally (ie. they have been isolated as such from nature) or artificially (eg. by breeding in vitro or by genetic manipulation). There will generally be at least one cell-type in which the replication-impaired viral vector can be grown—for example, modified vaccinia Ankara (MVA) can be grown in CEF cells.

Typically, the viral vector is incapable of causing a significant infection in an animal subject, typically in a mammalian subject such as a human, cow, pig, horse, badger or fox.

In one embodiment, the vector is selected from an adenovirus or a poxvirus vector. Examples of viral vectors that are useful in this context include attenuated vaccinia virus vectors such as modified vaccinia Ankara (MVA) and NYVAC, or strains derived therefrom. Other examples of vectors include an avipox vector, such as a fowlpox vectors (eg. FP9) or canarypox vectors (eg. ALVAC and strains derived therefrom). Alternative viral vectors useful in the present invention include adenoviral vectors (eg. non-human adenovirus vectors), alphavirus vectors, flavivirus vectors, herpes viral vectors (eg. herpes simplex, CMV and EBV), influenza virus vectors and retroviral vectors.

Adenoviruses are commonly used as vectored vaccines and can be distinguished into several different classes. Fowl adenoviruses-derived vectors, for example, are preferred for vaccination of avian species, and may have less utility in vaccinating mammals against mycobacteria. Adenoviruses are classified by the host(s) from which they were initially isolated. Thus, the scientific literature commonly refers to “human adenoviruses”, “chimpanzee adenoviruses” and “simian adenoviruses”. All three groups have utility for preparing mycobacterial vaccines. An attraction of adenoviral vectors derived from chimpanzee adenoviruses is that humans have seldom been naturally infected by such viruses and thus pre-existing immunity to such vectors is negligible. Further distinctions can be made amongst adenoviral vectors derived from human adenoviruses on the same basis: infection by adenovirus 5 (Ad5) is very common in human populations and thus, there may be a preference when using human adenoviral vectors to use those derived from rarer human isolates or where cross-immunity following natural Ad5 infection is limited. Examples of vectors derived from such rarer isolates include the Ad35 and Ad11 vectors as well as the Ad26, Ad48, and Ad50 vectors.

In one embodiment, the vector is a human adenovirus. In another embodiment, the vector is a simian adenovirus. In another embodiment, the vector is a chimpanzee adenovirus. A chimpanzee as referred to herein may include *Pan troglodytes* (common chimpanzee) and *Pan paniscus* (Bonobo). In one embodiment, the vector is selected from adenovirus 5 (Ad5), adenovirus 35 (Ad35), adenovirus 11 (Ad11), adenovirus 26 (Ad26), adenovirus 48 (Ad48) or adenovirus 50 (Ad50). The present Inventors have noted that antigens which induce good immunogenicity when expressed from human adenoviruses are also immunogenic when expressed from chimpanzee adenoviruses. This has been confirmed by the scientific literature in comparative evaluations of various antigens in human and chimpanzee adenoviral expression systems—see, for example, Reyes-Sandoval et al. 2010 (Infection and Immunity, January 2010, p. 145-153, Vol. 78, No. 1).

The vectors of the invention optionally include appropriate control sequences such as a promoter and/or terminator. Expression control sequences for such vectors are known to those skilled in the art and may be selected depending upon the host cells.

In one embodiment, the vector is an expression vector.

Expression vectors are nucleic acid molecules (linear or circular) that comprise one or more polynucleotide sequences encoding a polypeptide(s) of interest, operably linked to additional regulatory elements required for its expression.

In this regard, expression vectors generally include promoter and terminator sequences, and optionally one or more enhancer sequences, polyadenylation signals, and the like. Expression vectors may also include suitable translational regulatory elements, including ribosomal binding sites, and translation initiation and termination sequences. The transcriptional and translational regulatory elements employed in the expression vectors of the invention are functional in the host cell used for expression, and may include those naturally associated with mycobacterial genes.

The selection of suitable promoters, terminators, selectable markers and other elements is a matter of routine design within the level of ordinary skill in the art.

Promoters such as the trp, lac and phage promoters, tRNA promoters and glycolytic enzyme promoters may be used in prokaryotic hosts. Useful yeast promoters include the promoter regions for metallothionein, 3-phosphoglycerate kinase or other glycolytic enzymes such as enolase or glyceraldehyde-3-phosphate dehydrogenase, enzymes responsible for maltose and galactose utilization, and others. Appropriate non-native mammalian promoters may include the early and late promoters from SV40 or promoters derived from murine moloney leukaemia virus, mouse mammary tumour virus, avian sarcoma viruses, adenovirus II, bovine papilloma virus or polyoma. In one embodiment, the expression vector comprises a CMV promoter.

Generally, “operably linked” means that the nucleic acid sequences being linked are contiguous and arranged so that they function in concert for their intended purposes—for example, transcription initiates in the promoter and proceeds through the coding polynucleotide segment to the terminator. Where necessary to join two protein coding regions, the polynucleotide coding sequences should be contiguous and in reading frame.

In one embodiment, the invention provides a fusion protein comprising first and second domains, wherein the first domain comprises an amino acid sequence having at least 70% sequence identity to the amino acid sequence of SEQ ID NO: 1, or a fragment thereof comprising at least 20 consecutive amino acids thereof, and wherein the second domain of the fusion protein comprises a mycobacterial antigen or an antigenic fragment thereof.

The positive immunogenicity results achieved with fusions the present invention (see Example 3 and FIGS. 1-6 below) are most surprising and unexpected. For example, in contrast to the present invention, fusions of SEQ ID NO: 1 with malarial antigens did not result in an enhanced immune response (see Example 3 and FIG. 7 below). Even more surprising is that the positive immunogenicity towards the mycobacterial antigen observed in mice was also observed in primates.

In one embodiment, the first domain comprises (or consists of) an amino acid sequence having at least 70% (such as at least 75, 80, 82, 84, 86, 88, 90, 92, 94, 96, 98, 99 or 100%) amino acid sequence identity to the amino acid sequence of SEQ ID NO: 1, or a fragment thereof comprising at least 20 consecutive amino acids thereof.

In one embodiment, the amino acid sequence identity exists over a region of the amino acid sequences that is at least 20 consecutive amino acid residues in length (eg. at least 25, 28, 30, 35, 40, 45, 50, or 55 consecutive amino acid residues in length).

Conventional methods for determining amino acid sequence identity are discussed in more detail later in the specification.

In the context of the first domain, a fragment comprises (or consists of) at least 20 consecutive amino acid residues of said amino acid sequence (eg. at least 25, 28, 30, 35, 40, 42, 44, 46, 48, 50, 52 or 54 consecutive amino acid residues thereof).

In one embodiment, in the context of the first domain, a fragment of an amino acid sequence has a sequence length that is at least 40% 50%, 60%, 70%, 80%, or 90% of that of the sequence of the full-length amino acid sequence.

The second domain of the fusion protein comprises a mycobacterial antigen, or an antigenic fragment of said mycobacterial antigen.

In one embodiment the second domain comprises a mycobacterial antigen selected from 85A/Rv3804c, 85B/Rv1886c, 85C/Rv0129c, ESAT6/Rv3875, TB10.4/Rv0288, Rv0125, PPE18/Rv1196, P27/Rv1411c, HSP65/Rv0440, HBHA/Rv0475, Rv2659c, Rv2660c, HspX/Rv2031c, RPFA/Rv0867c, RPFB/Rv1009, RPFC/Rv1884c, RPFD/Rv2389c, RPFE/Rv2450c, Rv1733c, Rv2029c, Rv2032, Rv2626c, Rv2627c, Rv2628, Rv0111, Rv1806/1807, Rv0198, or Rv3812 or antigenic fragments thereof.

In one embodiment, the second domain comprises (or consists of) an amino acid sequence having at least 70% (such as at least 75, 80, 82, 84, 86, 88, 90, 92, 94, 96, 98, 99 or 100%) amino acid sequence identity to an amino acid sequence selected from SEQ ID NOs: 3-26 or 52, or a fragment thereof comprising at least 10 consecutive amino acids thereof.

In one embodiment, the amino acid sequence identity exists over a region of the amino acid sequences that is at least 10 consecutive amino acid residues in length (eg. at least 25, 50, 75, 100, 150, 200, 250, 300, 350, 400, or 413) consecutive amino acid residues in length).

Conventional methods for determining amino acid sequence identity are discussed in more detail later in the specification.

In the context of the second domain, a fragment comprises (or consists of) at least 10 consecutive amino acid residues of said amino acid sequence (eg. at least 25, 50, 75, 100, 150, 200, 250, 300, 350, 400 or 412 consecutive amino acid residues thereof). In one embodiment, in the context of the second domain, a fragment of an amino acid sequence has a sequence length that is at least 20%, 30%, 40%, 50%, 60%, 70%, 80%, or 90% of that of the sequence of the full-length amino acid sequence.

A fragment of a polypeptide may include at least one epitope of the polypeptide.

In one embodiment, the second domain comprises a mycobacterial antigen (or antigenic fragment thereof) selected from the family of mycobacterial antigens comprising Antigen 85A (SEQ ID NO: 3 or SEQ ID NO: 52), Antigen 85B (SEQ ID NO: 4) and Antigen 85C (SEQ ID NO: 5). This highly homologous family of proteins is secreted by *M. tuberculosis*, BCG, and many other species of mycobacteria.

Thus, in one embodiment, the second domain comprises an amino acid sequence having at least 70% sequence identity to an amino acid sequence selected from SEQ ID NOs: 3, 4, 5 or 52 or a fragment thereof comprising at least 10 consecutive amino acids thereof.

In one embodiment, the fusion protein of the invention comprises first and second domains, wherein the first domain of said fusion protein comprises an amino acid sequence having at least 70% sequence identity to SEQ ID NO: 1, or a fragment thereof comprising at least 20 consecutive amino acids thereof; and wherein the second domain of said fusion protein comprises an amino acid sequence having at least 70% sequence identity to an amino acid sequence selected from SEQ ID NOs: 3, 4, 5 or 52, or a fragment thereof comprising at least 10 consecutive amino acids thereof.

In one embodiment, the first domain of the fusion protein is arranged C-terminal of the second domain (ie. in the order "second domain-first domain"). Alternatively, the first domain of the fusion protein is arranged N-terminal of the second domain (ie. in the order "first domain-second domain").

In one embodiment, the fusion protein of the present invention comprises or consists of an amino acid sequence having at least 70% (such as at least 75, 80, 82, 84, 86, 88, 90, 92, 94, 96, 98, 99 or 100%) amino acid sequence identity to the amino acid sequence of SEQ ID NO: 55, or a fragment thereof.

In one embodiment, the amino acid sequence identity exists over a region of the amino acid sequences that is at least 10 consecutive amino acid residues in length (eg. at least 25, 50, 75, 100, 150, 200, 250, 300, 350, or 338 or 372) consecutive amino acid residues in length).

Conventional methods for determining amino acid sequence identity are discussed in more detail later in the specification.

In the context of the fusion protein, a fragment comprises (or consists of) at least 10 consecutive amino acid residues of said amino acid sequence (eg. at least 25, 50, 75, 100, 150, 200, 250, 300, 350, 337 or 371 consecutive amino acid residues thereof).

In one embodiment, in the context of the fusion protein, a fragment of an amino acid sequence has a sequence length that is at least 5%, 10%, 20%, 30%, 40%, 50%, 60%, 70%, 80%, 90% or 95% of that of the sequence of the full-length amino acid sequence.

In one embodiment, the fusion protein of the invention comprises intervening 'linker' sequences located between the first and second domains of the fusion protein. In general, the amino acids encoded by these linker sequences are not deleterious to the immunogenicity of the resultant fusion protein, and may even be beneficial to immunogenicity. In one embodiment, the linker sequence comprises or consists of the amino acids gylcine and serine. In a preferred embodiment, the linker sequence comprises or consists of (in a 5'->3' direction) gylcine and serine i.e. Gly-Ser. Alternatively, a fusion protein of the invention may be produced as an epitope string, by expression of polynucleotide sequences that are linked without intervening nucleotides. In this embodiment, the fusion protein does not comprise intervening 'linker' amino acids between the first and second domains. The absence of intervening linker sequence avoids the presence of unnecessary nucleic acid and/or amino acid material.

In one embodiment, the fusion protein of the invention further comprises at least one additional domain (ie. in addition to the first and second domains defined above). For example, the fusion protein may comprise at least one additional antigen or antigenic fragment (such as 2, 3, 4, 6, 8, 10 additional antigens or antigenic fragments). In one embodiment, the additional antigen(s) or fragments may be the same as (or derived from the same) mycobacterial antigen/antigenic fragment that is comprised in the second domain of the fusion protein. In one embodiment, the additional antigen(s) or fragments may be different from the mycobacterial antigen/antigenic fragment that is comprised in the second domain of the fusion protein. By way of example, the additional antigen(s) or fragments may be a mycobacterial antigen (or antigenic fragment) or may be non-mycobacterial—eg. from a different pathogen such as a different pathogenic bacterium.

In one embodiment, the invention provides a method of producing a fusion protein comprising expressing a polynucleotide of the invention (as described above) or a vector of the invention (as described above) in a host cell.

Generation of fusion proteins is well known in the art. Fusion proteins may be generated by expression of a recombinant polynucleotide sequence that encodes the fusion protein. By way of example, polynucleotide sequences encoding first and second domains of the fusion protein of the invention may be positioned in the same reading frame downstream of a promoter in a vector, thereby allowing transcription through the polynucleotide sequences and translation as one protein product.

The fusion proteins of the invention may be prepared by expressing the polynucleotide sequences of the invention in vectors or other expression vehicles in compatible prokaryotic or eukaryotic host cells using standard molecular biology methods (e.g., Sambrook et al. 1989, Molecular Cloning a Laboratory Manual, Second Edition, Cold Spring Harbor Laboratory Press, Cold Spring Harbor, N.Y.; incorporated herein by reference).

The most commonly used prokaryotic hosts are strains of *E. coli*, although other prokaryotes, such as *B. subtilis* or *Pseudomonas* may be used. Mammalian or other eukaryotic host cells, such as those of yeast, filamentous fungi, plant, insect, amphibian or avian species, may also be useful in the present invention. Propagation of mammalian cells in culture is per se well known. Examples of commonly used mammalian host cell lines are VERO and HeLa cells, Chinese hamster ovary (CHO) cells, and WI38, BHK, and COS cell lines, although other cell lines may be appropriate, e.g., to provide higher expression.

As used herein, "host cells", and other such terms denoting microorganisms or higher eukaryotic cell lines cultured as unicellular entities refer to cells which can be, or have been, used as recipients for recombinant vector or other transfer DNA, and include the progeny of the original cell which has been transformed. It is understood that the progeny of a single parental cell may not necessarily be completely identical in morphology or in genomic or total DNA complement as the original parent, due to natural, accidental or deliberate mutation.

Polynucleotide sequences of interest can be transcribed in vitro and the resulting RNA introduced into the host cell (eg. by injection), or the polynucleotide sequences can be introduced directly into host cells by methods which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome). "Transformation" refers to the insertion of an exogenous polynucleotide into a host cell, irrespective of the method used for the insertion, for example, direct uptake, transduction, f-mating or electroporation.

Vectors may replicate autonomously, or may replicate by being inserted into the genome of a host cell, in which case they include an insertion sequence.

Expression and cloning vectors may contain a selectable marker, a gene encoding a protein necessary for the survival or growth of a host cell transformed with the vector. This gene ensures the growth of only those host cells which express the inserts. Conventional selection genes encode proteins that (a) confer resistance to antibiotics or other toxic substances, eg. ampicillin, neomycin, methotrexate, etc.; (b) complement auxotrophic deficiencies; or (c) supply critical nutrients not available from complex media, e.g. the gene encoding D-alanine racemase for Bacilli. The choice of appropriate selectable marker will depend on the host cell.

The transformed host cell can be cultured in accordance with known methods, and the expressed polypeptide may be harvested i.e. recovered and isolated (eg. from the culture medium) using conventional protocols.

Thus, in one embodiment, the invention provides a host cell comprising a polynucleotide sequence of the invention, or a vector of the invention, or a fusion protein of the invention (as described above).

In one embodiment, the invention provides an immunogenic composition comprising a polynucleotide sequence of the invention, or a vector of the invention, or a fusion protein of the invention (as described above) and a pharmaceutically acceptable carrier.

In the present context, "immunogenic" composition refers to the ability of an antigen in the composition to elicit an immune response. The immune response includes humoral and/or cell-mediated immune responses such as CD4+, CD8+, and/or IFN-γ responses.

The positive immunogenicity results achieved with an immunogenic composition of the invention (see Example 3 and FIGS. 1-6 below) are most surprising and unexpected. For example, in contrast to the present invention, fusion of SEQ ID NO: 1 with malarial antigens did not result in an enhanced immune response (see Example 3 and FIG. 7 below). Even more surprising is that the positive immunogenicity towards the mycobacterial antigen observed in mice was also observed in primates.

It is routine in the art to monitor an immune response. For example, new immunological assays for measuring and quantifying T cell responses have been established over the last 10 years. For example, the interferon-gamma (IFN-γ) ELISPOT assay is useful as an immunological readout because the secretion of IFN-γ from antigen-specific T cells is a good correlate of protection against *M. tuberculosis*. Furthermore, the ELISPOT assay is a very reproducible and sensitive method of quantifying the number of IFN-γ secreting antigen-specific T cells. An immune response can also be measured by way of measuring an antibody titer that is specific for an antigen.

In one embodiment, the invention provides a polynucleotide sequence, or a vector, or a fusion protein or an immunogenic composition of the invention (as described above) for use in stimulating or inducing an immune response in a subject.

In one embodiment, the invention provides use of a polynucleotide sequence, or a vector, or a fusion protein or an immunogenic composition of the invention (as described above) in the manufacture of a medicament for stimulating or inducing an immune response in a subject.

In the context of the therapeutic uses and methods, a 'subject' is any animal subject that would benefit from stimulation or induction of an immune response against mycobacteria, such as *M. tuberculosis*. Typical animal subjects are mammals, such as primates, for example, human, bovine, porcine, ovine, caprine, equine, corvine, canine or feline subjects. In one embodiment, the subject is a human, a cow, a pig, a horse, a badger or a fox.

In one embodiment, the invention provides a polynucleotide sequence, or a vector, or a fusion protein or an immunogenic composition of the invention (as described above) for use in the treatment or prevention of a mycobacterial infection, such as a *M. tuberculosis* infection.

The positive immunogenicity results achieved with fusions of the present invention (see Example 3 and FIGS. 1-6 below) are most surprising and unexpected. For example, in contrast to the present invention, fusions of SEQ ID NO: 1 with malarial antigens did not result in an enhanced immune response (see Example 3 and FIG. 7 below). Even more surprising is that the positive immunogenicity towards the mycobacterial antigen observed in mice was also observed in primates.

In one embodiment, the invention provides use of a polynucleotide sequence, or a vector, or a fusion protein or an immunogenic composition of the invention (as described above) for the manufacture of a medicament for the treatment or prevention of a mycobacterial infection, such as a *M. tuberculosis* infection.

The present invention also provides a method of stimulating or inducing an immune response in a subject comprising administering to the subject a polynucleotide sequence of the invention, or vector of the invention, or fusion protein of the invention, or immunogenic composition of the invention (as described above).

Thus, in one embodiment, the method of stimulating or inducing an immune response in a subject comprises administering a polynucleotide sequence of the invention, or a vector of the invention, or a fusion protein of the invention, or an immunogenic composition of the invention (as described above) to a subject.

In one embodiment, the present invention provides a method for treating or preventing mycobacterial infection, such as a *M. tuberculosis* infection.

In one embodiment, the method for treating or preventing mycobacterial infection, such as a *M. tuberculosis* infection comprises administering a polynucleotide sequence of the invention, or a vector of the invention, or a fusion protein of the invention, or an immunogenic composition of the invention (as described above) to a subject.

In one embodiment, the method of stimulating or inducing an immune response in a subject comprises administering a polynucleotide sequence of the invention, or a vector of the invention, or a fusion protein of the invention, or an immunogenic composition of the invention (as described above) to a subject, wherein said polynucleotide sequence, or vector, or fusion protein, or immunogenic composition is administered substantially prior to, simultaneously with or subsequent to another immunogenic composition.

In one embodiment, the method for treating or preventing mycobacterial infection, such as a *M. tuberculosis* infection in a subject comprises administering a polynucleotide sequence of the invention, or a vector of the invention, or a fusion protein of the invention, or an immunogenic composition of the invention (as described above) to a subject, wherein said polynucleotide sequence, or vector, or fusion protein, or immunogenic composition is administered substantially prior to, simultaneously with or subsequent to administration of another immunogenic composition.

In one embodiment, the method for treating or preventing mycobacterial infection, such as *M. tuberculosis* infection in a subject comprises administering a polynucleotide sequence of the invention, or a vector of the invention, or a fusion protein of the invention, or an immunogenic composition of the invention as a booster vaccine composition up to 1, 2, 3, 4 or 5 years after administration of priming vaccine composition.

In one embodiment, the priming vaccine composition comprises or encodes a second mycobacterial antigen (eg. BCG).

Prior, simultaneous, and sequential administration regimes including "prime-boost'" vaccination regimes are discussed in more detail later in the specification.

The polynucleotide sequence, or vector, or fusion protein, or immunogenic composition of the present invention may be useful for inducing a range of immune responses and may therefore be useful in methods for treating a range of diseases.

In one embodiment, polynucleotide sequence, or vector, or fusion protein, or immunogenic composition of the present invention are useful for treating or preventing a range of non-mycobacterial diseases in which mycobacteria are implicated. For example, diseases that may benefit from the medicament of the invention include inflammatory diseases such as autoimmune disease, cancer (eg. bladder cancer), inflammatory bowel disease, Crohn's Disease, Johne's Disease, Hansen's Disease, osteomyelitis, lymphadenitis, smallpox or monkeypox.

As used herein, the term "treatment" or "treating" embraces therapeutic or preventative/prophylactic measures, and includes post-infection therapy and amelioration of a mycobacterial infection.

As used herein, the term "preventing" includes preventing the initiation of a mycobacterial infection and/or reducing the severity or intensity of a mycobacterial infection.

A polynucleotide sequence, or vector, or fusion protein, or immunogenic composition of the invention (as described above) may be administered to a subject (typically a mammalian subject such as a human, a cow, a pig, a horse, a badger or a fox) already having a mycobacterial infection, condition or symptoms associated with a mycobacterial infection, to treat or prevent said mycobacterial infection. In one embodiment, the subject is suspected of having come in contact with mycobacteria, or has had known contact with mycobacteria, but is not yet showing symptoms of exposure.

When administered to a subject (eg. a mammal such as a human, a cow, a pig, a horse, a badger or a fox) that already has a mycobacterial infection or disease, or is showing symptoms associated with a mycobacterial infection, the polynucleotide sequence, or vector, or fusion protein, or immunogenic composition of the invention (as previously described) can cure, delay, reduce the severity of, or ameliorate one or more symptoms, and/or prolong the survival of a subject beyond that expected in the absence of such treatment.

Alternatively, a polynucleotide sequence, or vector, or fusion protein, or immunogenic composition of the invention (as described above) may be administered to a subject (eg. a mammal such as a human, a cow, a pig, a horse, a badger or a fox) who ultimately may acquire a mycobacterial infection, in order to prevent, cure, delay, reduce the severity of, or ameliorate one or more symptoms of said mycobacterial infection, or in order to prolong the survival of a subject beyond that expected in the absence of such treatment.

In one embodiment, the subject has previously been exposed to mycobacteria. For example, the subject may have had a mycobacterial infection in the past (but is optionally not currently infected with mycobacteria). The subject may be latently infected with mycobacteria. Alternatively, or in addition, the subject may have been vaccinated against mycobacterial infection in the past (eg. the subject has previously received a BCG vaccination).

The treatments and preventative therapies of the present invention are applicable to a variety of different subjects of different ages. In the context of humans, the therapies are applicable to children (eg. infants, children under 5 years old, older children or teenagers) and adults. In the context of other animal subjects (eg. mammals such as cows, pigs, horses, badgers or foxes), the therapies are applicable to immature subjects (eg. calves, piglets, foals) and mature/adult subjects. The treatments and preventative therapies of the present invention are applicable to subjects who are immunocompromised or immunosuppressed (eg. human patients who have HIV or AIDS, or other animal patients with comparable immunodeficiency diseases), subjects who have undergone an organ transplant, bone marrow transplant, or who have genetic immuno-deficiencies.

The polynucleotides, fusion proteins, vectors and immunogenic compositions of the invention (as described above) can all be employed as vaccines.

As used, herein, a "vaccine" is a formulation that, when administered to an animal subject such as a mammal (eg. human, a cow, a pig, a horse, a badger, a fox, a sheep, a goat, a crow, a dog or a cat) stimulates a protective immune response against mycobacterial infection. The immune response may be a humoral and/or cell-mediated immune response. A vaccine of the invention can be used, for example, to protect an animal from the effects of mycobacterial invention (eg. *M. tuberculosis* infection).

The term "vaccine" is herein used interchangeably with the terms "therapeutic/prophylactic composition", "formulation" or "medicament".

The vaccine of the invention (as defined above) in addition to a pharmaceutically acceptable carrier can further be combined with one or more of a salt, excipient, diluent, adjuvant, immunoregulatory agent and/or antimicrobial compound.

The polynucleotide, or vector, or fusion protein or immunogenic composition of the invention may be formulated into a vaccine as neutral or salt forms. Pharmaceutically acceptable salts include acid addition salts formed with inorganic acids such as, for example, hydrochloric or phosphoric acids, or with organic acids such as acetic, oxalic, tartaric, maleic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Administration of immunogenic compositions, therapeutic formulations, medicaments and prophylactic formulations (eg. vaccines) is generally by conventional routes e.g. intravenous, subcutaneous, intraperitoneal, or mucosal routes. The administration may be by parenteral injection, for example, a subcutaneous or intramuscular injection. Formulations comprising neutralizing antibodies may be particularly suited to administration intravenously, intramuscularly, intradermally, or subcutaneously.

Accordingly, immunogenic compositions, therapeutic formulations, medicaments and prophylactic formulations (eg. vaccines) of the invention are typically prepared as injectables, either as liquid solutions or suspensions. Solid forms suitable for solution in, or suspension in, liquid prior to injection may alternatively be prepared. The preparation may also be emulsified, or the peptide encapsulated in liposomes or microcapsules.

The active immunogenic ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine.

Generally, the carrier is a pharmaceutically-acceptable carrier. Non-limiting examples of pharmaceutically acceptable carriers include water, saline, and phosphate-buffered saline. In some embodiments, however, the composition is in lyophilized form, in which case it may include a stabilizer, such as BSA. In some embodiments, it may be desirable to formulate the composition with a preservative, such as thiomersal or sodium azide, to facilitate long term storage.

Examples of additional adjuvants which may be effective include but are not limited to: complete Freunds adjuvant (CFA), Incomplete Freunds adjuvant (IVA), Saponin, a purified extract fraction of Saporin such as Quil A, a derivative of Saporin such as QS-21, lipid particles based on Saponin such as ISCOM/ISCOMATIX, *E. coli* heat labile toxin (LT) mutants such as LTK63 and/or LTK72, aluminium hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryl oxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

Examples of buffering agents include, but are not limited to, sodium succinate (pH 6.5), and phosphate buffered saline (PBS; pH 6.5 and 7.5).

Additional formulations which are suitable for other modes of administration include suppositories and, in some cases, oral formulations or formulations suitable for distribution as aerosols. For suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders.

In the case of animal subjects such as badgers or foxes, the formulation may comprise a carrier material to form a "bait". A variety of materials can be used to form the carrier material including both liquid and solid materials. For example, the carrier can be a food source that is effective to promote ingestion and/or attract specific animals. Examples of suitable food sources for use in bait formulations include, but are not limited to, wheat flour, wheat cereal, bran, molasses, vinegar, agar, gelatin, pet food, wheat, soy products, oats, corn, vegetable oils, rice, fruits, meat, meat by-products, fish, fish by-products, sugars, coated vegetable seeds, coated cereal seeds, dairy products, whey powder, casein, albumen, blood meal, bone meal, yeasts, fats, beer products, paper fiber, cellulose and mixtures thereof.

Other suitable additives include attractants and non-food carriers. Non-food carriers can be used alone or combined with food materials and/or attractants. Examples of non-food carriers suitable as additives include cellulose, sand, clay, silica, polyacrylic acid polymers, polyacrylamide acid polymers, alginate and wax.

In the case of a mycobacterial respiratory infection (eg. a *M. tuberculosis* infection), efficient transmission of the therapeutic/prophylactic composition or medicament to the site of infection in the lungs may be achieved by oral or intra-nasal administration (i.n.). These modes of delivery correspond to the route of delivery of a *M. tuberculosis* infection.

Formulations for intranasal administration may in the form of nasal droplets or a nasal spray. An intranasal formulation may comprise droplets having approximate diameters in the range of 100-5000 μm, such as 500-4000 μm, 1000-3000 μm or 100-1000 μm. Alternatively, in terms of volume, the droplets may be in the range of about 0.001-100 μl, such as 0.1-50 μl or 1.0-25 μl, or such as 0.001-1 μl.

Alternatively, the therapeutic/prophylactic formulation or medicament may be an aerosol formulation. The aerosol formulation may take the form of a powder, suspension or solution. The size of aerosol particles is relevant to the delivery capability of an aerosol. Smaller particles may travel further down the respiratory airway towards the alveoli than would larger particles. In one embodiment, the aerosol particles have a diameter distribution to facilitate delivery along the entire length of the bronchi, bronchioles, and alveoli. Alternatively, the particle size distribution may be selected to target a particular section of the respiratory airway, for example the alveoli. In the case of aerosol delivery of the medicament, the particles may have diameters in the approximate range of 0.1-50 μm, preferably 1-25 μm, more preferably 1-5 μm.

Aerosol particles may be for delivery using a nebulizer (eg. via the mouth) or nasal spray. An aerosol formulation may optionally contain a propellant and/or surfactant.

By controlling the size of the droplets/particles to within the defined range of the present invention, it is possible to avoid (or minimize) inadvertent medicament delivery to the alveoli and thus avoid alveoli-associated pathological problems such as inflammation and fibrotic scarring of the lungs.

I.n. vaccination engages both T and B cell mediated effector mechanisms in nasal and bronchus associated mucosal tissues, which differ from other mucosae-associated lymphoid tissues. The protective mechanisms invoked by the intranasal route of administration may include: the activation of T lymphocytes with preferential lung homing; up-regulation of co-stimulatory molecules (eg. B7.2); and/or activation of macrophages or secretory IgA antibodies.

Intranasal delivery of antigens may facilitate the invoking of a mucosal antibody response, which is favoured by a shift in the T cell response toward the Th2 phenotype which helps antibody production. A mucosal response is characterised by enhanced IgA production, and a Th2 response is characterised by enhanced IL-4 production.

Intranasal delivery of mycobacterial antigens of the invention allows targeting of the antigens to sub-mucosal B cells of the respiratory system. These B cells are the major local IgA-producing cells in mammals and intranasal delivery facilitates a rapid increase in IgA production by these cells against the mycobacterial antigens.

Therapeutic formulations, medicaments and prophylactic formulations (eg. vaccines) of the invention comprise a pharmaceutically acceptable carrier, and optionally one or more of a salt, excipient, diluent and/or adjuvant.

In one embodiment, the immunogenic composition, therapeutic formulation, medicament or prophylactic formulation (eg. vaccine) of the invention may comprise one or more immunoregulatory agents selected from, for example, immunoglobulins, antibiotics, interleukins (eg. IL-2, IL-12), and/or cytokines (eg. IFNγ).

In one embodiment, the immunogenic composition, therapeutic formulation, medicament or prophylactic formulation (eg. vaccine) of the invention may comprise one or more antimicrobial compounds, such as conventional anti-tuberculosis drugs (eg. rifampicin, isoniazid, ethambutol or pyrizinamide).

The therapeutic formulation, medicament or prophylactic formulation (eg. a vaccine) of the invention may be given in a single dose schedule (ie. the full dose is given at substantially one time). Alternatively, the therapeutic formulation, medicament or prophylactic formulation (eg. a vaccine) of the invention may be given in a multiple dose schedule.

A multiple dose schedule is one in which a primary course of treatment (eg. vaccination) may be with 1-6 separate doses, followed by other doses given at subsequent time intervals required to maintain and or reinforce the immune response, for example (for human subjects), at 1-4 months for a second dose, and if needed, a subsequent dose(s) after a further 1-4 months.

The dosage regimen will be determined, at least in part, by the need of the individual and be dependent upon the judgment of the practitioner (eg. doctor or veterinarian).

Simultaneous administration means administration at (substantially) the same time.

Sequential administration of two or more compositions/therapeutic agents/vaccines means that the compositions/therapeutic agents/vaccines are administered at (substantially) different times, one after the other.

For example, in one embodiment, the vaccine of the present invention may be administered as part of a 'prime-boost' vaccination regime.

Prime-boost vaccination regimes involve: Priming—ie. exposing a subject to one or more antigens or a vaccine; and subsequently: Boosting—ie. exposing the subject to one or more antigens or a vaccine. The 'boost' antigens/vaccine is typically different from the 'primer' antigens/vaccine (known as "heterologous" prime-boost). In this regard, heterologous prime-boost immunization strategies have been shown to induce higher levels of effector T cell responses in subjects as compared with homologous boosting with the same vaccine. For example, repeated vaccination with conventional vaccines such as BCG does not appear to further enhance protection against TB. However, incorporating BCG into a heterologous prime-boost regime may retain the protective effects of BCG.

Thus, in one embodiment the invention provides a method of vaccination against mycobacterial infection comprising 'priming' a subject's immune system by administration of a heterologous conventional vaccine (eg. BCG vaccine) and then 'boosting' the subject's immune system by administration of the vaccine of the present invention. In one embodiment, the invention provides a method of vaccination against mycobacterial infection comprising administering the vaccine of the present invention to a subject that has been pre-exposed to a heterologous conventional vaccine such as BCG.

Alternatively, a subject's immune system may be 'primed' by administration of the vaccine of the present invention, and then 'boosted' by administration of a heterologous conventional vaccine (eg. BCG vaccine). Accordingly, in one embodiment, the vaccine is administered to a subject that is subsequently to be exposed to a heterologous conventional vaccine such as BCG.

The 'priming' step may be carried out on the subject at any age—in the case of mammalian subjects (eg. humans, cows, pigs, horses, badgers, foxes, sheep, goats, crows, dogs or cats), priming with BCG is conventionally carried out neonatally, or during infancy, adolescence or adulthood. The 'boosting' step may be carried out at any time after the 'priming' step. In the case of mammalian subjects (eg. humans, cows, pigs, horses, badgers, foxes, sheep, goats, crows, dogs or cats), a boosting step may be carried out at least about 1, 2, 3, 4, 5, 6, 7, 8, 9 or 10 weeks after the priming step, or at least about 2, 4, 6, 8, 10, 12, 14, 16, 18, 20, 22, 24, 26, 30, 33, 36, 39, 40, 44, 48, 50, 54 or 60 months after the priming step, or at least about 1, 2, 3, 4, or 5, or even 10, 15, 20, 25, 30, 35, or 40 or more years after the boosting step. In one embodiment, for a human subject, the priming step is carried out during infancy and the boosting step is carried out during adolescence.

In one embodiment, the therapeutic formulation, medicament or prophylactic formulation (eg. a vaccine) of the invention can be administered to a subject such as a mammal (eg. a human, bovine, porcine, ovine, caprine, equine, corvine, canine or feline subject) in conjunction with (simultaneously or sequentially) one or more immunoregulatory agents selected from, for example, immunoglobulins, antibiotics, interleukins (eg. IL-2, IL-12), and/or cytokines (eg. IFNγ).

In one embodiment, the therapeutic formulation, medicament or prophylactic formulation (eg. vaccine) of the invention can be administered to a subject such as a mammal (eg. a human, bovine, porcine, ovine, caprine, equine, corvine, canine or feline subject) in conjunction with (simultaneously or sequentially) one or more antimicrobial compounds, such as conventional anti-tuberculosis drugs (eg. rifampicin, isoniazid, ethambutol or pyrizinamide).

The therapeutic formulation, medicament or prophylactic formulation (eg. vaccine) may contain 5% to 95% of active ingredient, such as at least 10% or 25% of active ingredient, or at least 40% of active ingredient or at least 50, 55, 60, 70 or 75% active ingredient.

The therapeutic formulation, medicament or prophylactic formulation (eg. a vaccine) is administered in a manner compatible with the dosage formulation, and in such amount as will be prophylactically and/or therapeutically effective.

In this regard, as used herein, an "effective amount" is a dosage or amount that is sufficient to achieve a desired biological outcome. As used herein, a "therapeutically effective amount" is an amount which is effective, upon single or multiple dose administration to a subject (such as a mammal—eg. human, a cow, a pig, a horse, a badger, a fox, a sheep, a goat, a crow, a dog or a cat) for treating, preventing, curing, delaying, reducing the severity of, ameliorating at least one symptom of a disorder or recurring disorder, or prolonging the survival of the subject beyond that expected in the absence of such treatment.

Accordingly, the quantity of active ingredient to be administered, which is generally in the range of 5 micrograms to 250 micrograms of antigen per dose (or higher if delivered orally or in the form of viral vectors), depends on the subject to be treated, capacity of the subject's immune system to generate a protective immune response, and the degree of protection desired. Precise amounts of active ingredient required to be administered may depend on the judgment of the practitioner and may be particular to each subject.

The present invention encompasses polypeptides that are substantially homologous to polypeptides based on any one of the reference SEQ ID NOs identified in this application (including fragments thereof). The terms "sequence identity" and "sequence homology" are considered synonymous in this specification.

By way of example, a polypeptide of interest may comprise an amino acid sequence having at least 70, 75, 80, 82, 84, 86, 88, 90, 92, 94, 96, 98, 99 or 100% amino acid sequence identity with the amino acid sequence of a reference polypeptide.

There are many established algorithms available to align two amino acid sequences.

Typically, one sequence acts as a reference sequence, to which test sequences may be compared. The sequence comparison algorithm calculates the percentage sequence identity for the test sequence(s) relative to the reference sequence, based on the designated program parameters. Alignment of amino acid sequences for comparison may be conducted, for example, by computer implemented algorithms (eg. GAP, BESTFIT, FASTA or TFASTA), or BLAST and BLAST 2.0 algorithms.

The BLOSUM62 table shown below is an amino acid substitution matrix derived from about 2,000 local multiple alignments of protein sequence segments, representing highly conserved regions of more than 500 groups of related proteins (Henikoff & Henikoff, Proc. Natl. Acad. Sci. USA 89:10915-10919, 1992; incorporated herein by reference). Amino acids are indicated by the standard one-letter codes. The percent identity is calculated as:

$$\frac{\text{(Total number of identical matches)}}{\begin{array}{c}\text{[length of the longer sequences plus the}\\ \text{number of gaps Introduced into the longer}\\ \text{sequence in order to align the two sequences]}\end{array}}\times 100$$

BLOSUM62 Table

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | −1 | 5 | | | | | | | | | | | | | | | | | | |
| N | −2 | 0 | 6 | | | | | | | | | | | | | | | | | |
| D | −2 | −2 | 1 | 6 | | | | | | | | | | | | | | | | |
| C | 0 | −3 | −3 | −3 | 9 | | | | | | | | | | | | | | | |
| Q | −1 | 1 | 0 | 0 | −3 | 5 | | | | | | | | | | | | | | |
| E | −1 | 0 | 0 | 2 | −4 | 2 | 5 | | | | | | | | | | | | | |
| G | 0 | −2 | 0 | −1 | −3 | −2 | −2 | 6 | | | | | | | | | | | | |

-continued

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| H | −2 | 0 | 1 | −1 | −3 | 0 | 0 | −2 | 8 | | | | | | | | | | | |
| I | −1 | −3 | −3 | −3 | −1 | −3 | −3 | −4 | −3 | 4 | | | | | | | | | | |
| L | −1 | −2 | −3 | −4 | −1 | −2 | −3 | −4 | −3 | 2 | 4 | | | | | | | | | |
| K | −1 | 2 | 0 | −1 | −3 | 1 | 1 | −2 | −1 | −3 | −2 | 5 | | | | | | | | |
| M | −1 | −1 | −2 | −3 | −1 | 0 | −2 | −3 | −2 | 1 | 2 | −1 | 5 | | | | | | | |
| F | −2 | −3 | −3 | −3 | −2 | −3 | −3 | −3 | −1 | 0 | 0 | −3 | 0 | 6 | | | | | | |
| P | −1 | −2 | −2 | −1 | −3 | −1 | −1 | −2 | −2 | −3 | −3 | −1 | −2 | −4 | 7 | | | | | |
| S | 1 | −1 | 1 | 0 | −1 | 0 | 0 | 0 | −1 | −2 | −2 | 0 | −1 | −2 | −1 | 4 | | | | |
| T | 0 | −1 | 0 | −1 | −1 | −1 | −1 | −2 | −2 | −1 | −1 | −1 | −1 | −2 | −1 | 1 | 5 | | | |
| W | −3 | −3 | −4 | −4 | −2 | −2 | −3 | −2 | −2 | −3 | −2 | −3 | −1 | 1 | −4 | −3 | −2 | 11 | | |
| Y | −2 | −2 | −2 | −3 | −2 | −1 | −2 | −3 | 2 | −1 | −1 | −2 | −1 | 3 | −3 | −2 | −2 | 2 | 7 | |
| V | 0 | −3 | −3 | −3 | −1 | −2 | −2 | −3 | −3 | 3 | 1 | −2 | 1 | −1 | −2 | −2 | 0 | −3 | −1 | 4 |

In a homology comparison, the identity may exist over a region of the sequences that is at least 10 amino acid residues in length (eg. at least 15, 20, 30, 40, 50, 75, 100, 150, 200, 250, 300, 350, 400, 450, 500, 550, 600, 650 or 685 amino acid residues in length—eg. up to the entire length of the reference sequence.

Substantially homologous polypeptides have one or more amino acid substitutions, deletions, or additions. In many embodiments, those changes are of a minor nature, for example, involving only conservative amino acid substitutions. Conservative substitutions are those made by replacing one amino acid with another amino acid within the following groups: Basic: arginine, lysine, histidine; Acidic: glutamic acid, aspartic acid; Polar: glutamine, asparagine; Hydrophobic: leucine, isoleucine, valine; Aromatic: phenylalanine, tryptophan, tyrosine; Small: glycine, alanine, serine, threonine, methionine. Substantially homologous polypeptides also encompass those comprising other substitutions that do not significantly affect the folding or activity of the polypeptide; small deletions, typically of 1 to about 30 amino acids (such as 1-10, or 1-5 amino acids); and small amino- or carboxyl-terminal extensions, such as an amino-terminal methionine residue, a small linker peptide of up to about 20-25 residues, or an affinity tag.

The polypeptides of the invention may also comprise non-naturally occurring amino acid residues. In this regard, in addition to the 20 standard amino acids, non-standard amino acids (such as 4-hydroxyproline, 6-N-methyl lysine, 2-aminoisobutyric acid, isovaline and α-methyl serine) may be substituted for amino acid residues of the mycobacterial polypeptides of the present invention. A limited number of non-conservative amino acids, amino acids that are not encoded by the genetic code, and unnatural amino acids may be substituted for mycobacterial polypeptide amino acid residues. Non-naturally occurring amino acids include, without limitation, trans-3-methylproline, 2,4-methano-proline, cis-4-hydroxyproline, trans-4-hydroxy-proline, N-methylglycine, allo-threonine, methyl-threonine, hydroxy-ethylcysteine, hydroxyethylhomo-cysteine, nitro-glutamine, homoglutamine, pipecolic acid, tert-leucine, norvaline, 2-azaphenylalanine, 3-azaphenyl-alanine, 4-azaphenyl-alanine, and 4-fluorophenylalanine.

Several methods are known in the art for incorporating non-naturally occurring amino acid residues into polypeptides. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations can be carried out in a cell free system comprising an *E. coli* S30 extract and commercially available enzymes and other reagents. Peptides can be, for instance, purified by chromatography. In a second method, translation is carried out in Xenopus oocytes by microinjection of mutated mRNA and chemically aminoacylated suppressor tRNAs. Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3azaphenylalanine, 4-azaphenylalanine, or 4-fluorophenylalanine). The non-naturally occurring amino acid is incorporated into the polypeptide in place of its natural counterpart. Naturally occurring amino acid residues can be converted to non-naturally occurring species by in vitro chemical modification. Chemical modification can be combined with site-directed mutagenesis to further expand the range of substitutions.

Essential amino acids, such as those in the polypeptides of the present invention, can be identified according to procedures known in the art, such as site-directed mutagenesis or alanine-scanning mutagenesis. Sites of biological interaction can also be determined by physical analysis of structure, as determined by such techniques as nuclear magnetic resonance, crystallography, electron diffraction or photoaffinity labeling, in conjunction with mutation of putative contact site amino acids. The identities of essential amino acids can also be inferred from analysis of homologies with related family members of the polypeptide of interest.

Multiple amino acid substitutions can be made and tested using known methods of mutagenesis and screening. Methods are known for simultaneously randomizing two or more positions in a polypeptide, selecting for functional polypeptide, and then sequencing the mutagenized polypeptides to determine the spectrum of allowable substitutions at each position. Other methods that can be used include phage display.

Routine deletion analyses of nucleic acid molecules can be performed to obtain functional fragments of a nucleic acid molecule that encodes a polypeptide of the invention. As an illustration, DNA molecules can be digested with Bal31 nuclease to obtain a series of nested deletions. These DNA fragments are then inserted into expression vectors in proper reading frame, and the expressed polypeptides are isolated and tested for the desired activity. An alternative to exonuclease digestion is to use oligonucleotide-directed mutagenesis to introduce deletions, or stop codons to specify production of a desired fragment. Alternatively, particular polynucleotide fragments can be synthesized using the polymerase chain reaction.

A mutant of a polypeptide of the invention may contain one or more analogs of an amino acid (eg. an unnatural amino acid), or a substituted linkage, as compared with the sequence of the reference polypeptide. In a further embodiment, a polypeptide of interest may be a mimic of the reference polypeptide, which mimic reproduces at least one epitope of the reference polypeptide.

Mutants of the disclosed polynucleotide and polypeptide sequences of the invention can be generated through DNA shuffling. Briefly, mutant DNAs are generated by in vitro homologous recombination by random fragmentation of a parent DNA followed by reassembly using PCR, resulting in randomly introduced point mutations. This technique can be modified by using a family of parent DNAs, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed above can be combined with high-throughput screening methods to detect activity of cloned mutant polypeptides. Mutagenized nucleic acid molecules that encode polypeptides of the invention, or fragments thereof, can be recovered from the host cells and rapidly sequenced using modern equipment. These methods allow the rapid determination of the importance of individual amino acid residues in a polypeptide of interest, and can be applied to polypeptides of unknown structure.

A "fragment" of a polypeptide of interest comprises a series of consecutive amino acid residues from the sequence of said polypeptide. By way of example, a "fragment" of a polypeptide of interest may comprise (or consist of) at least 10 consecutive amino acid residues from the sequence of said polypeptide (eg. at least 15, 20, 25, 28, 30, 35, 40, 45, 50, 55, 75, 100, 125, 150, 175, 200, 225, 250, 275, 300, 325, 350, 375, 400 or 412 consecutive amino acid residues of said polypeptide). A fragment may include at least one epitope of the polypeptide of interest.

A polypeptide of interest, or fragment, may possess the active site of the reference polypeptide.

The polypeptide of interest, or fragment thereof, may have a common antigenic cross-reactivity and/or substantially the same in vivo biological activity as the reference peptide. For example, the polypeptides, or polypeptide fragments, and reference polypeptides share a common ability to induce a "recall response" of a T-lymphocyte (eg. CD4+, CD8+, effector T cell or memory T cell such as a TEM or TCM), which has been previously exposed to an antigenic component of a mycobacterial infection.

New immunological assays for measuring and quantifying T cell responses have been established over the last 10 years. For example, the interferon-gamma (IFN-γ) ELISPOT assay is useful as an immunological readout because the secretion of IFN-γ from antigen-specific T cells is a good correlate of protection against *M. tuberculosis*. Furthermore, the ELISPOT assay is a very reproducible and sensitive method of quantifying the number of IFN-γ secreting antigen-specific T cells.

As used herein, the terms "nucleic acid sequence" and "polynucleotide" are used interchangeably and do not imply any length restriction. As used herein, the terms "nucleic acid" and "nucleotide" are used interchangeably. The terms "nucleic acid sequence" and "polynucleotide" embrace DNA (including cDNA) and RNA sequences. As used herein, the terms "amino acid sequence" and "polypeptide" are used interchangeably and do not imply any length restriction.

The polynucleotide sequences of the present invention include nucleic acid sequences that have been removed from their naturally occurring environment, recombinant or cloned DNA isolates, and chemically synthesized analogues or analogues biologically synthesized by heterologous systems.

The polynucleotides of the present invention may be prepared by any means known in the art. For example, large amounts of the polynucleotides may be produced by replication in a suitable host cell. The natural or synthetic DNA fragments coding for a desired fragment will be incorporated into recombinant nucleic acid constructs, typically DNA constructs, capable of introduction into and replication in a prokaryotic or eukaryotic cell. Usually the DNA constructs will be suitable for autonomous replication in a unicellular host, such as yeast or bacteria, but may also be intended for introduction to and integration within the genome of a cultured insect, mammalian, plant or other eukaryotic cell lines.

The polynucleotides of the present invention may also be produced by chemical synthesis, eg. by the phosphoramidite method or the triester method, and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence.

When applied to a nucleic acid sequence, the term "isolated" in the context of the present invention denotes that the polynucleotide sequence has been removed from its natural genetic milieu and is thus free of other extraneous or unwanted coding sequences (but may include naturally occurring 5' and 3' untranslated regions such as promoters and terminators), and is in a form suitable for use within genetically engineered protein production systems. Such isolated molecules are those that are separated from their natural environment.

Methods for isolating nucleic acid sequences are known in the art.

A nucleic acid sequence encoding a polypeptide of the invention can be obtained by conventional cloning procedures, such as PCR, or can be synthesized using nucleic acid synthesis machines. An alternative way to prepare a full-length polynucleotide is to synthesize a specified set of overlapping oligonucleotides (eg. 40 to 100 nucleotides), as described (for example) in Glick & Pasternak, Molecular Biotechnology, Principles & Applications of Recombinant DNA, (1994). Other sequences may be added that contain signals for proper initiation and termination of transcription and translation.

In view of the degeneracy of the genetic code, considerable sequence variation is possible among the polynucleotides of the present invention. Degenerate codons encompassing all possible codons for a given amino acid are set forth below:

| Amino Acid | Codons | Degenerate Codon |
|---|---|---|
| Cys | TGC TGT | TGY |
| Ser | AGC AGT TCA TCC TCG TCT | WSN |
| Thr | ACA ACC ACG ACT | ACN |
| Pro | CCA CCC CCG CCT | CCN |
| Ala | GCA GCC GCG GCT | GCN |
| Gly | GGA GGC GGG GGT | GGN |
| Asn | AAC AAT | AAY |
| Asp | GAC GAT | GAY |
| Glu | GAA GAG | GAR |
| Gln | CAA CAG | CAR |
| His | CAC CAT | CAY |
| Arg | AGA AGG CGA CGC CGG CGT | MGN |
| Lys | AAA AAG | AAR |
| Met | ATG | ATG |
| Ile | ATA ATC ATT | ATH |
| Leu | CTA CTC CTG CTT TTA TTG | YTN |

-continued

| Amino Acid | Codons | Degenerate Codon |
|---|---|---|
| Val | GTA GTC GTG GTT | GTN |
| Phe | TTC TTT | TTY |
| Tyr | TAC TAT | TAY |
| Trp | TGG | TGG |
| Ter | TAA TAG TGA | TRR |
| Asn/Asp | | RAY |
| Glu/Gln | | SAR |
| Any | | NNN |

One of ordinary skill in the art will appreciate that some ambiguity is introduced in determining a degenerate codon, representative of all possible codons encoding each amino acid. For example, some polynucleotides encompassed by the degenerate sequence may encode variant amino acid sequences, but one of ordinary skill in the art can easily identify such variant sequences by reference to the amino acid sequences of the present invention.

A "variant" nucleic acid sequence has substantial homology or substantial similarity to a reference nucleic acid sequence (or a fragment thereof). A nucleic acid sequence or fragment thereof is "substantially homologous" (or "substantially identical") to a reference sequence if, when optimally aligned (with appropriate nucleotide insertions or deletions) with the other nucleic acid (or its complementary strand), there is nucleotide sequence identity in at least about 70%, 75%, 80%, 82, 84, 86, 88, 90, 92, 94, 96, 98 or 99% of the nucleotide bases. Homology determination is performed as described supra for polypeptides.

Alternatively, a "variant" nucleic acid sequence is substantially homologous with (or substantially identical to) a reference sequence (or a fragment thereof) if the "variant" and the reference sequence they are capable of hybridizing under stringent (eg. highly stringent) hybridization conditions. Nucleic acid sequence hybridization will be affected by such conditions as salt concentration (eg. NaCl), temperature, or organic solvents, in addition to the base composition, length of the complementary strands, and the number of nucleotide base mismatches between the hybridizing nucleic acids, as will be readily appreciated by those skilled in the art. Stringent temperature conditions are preferably employed, and generally include temperatures in excess of 30° C., typically in excess of 37° C. and preferably in excess of 45° C. Stringent salt conditions will ordinarily be less than 1000 mM, typically less than 500 mM, and preferably less than 200 mM. The pH is typically between 7.0 and 8.3. The combination of parameters is much more important than any single parameter.

One of ordinary skill in the art appreciates that different species exhibit "preferential codon usage". As used herein, the term "preferential codon usage" refers to codons that are most frequently used in cells of a certain species, thus favoring one or a few representatives of the possible codons encoding each amino acid. For example, the amino acid threonine (Thr) may be encoded by ACA, ACC, ACG, or ACT, but in mammalian host cells ACC is the most commonly used codon; in other species, different Thr codons may be preferential. Preferential codons for a particular host cell species can be introduced into the polynucleotides of the present invention by a variety of methods known in the art. Conventional methods for codonoptimization are well known in the art and are routine techniques within the ordinary level of a person skilled in the art. By way of example, there exists an abundance of freely available software tools for codon-optimizing a sequence of interest for expression in a particular host. OPTIMIZER is just such a tool and is available at the OPTIMIZER website (Puigbo et al. Nucl. Acids Res. (2007) 35 (suppl 2): W126-W131). Introduction of preferential codon sequences into recombinant DNA can, for example, enhance production of the protein by making protein translation more efficient within a particular cell type or species.

Thus, in one embodiment of the invention, the nucleic acid sequence is codon optimized for expression in a host cell.

A "fragment" of a polynucleotide of interest comprises a series of consecutive amino acid residues from the sequence of said full-length polynucleotide. By way of example, a "fragment" of a polynucleotide of interest may comprise (or consist of) at least 30 consecutive nucleic acid residues from the sequence of said polypeptide (eg. at least 35, 50, 75, 100, 150, 200, 250, 300, 350, 400, 450, 500, 550, 600, 650, 700, 750, 800 850, 900, 950, 1000, 1050, 1100, 1150 or 1200 consecutive nucleic acid residues of said polynucleotide). A fragment may include at least one antigenic determinant and/or may encode at least one antigenic epitope of the corresponding polypeptide of interest.

A polynucleotide of interest, or variant or fragment thereof, may encode a polypeptide that has a common antigenic cross-reactivity and/or substantially the same in vivo biological activity as a reference peptide.

For example, polypeptides encoded by the polynucleotide (or fragment or variant), and the reference polynucleotide may share a common ability to induce a "recall response" of a T-lymphocyte (eg. CD4+, CD8+, effector T cell or memory T cell such as a TEM or TCM), which has been previously exposed to an antigenic component of a mycobacterial infection.

New immunological assays for measuring and quantifying T cell responses have been established over the last 10 years. For example, the interferon-gamma (IFN-γ) ELISPOT assay is useful as an immunological readout because the secretion of IFN-γ from antigen-specific T cells is a good correlate of protection against *M. tuberculosis*. Furthermore, the ELISPOT assay is a very reproducible and sensitive method of quantifying the number of IFN-γ secreting antigen-specific T cells.

Alternatively, or in addition, an antibody capable of binding to a polypeptide encoded by the polynucleotide of interest, or fragment or variant, may be also capable of binding to a polypeptide encoded by the reference polynucleotide.

Key to SEQ ID NOs

| | |
|---|---|
| SEQ ID NO: 1 | Hybrid C4bp oligomerization domain amino acid sequence (IMX313) |
| SEQ ID NO: 2 | Hybrid C4bp oligomerization domain polynucleotide sequence encoding peptide IMX313 |
| SEQ ID NO: 3 | Mycobacterial peptide 85A/Rv3804c |
| SEQ ID NO: 4 | Mycobacterial peptide 85B/Rv1886c |
| SEQ ID NO: 5 | Mycobacterial peptide 85C/Rv0129c |
| SEQ ID NO: 6 | Mycobacterial peptide ESAT6/Rv3875 |
| SEQ ID NO: 7 | Mycobacterial peptide TB10.4/Rv0288 |
| SEQ ID NO: 8 | Mycobacterial peptide Rv0125 |

-continued

| | |
|---|---|
| SEQ ID NO: 9 | Mycobacterial peptide PPE18/Rv1196 |
| SEQ ID NO: 10 | Mycobacterial peptide P27/Rv1411c |
| SEQ ID NO: 11 | Mycobacterial peptide HSP65/Rv0440 |
| SEQ ID NO: 12 | Mycobacterial peptide HBHA/Rv0475 |
| SEQ ID NO: 13 | Mycobacterial peptide Rv2659c |
| SEQ ID NO: 14 | Mycobacterial peptide Rv2660c |
| SEQ ID NO: 15 | Mycobacterial peptide HspX/Rv2031c |
| SEQ ID NO: 16 | Mycobacterial peptide RPFA/Rv0867c |
| SEQ ID NO: 17 | Mycobacterial peptide RPFB/Rv1009 |
| SEQ ID NO: 18 | Mycobacterial peptide RPFC/Rv1884c |
| SEQ ID NO: 19 | Mycobacterial peptide RPFD/Rv2389c |
| SEQ ID NO: 20 | Mycobacterial peptide RPFE/Rv2450c |
| SEQ ID NO: 21 | Mycobacterial peptide Rv1733c |
| SEQ ID NO: 22 | Mycobacterial peptide Rv2029c |
| SEQ ID NO: 23 | Mycobacterial peptide Rv2032 |
| SEQ ID NO: 24 | Mycobacterial peptide Rv2626c |
| SEQ ID NO: 25 | Mycobacterial peptide Rv2627c |
| SEQ ID NO: 26 | Mycobacterial peptide Rv2628 |
| SEQ ID NO: 27 | Mycobacterial polynucleotide encoding peptide 85A |
| SEQ ID NO: 28 | Mycobacterial polynucleotide encoding peptide 85B |
| SEQ ID NO: 29 | Mycobacterial polynucleotide encoding peptide 85C |
| SEQ ID NO: 30 | Mycobacterial polynucleotide encoding peptide ESAT6 |
| SEQ ID NO: 31 | Mycobacterial polynucleotide encoding peptide TB10.4 |
| SEQ ID NO: 32 | Mycobacterial polynucleotide encoding peptide Rv0125 |
| SEQ ID NO: 33 | Mycobacterial polynucleotide encoding peptide Rv1196 |
| SEQ ID NO: 34 | Mycobacterial polynucleotide encoding peptide Rv1411 |
| SEQ ID NO: 35 | Mycobacterial polynucleotide encoding peptide HSP65 |
| SEQ ID NO: 36 | Mycobacterial polynucleotide encoding peptide HBHA |
| SEQ ID NO: 37 | Mycobacterial polynucleotide encoding peptide Rv2659c |
| SEQ ID NO: 38 | Mycobacterial polynucleotide encoding peptide Rv2660c |
| SEQ ID NO: 39 | Mycobacterial polynucleotide encoding peptide HspX/Rv2031c |
| SEQ ID NO: 40 | Mycobacterial polynucleotide encoding peptide RPFA/Rv0867c |
| SEQ ID NO: 41 | Mycobacterial polynucleotide encoding peptide RPFB/Rv1009 |
| SEQ ID NO: 42 | Mycobacterial polynucleotide encoding peptide RPFC/Rv1884c |
| SEQ ID NO: 43 | Mycobacterial polynucleotide encoding peptide RPFD/Rv2389c |
| SEQ ID NO: 44 | Mycobacterial polynucleotide encoding peptide RPFE/Rv2450c |
| SEQ ID NO: 45 | Mycobacterial polynucleotide encoding peptide Rv1733c |
| SEQ ID NO: 46 | Mycobacterial polynucleotide encoding peptide Rv2029c |
| SEQ ID NO: 47 | Mycobacterial polynucleotide encoding peptide Rv2032 |
| SEQ ID NO: 48 | Mycobacterial polynucleotide encoding peptide Rv2626c |
| SEQ ID NO: 49 | Mycobacterial polynucleotide encoding peptide Rv2627c |
| SEQ ID NO: 50 | Mycobacterial polynucleotide encoding peptide Rv2628 |
| SEQ ID NO: 51 | Codon-optimized Mycobacterial polynucleotide encoding peptide 85A |
| SEQ ID NO: 52 | Mycobacterial peptide 85A encoded by SEQ ID NO: 51 |
| SEQ ID NO: 53 | Codon-optimized hybrid C4bp oligomerization domain polynucleotide sequence encoding peptide IMX313 |
| SEQ ID NO: 54 | Codon-optimized nucleotide sequence encoding fusion protein of Mycobacterial peptide 85A and IMX313 peptide with gly-ser linker |
| SEQ ID NO: 55 | Fusion protein of Mycobacterial peptide 85A and IMX313 peptide with gly-ser linker encoded by SEQ ID NO: 55 |
| SEQ ID NO: 56 | Codon-optimized nucleotide sequence of SEQ ID NO: 27 |

SEQ ID NO: 57 Mycobacterial polynucleotide encoding peptide oIMX1027 SEQ ID NO: 58 Mycobacterial polynucleotide encoding peptide oIMX1028 SEQ ID NO: 59 Mycobacterial polynucleotide encoding peptide 85 AN SEQ ID NO: 60 Mycobacterial polynucleotide encoding peptide 85 AC

SEQ ID NO: 1

KKQGDADVCGEVAYIQSVVSDCHVPTAELRTLLEIRKLFLEIQKLKVELQGLSKE

SEQ ID NO: 2

AAGAAGCAAGGTGATGCTGATGTGTGCGGAGAGGTTGCTTATATTCAGAGCGTCGTCTCCGATTGCCACGTGCCT

ACAGCGGAACTGCGTACTCTGCTGGAAATACGAAAACTCTTCCTGGAGATTCAAAAACTGAAGGTGGAATTGCAA

GGACTGAGCAAGGAGTAATAA

SEQ ID NO: 3

MQLVDRVRGAVTGMSRRLVVGAVGAALVSGLVGAVGGTATAGAFSRPGLPVEYLQVPSPS

MGRDIKVQFQSGGANSPALYLLDGLRAQDDFSGWDINTPAFEWYDQSGLSVVMPVGGQSS

FYSDWYQPACGKAGCQTYKWETFLTSELPGWLQANRHVKPTGSAVVGLSMAASSALTLAI

YHPQQFVYAGAMSGLLDPSQAMGPTLIGLAMGDAGGYKASDMWGPKEDPAWQRNDPLLNV

-continued

GKLIANNTRVWVYCGNGKPSDLGGNNLPAKFLEGFVRTSNIKFQDAYNAGGGHNGVFDFP

DSGTHSWEYWGAQLNAMKPDLQRALGATPNTGPAPQGA

SEQ ID NO: 4

MTDVSRKIRAWGRRLMIGTAAAVVLPGLVGLAGGAATAGAFSRPGLPVEYLQVPSPSMGR

DIKVQFQSGGNNSPAVYLLDGLRAQDDYNGWDINTPAFEWYYQSGLSIVMPVGGQSSFYS

DWYSPACGKAGCQTYKWETFLTSELPQWLSANRAVKPTGSAAIGLSMAGSSAMILAAYHP

QQFIYAGSLSALLDPSQGMGPSLIGLAMGDAGGYKAADMWGPSSDPAWERNDPTQQIPKL

VANNTRLWVYCGNGTPNELGGANIPAEFLENFVRSSNLKFQDAYNAAGGHNAVFNFPPNG

THSWEYWGAQLNAMKGDLQSSLGAG

SEQ ID NO 5

MTFFEQVRRLRSAATTLPRRLAIAAMGAVLVYGLVGTFGGPATAGAFSRPGLPVEYLQVPSASMGRDIKVQFQGG

GPHAVYLLDGLRAQDDYNGWDINTPAFEEYYQSGLSVIMPVGGQSSFYTDWYQPSQSNGQNYTYKWETFLTREMP

AWLQANKGVSPTGNAAVGLSMSGGSALILAAYYPQQFPYAASLSGFLNPSEGWWPTLIGLAMNDSGGYNANSMWG

PSSDPAWKRNDPMVQIPRLVANNTRIWVYCGNGTPSDLGGDNIPAKFLEGLTLRTNQTFRDTYAADGGRNGVFNF

PPNGTHSWPYWNEQLVAMKADIQHVLNGATPPAAPAAPAA

SEQ ID NO: 6

MTEQQWNFAGIEAAASAIQGNVTSIHSLLDEGKQSLTKLAAAWGGSGSEAYQGVQQKWDA

TATELNNALQNLARTISEAGQAMASTEGNVTGMFA

SEQ ID NO: 7

MSQIMYNYPAMLGHAGDMAGYAGTLQSLGAEIAVEQAALQSAWQGDTGITYQAWQAQWNQ

AMEDLVRAYHAMSSTHEANTMAMMARDTAEAAKWGG

SEQ ID NO: 8

MSNSRRRSLRWSWLLSVLAAVGLGLATAPAQAAPPALSQDRFADFPALPLDPSAMVAQVG

PQVVNINTKLGYNNAVGAGTGIVIDPNGVVLTNNHVIAGATDINAFSVGSGQTYGVDVVG

YDRTQDVAVLQLRGAGGLPSAAIGGGVAVGEPVVAMGNSGGQGGTPRAVPGRVVALGQTV

QASDSLTGAEETLNGLIQFDAAIQPGDSGGPVVNGLGQVVGMNTAASDNFQLSQGGQGFA

IPIGQAMAIAGQIRSGGGSPTVHIGPTAFLGLGVVDNNGNGARVQRVVGSAPAASLGIST

GDVITAVDGAPINSATAMADALNGHHPGDVISVTWQTKSGGTRTGNVTLAEGPPA

SEQ ID NO: 9

MVDFGALPPEINSARMYAGPGSASLVAAAQMWDSVASDLFSAASAFQSVVWGLTVGSWIG

SSAGLMVAAASPYVAWMSVTAGQAELTAAQVRVAAAAYETAYGLTVPPPVIAENRAELMI

LIATNLLGQNTPAIAVNEAEYGEMWAQDAAAMFGYAAATATATATLLPFEEAPEMTSAGG

LLEQAAAVEEASDTAAANQLMNNVPQALQQLAQPTQGTTPSSKLGGLWKTVSPHRSPISN

MVSMANNHMSMTNSGVSMTNTLSSMLKGFAPAAAAQAVQTAAQNGVRAMSSLGSSLGSSG

LGGGVAANLGRAASVGSLSVPQAWAAANQAVTPAARALPLTSLTSAAERGPGQMLGGLPV

GQMGARAGGGLSGVLRVPPRPYVMPHSPAAG

SEQ ID NO: 10

MRTPRRHCRRIAVLAAVSIAATVVAGCSSGSKPSGGPLPDAKPLVEEATAQTKALKSAHM

VLTVNGKIPGLSLKTLSGDLTTNPTAATGNVKLTLGGSDIDADFVVFDGILYATLTPNQW

SDFGPAADIYDPAQVLNPDTGLANVLANFADAKAEGRDTINGQNTIRISGKVSAQAVNQI

APPFNATQPVPATVWIQETGDHQLAQAQLDRGSGNSVQMTLSKWGEKVQVTKPPVS

SEQ ID NO: 11

MAKTIAYDEEARRGLERGLNALADAVKVTLGPKGRNVVLEKKWGAPTITNDGVSTAKEIE

LEDPYEKIGAELVKEVAKKTDDVAGDGTTTATVLAQALVREGLRNVAAGANPLGLKRGIE

-continued

KAVEKVTETLLKGAKEVETKEQIAATAAISAGDQSIGDLIAEAMDKVGNEGVITVEESNT

FGLQLELTEGMRFDKGYISGYFVTDPERQEAVLEDPYILLVSSKVSTVKDLLPLLEKVIG

AGKPLLIIAEDVEGEALSTLVVNKIRGTFKSVAVKAPGFGDRRKAMLQDMAILTGGQVIS

EEVGLTLENADLSLLGKARKVVVTKDETTIVEGAGDTDAIAGRVAQIRQEIENSDSDYDR

EKLQERLAKLAGGVAVIKAGAATEVELKERKHRIEDAVRNAKAAVEEGIVAGGGVTLLQA

APTLDELKLEGDEATGANIVKVALEAPLKQIAFNSGLEPGVVAEKVRNLPAGHGLNAQTG

VYEDLLAAGVADPVKVTRSALQNAASIAGLFLTTEAVVADKPEKEKASVPGGGDMGGMDF

SEQ ID NO: 12

MAENSNIDDIKAPLLAALGAADLALATVNELITNLRERAEETRTDTRSRVEESRARLTKL

QEDLPEQLTELREKFTAEELRKAAEGYLEAATSRYNELVERGEAALERLRSQQSFEEVSA

RAEGYVDQAVELTQEALGTVASQTRAVGERAAKLVGIELPKKAAPAKKAAPAKKAAPAKK

AAAKKAPAKKAAAKKVTQK

SEQ ID NO: 13

VTQTGKRQRRKFGRIRQFNSGRWQASYTGPDGRVYIAPKTFNAKIDAEAWLTDRRREIDR

QLWSPASGQEDRPGAPFGEYAEGWLKQRGIKDRTRAHYRKLLDNHILATFADTDLRDITP

AAVRRWYATTAVGTPTMRAHSYSLLRAIMQTALADDLIDSNPCRISGASTARRVHKIRPA

TLDELETITKAMPDPYQAFVLMAAWLAMRYGELTELRRKDIDLHGEVARVRRAVVRVGEG

FKVTTPKSDAGVRDISIPPHLIPAIEDHLHKHVNPGRESLLFPSVNDPNRHLAPSALYRM

FYKARKAAGRPDLRVHDLRHSGAVLAASTGATLAELMQRLGHSTAGAALRYQHAAKGRDR

EIAALLSKLAENQEM

SEQ ID NO: 14

VIAGVDQALAATGQASQRAAGASGGVTVGVGVGTEQRNLSVVAPSQFTFSSRSPDFVDET

AGQSWCAILGLNQFH

SEQ ID NO: 15

MATTLPVQRHPRSLFPEFSELFAAFPSFAGLRPTFDTRLMRLEDEMKEGRYEVRAELPGV

DPDKDVDIMVRDGQLTIKAERTEQKDFDGRSEFAYGSFVRTVSLPVGADEDDIKATYDKG

ILTVSVAVSEGKPTEKHIQIRSTN

SEQ ID NO: 16

MSGRHRKPTTSNVSVAKIAFTGAVLGGGGIAMAAQATAATDGEWDQVARCESGGNWSINT

GNGYLGGLQFTQSTWAAHGGGEFAPSAQLASREQQIAVGERVLATQGRGAWPVCGRGLSN

ATPREVLPASAAMDAPLDAAAVNGEPAPLAPPPADPAPPVELAANDLPAPLGEPLPAAPA

DPAPPADLAPPAPADVAPPVELAVNDLPAPLGEPLPAAPADPAPPADLAPPAPADLAPPA

PADLAPPAPADLAPPVELAVNDLPAPLGEPLPAAPAELAPPADLAPASADLAPPAPADLA

PPAPAELAPPAPADLAPPAAVNEQTAPGDQPATAPGGPVGLATDLELPEPDPQPADAPPP

GDVTEAPAETPQVSNIAYTKKLWQAIRAQDVCGNDALDSLAQPYVIG

SEQ ID NO: 17

MLRLVVGALLLVLAFAGGYAVAACKTVTLTVDGTAMRVTTMKSRVIDIVEENGFSVDDRD

DLYPAAGVQVHDADTIVLRRSRPLQISLDGHDAKQVWTTASTVDEALAQLAMTDTAPAAA

SRASRVPLSGMALPVVSAKTVQLNDGGLVRTVHLPAPNVAGLLSAAGVPLLQSDHVVPAA

TAPIVEGMQIQVTRNRIKKVTERLPLPPNARRVEDPEMNMSREVVEDPGVPGTQDVTFAV

AEVNGVETGRLPVANVVVTPAHEAVVRVGTKPGTEVPPVIDGSIWDAIAGCEAGGNWAIN

TGNGYYGGVQFDQGTWEANGGLRYAPRADLATREEQIAVAEVTRLRQGWGAWPVCAARAG

AR

-continued

SEQ ID NO: 18

VHPLPADHGRSRCNRHPISPLSLIGNASATSGDMSSMTRIAKPLIKSAMAAGLVTASMSL
STAVAHAGPSPNWDAVAQCESGGNWAANTGNGKYGGLQFKPATWAAFGGVGNPAAASREQ
QIAVANRVLAEQGLDAWPTCGAASGLPIALWSKPAQGIKQIINEIIWAGIQASIPR

SEQ ID NO: 19

MTPGLLTTAGAGRPRDRCARIVCTVFIETAVVATMFVALLGLSTISSKADDIDWDAIAQC
ESGGNWAANTGNGLYGGLQISQATWDSNGGVGSPAAASPQQQIEVADNIMKTQGPGAWPK
CSSCSQGDAPLGSLTHILTFLAAETGGCSGSRDD

SEQ ID NO: 20

LKNARTTLIAAAIAGTLVTTSPAGIANADDAGLDPNAAAGPDAVGFDPNLPPAPDAAPVD
TPPAPEDAGFDPNLPPPLAPDFLSPPAEEAPPVPVAYSVNWDAIAQCESGGNWSINTGNG
YYGGLRFTAGTWRANGGSGSAANASREEQIRVAENVLRSQGIRAWPVCGRRG

SEQ ID NO: 21

MIATTRDREGATMITFRLRLPCRTILRVFSRNPLVRGTDRLEAVVMLLAVTVSLLTIPFA
AAAGTAVQDSRSHVYAHQAQTRHPATATVIDHEGVIDSNTTATSAPPRTKITVPARWVVN
GIERSGEVNAKPGTKSGDRVGIWVDSAGQLVDEPAPPARAIADAALAALGLWLSVAAVAG
ALLALTRAILIRVRNASWQHDIDSLFCTQR

SEQ ID NO: 22

MTEPAAWDEGKPRIITLTMNPALDITTSVDVVRPTEKMRCGAPRYDPGGGGINVARIVHV
LGGCSTALFPAGGSTGSLLMALLGDAGVPFRVIPIAASTRESFTVNESRTAKQYRFVLPG
PSLTVAEQEQCLDELRGAAASAAFVVASGSLPPGVAADYYQRVADICRRSSTPLILDTSG
GGLQHISSGVFLLKASVRELRECVGSELLTEPEQLAAAHELIDRGRAEVVVVSLGSQGAL
LATRHASHRFSSIPMTAVSGVGAGDAMVAAITVGLSRGWSLIKSVRLGNAAGAAMLLTPG
TAACNRDDVERFFELAAEPTEVGQDQYVWHPIVNPEASP

SEQ ID NO: 23

MPDTMVTTDVIKSAVQLACRAPSLHNSQPWRWIAEDHTVALFLDKDRVLYATDHSGREAL
LGCGAVLDHFRVAMAAAGTTANVERFPNPNDPLHLASIDFSPADFVTEGHRLRADAILLR
RTDRLPFAEPPDWDLVESQLRTTVTADTVRIDVIADDMRPELAAASKLTESLRLYDSSYH
AELFWWTGAFETSEGIPHSSLVSAAESDRVTFGRDFPVVANTDRRPEFGHDRSKVLVLST
YDNERASLLRCGEMLSAVLLDATMAGLATCTLTHITELHASRDLVAALIGQPATPQALVR
VGLAPEMEEPPPATPRRPIDEVFHVRAKDHR

SEQ ID NO: 24

MTTARDIMNAGVTCVGEHETLTAAAQYMREHDIGALPICGDDDRLHGMLTDRDIVIKGLA
AGLDPNTATAGELARDSIYYVDANASIQEMLNVMEEHQVRRVPVISEHRLVGIVTEADIA
RHLPEHAIVQFVKAICSPMALAS

SEQ ID NO: 25

MASSASDGTHERSAFRLSPPVLSGAMGPFMHTGLYVAQSWRDYLGQQPDKLPIARPTIAL
AAQAFRDEIVLLGLKARRPVSNHRVFERISQEVAAGLEFYGNRRWLEKPSGFFAQPPPLT
EVAVRKVKDRRRSFYRIFFDSGFTPHPGEPGSQRWLSYTANNREYALLLRHPEPRPWLVC
VHGTEMGRAPLDLAVFRAWKLHDELGLNIVMPVLPMHGPRGQGLPKGAVFPGEDVLDDVH
GTAQAVWDIRRLLSWIRSQEEESLIGLNGLSLGGYIASLVASLEEGLACAILGVPVADLI
ELLGRHCGLRHKDPRRHTVKMAEPIGRMISPLSLTPLVPMPGRFIYAGIADRLVHPREQV
TRLWEHWGKPEIVWYPGGHTGFFQSRPVRRFVQAALEQSGLLDAPRTQRDRSA

-continued

SEQ ID NO: 26

MSTQRPRHSGIRAVGPYAWAGRCGRIGRWGVHQEAMMNLAIWHPRKVQSATIYQVTDRSH

DGRTARVPGDEITSTVSGWLSELGTQSPLADELARAVRIGDWPAAYAIGEHLSVEIAVAV

SEQ ID NO: 27 atgcagcttgttgacagggttcgtggcgccgtcacgggtatgtcgcgtcgactcgtggtc ggggccgtcggcgcggccctagtgtcgggtctggtcggcgccgtcggtggcacggcgacc gcgggggcattttcccggccgggcttgccggtggagtacctgcaggtgccgtcgccgtcg atgggccgtgacatcaaggtccaattccaaagtggtggtgccaactcgcccgccctgtac ctgctcgacggcctgcgcgcgcaggacgacttcagcggctgggacatcaacaccccggcg ttcgagtggtacgaccagtcgggcctgtcggtggtcatgccggtgggtggccagtcaagc ttctactccgactggtaccagcccgcctgcggcaaggccggttgccagacttacaagtgg gagaccttcctgaccagcgagctgccggggtggctgcaggccaacaggcacgtcaagccc accggaagcgccgtcgtcggtctttcgatggctgcttcttcggcgctgacgctggcgatc tatcacccccagcagttcgtctacgcgggagcgatgtcgggcctgttggacccctcccag gcgatgggtcccaccctgatcggcctggcgatgggtgacgctggcggctacaaggcctcc gacatgtggggcccgaaggaggacccggcgtggcagcgcaacgacccgctgttgaacgtc gggaagctgatcgccaacaacacccgcgtctgggtgtactgcggcaacggcaagccgtcg gatctgggtggcaacaacctgccggccaagttcctcgagggcttcgtgcggaccagcaac atcaagttccaagacgcctacaacgccggtggcggccacaacggcgtgttcgacttcccg gacagcggtacgcacagctgggagtactggggcgcgcagctcaacgctatgaagcccgac ctgcaacgggcactgggtgccacgcccaacaccgggcccgcgccccagggcgcctag

SEQ ID NO: 28 atgacagacgtgagccgaaagattcgagcttggggacgccgattgatgatcggcacggca gcggctgtagtccttccgggcctggtggggcttgccggcggagcggcaaccgcgggcgcg ttctcccggccggggctgccggtcgagtacctgcaggtgccgtcgccgtcgatgggccgc gacatcaaggttcagttccagagcggtgggaacaactcacctgcggtttatctgctcgac ggcctgcgcgcccaagacgactacaacggctgggatatcaacaccccggcgttcgagtgg tactaccagtcgggactgtcgatagtcatgccggtcggcgggcagtccagcttctacagc gactggtacagcccggcctgcggtaaggctggctgccagacttacaagtgggaaaccttc ctgaccagcgagctgccgcaatggttgtccgccaacagggccgtgaagcccaccggcagc gctgcaatcggcttgtcgatggccggctcgtcggcaatgatcttggccgcctaccacccc cagcagttcatctacgccggctcgctgtcggccctgctggacccctctcaggggatgggg cctagcctgatcggcctcgcgatgggtgacgccggcggttacaaggccgcagacatgtgg ggtccctcgagtgacccggcatgggagcgcaacgaccctacgcagcagatccccaagctc gtcgcaaacaacacccggctatgggtttattgcgggaacggcaccccgaacgagttgggc ggtgccaacatacccgccgagttcttggagaacttcgttcgtagcagcaacctgaagttc caggatgcgtacaacgccgcgggcgggcacaacgccgtgttcaacttcccgcccaacggc acgcacagctgggagtactggggcgctcagctcaacgccatgaagggtgacctgcagagt tctttaggcgccggctga

SEQ ID NO: 29

Atgacgttcttcgaacaggtgcgaaggttgcggagcgcagcgacaaccctgccgcgccgc

Gtggctatcgcggctatgggggctgtcctggtttacggtctggtcggtaccttcggcggg

Ccggccaccgcgggcgcattctctaggcccggtcttccagtggaatatctgcaggtgcca

-continued

Tccgcgtcgatgggccgcgacatcaaggtccagttccagggcggcggaccgcacgcggtc
Tacctgctcgacggtctgcgggcccaggatgactacaacggctgggacatcaacaccccg
Gccttcgaggagtactaccagtcagggttgtcggtgatcatgcccgtgggcggccaatcc
Agtttctacaccgactggtatcagccctcgcagagcaacggccagaactacacctacaag
Tgggagaccttccttaccagagagatgcccgcctggctacaggccaacaagggcgtgtcc
ccgacaggcaacgcggcggtgggtctttcgatgtcgggcggttccgcgctgatcctggcc
gcgtactacccgcagcagttcccgtacgccgcgtcgttgtcgggcttcctcaacccgtcc
gagggctggtggccgacgctgatcggcctggcgatgaacgactcgggcggttacaacgcc
aacagcatgtggggtccgtccagcgacccggcctggaagcgcaacgacccaatggttcag
attccccgcctggtcgccaacaacacccggatctgggtgtactgcggtaacggcacaccc
agcgacctcggcggcgacaacataccggcgaagttcctggaaggcctcaccctgcgcacc
aaccagaccttccgggacacctacgcggccgacggtggacgcaacggggtgtttaacttc
ccgcccaacggaacacactcgtggccctactggaacgagcagctggtcgccatgaaggcc
gatatccagcatgtgctcaacggcgcgacaccccggccgcccctgctgcgccggccgcc
tga

SEQ ID NO: 30 atgacagagcagcagtggaatttcgcgggtatcgaggccgcggcaagcgcaatccaggga
aatgtcacgtccattcattccctccttgacgaggggaagcagtccctgaccaagctcgca
gcggcctggggcggtagcggttcggaggcgtaccagggtgtccagcaaaaatgggacgcc
acggctaccgagctgaacaacgcgctgcagaacctggcgcggacgatcagcgaagccggt
caggcaatggcttcgaccgaaggcaacgtcactgggatgttcgcatag

SEQ ID NO: 31 atgtcgcaaatcatgtacaactaccccgcgatgttgggtcacgccggggatatggccgga
tatgccggcacgctgcagagcttgggtgccgagatcgccgtggagcaggccgcgttgcag
agtgcgtggcagggcgataccgggatcacgtatcaggcgtggcaggcacagtggaaccag
gccatggaagatttggtgcgggcctatcatgcgatgtccagcacccatgaagccaacacc
atggcgatgatggcccgcgacacggccgaagccgccaaatggggcggctag

SEQ ID NO: 32 atgagcaattcgcgccgccgctcactcaggtggtcatggttgctgagcgtgctggctgcc
gtcgggctgggcctggccacggcgccggcccaggcggccccgccggccttgtcgcaggac
cggttcgccgacttccccgcgctgcccctcgacccgtccgcgatggtcgcccaagtgggg
ccacaggtggtcaacatcaacaccaaactgggctacaacaacgccgtgggcgccgggacc
ggcatcgtcatcgatcccaacggtgtcgtgctgaccaacaaccacgtgatcgcgggcgcc
accgacatcaatgcgttcagcgtcggctccggccaaacctacggcgtcgatgtggtcggg
tatgaccgcacccaggatgtcgcggtgctgcagctgcgcggtgccggtggcctgccgtcg
gcggcgatcggtggcggcgtcgcggttggtgagcccgtcgtcgcgatgggcaacagcggt
gggcagggcggaacgccccgtgcggtgcctggcagggtggtcgcgctcggccaaaccgtg
caggcgtcggattcgctgaccggtgccgaagagacattgaacgggttgatccagttcgat
gccgcgatccagcccggtgattcgggcgggcccgtcgtcaacggcctaggacaggtggtc
ggtatgaacacggccgcgtccgataacttccagctgtcccagggtgggcagggattcgcc
attccgatcgggcaggcgatggcgatcgcgggccagatccgatcgggtggggggtcaccc
accgttcatatcgggcctaccgccttcctcggcttgggtgttgtcgacaacaacggcaac -continued ggcgcacgagtccaacgcgtggtcgggagcgctccggcggcaagtctcggcatctccacc
ggcgacgtgatcaccgcggtcgacggcgctccgatcaactcggccaccgcgatggcggac
gcgcttaacgggcatcatcccggtgacgtcatctcggtgacctggcaaaccaagtcgggc
ggcacgcgtacagggaacgtgacattggccgagggacccccggcctga

SEQ ID NO: 33 atggtggatttcggggcgttaccaccggagatcaactccgcgaggatgtacgccggcccg
ggttcggcctcgctggtggccgcggctcagatgtgggacagcgtggcgagtgacctgttt
tcggccgcgtcggcgtttcagtcggtggtctggggtctgacggtggggtcgtggataggt
tcgtcggcgggtctgatggtggcggcggcctcgccgtatgtggcgtggatgagcgtcacc
gcggggcaggccgagctgaccgccgcccaggtccgggttgctgcggcggcctacgagacg
gcgtatgggctgacggtgcccccgccggtgatcgccgagaaccgtgctgaactgatgatt
ctgatagcgaccaacctcttggggcaaaacaccccggcgatcgcggtcaacgaggccgaa
tacggcgagatgtgggcccaagacgccgccgcgatgtttggctacgccgcggcgacggcg
acggcgacggcgacgttgctgccgttcgaggaggcgccggagatgaccagcgcgggtggg
ctcctcgagcaggccgccgcggtcgaggaggcctccgacaccgccgcggcgaaccagttg
atgaacaatgtgccccaggcgctgcaacagctggcccagcccacgcagggcaccacgcct
tcttccaagctgggtggcctgtggaagacggtctcgccgcatcggtcgccgatcagcaac
atggtgtcgatggccaacaaccacatgtcgatgaccaactcgggtgtgtcgatgaccaac
accttgagctcgatgttgaagggctttgctccggcggcggccgcccaggccgtgcaaacc
gcggcgcaaaacggggtccgggcgatgagctcgctgggcagctcgctgggttcttcgggt
ctgggcggtggggtggccgccaacttgggtcgggcggcctcggtcggttcgttgtcggtg
ccgcaggcctgggccgcggccaaccaggcagtcaccccggcggcgcgggcgctgccgctg
accagcctgaccagcgccgcggaaagagggcccgggcagatgctgggcgggctgccggtg
gggcagatgggcgccagggccggtggtgggctcagtggtgtgctgcgtgttccgccgcga
ccctatgtgatgccgcattctccggcggccggctag

SEQ ID NO: 34 atgcggacccccagacgccactgccgtcgcatcgccgtcctcgccgccgttagcatcgcc
gccactgtcgttgccggctgctcgtcgggctcgaagccaagcggcggaccacttccggac
gcgaagccgctggtcgaggaggccaccgcgcagaccaaggctctcaagagcgcgcacatg
gtgctgacggtcaacggcaagatcccgggactgtctctgaagacgctgagcggcgatctc
accaccaaccccaccgccgcgacgggaaacgtcaagctcacgctgggtgggtctgatatc
gatgccgacttcgtggtgttcgacgggatcctgtacgccaccctgacgcccaaccagtgg
agcgatttcggtcccgccgccgacatctacgaccccgcccaggtctgaatcccggatacc
ggcctggccaacgtgctggcgaatttcgccgacgcaaaagccgaagggcgggataccatc
aacggccagaacaccatccgcatcagcgggaaggtatcggcacaggcggtgaaccagata
gcgccgccgttcaacgcgacgcagccggtgccggcgaccgtctggattcaggagaccggc
gatcatcaactggcacaggcccagttggaccgcggctcgggcaattccgtccagatgacc
ttgtcgaaatggggcgagaaggtccaggtcacgaagcccccggtgagctga

SEQ ID NO: 35 atggccaagacaattgcgtacgacgaagaggcccgtcgcggcctcgagcggggcttgaac
gccctcgccgatgcggtaaaggtgacattgggccccaagggccgcaacgtcgtcctggaa
aagaagtggggtgcccccacgatcaccaacgatggtgtgtccatcgccaaggagatcgag -continued

```
ctggaggatccgtacgagaagatcggcgccgagctggtcaaagaggtagccaagaagacc

gatgacgtcgccggtgacggcaccacgacggccaccgtgctggcccaggcgttggttcgc

gagggcctgcgcaacgtcgcggccggcgccaacccgctcggtctcaaacgcggcatcgaa

aaggccgtggagaaggtcaccgagaccctgctcaagggcgccaaggaggtcgagaccaag

gagcagattgcggccaccgcagcgatttcggcgggtgaccagtccatcggtgacctgatc

gccgaggcgatggacaaggtgggcaacgagggcgtcatcaccgtcgaggagtccaacacc

tttgggctgcagctcgagctcaccgagggtatgcggttcgacaagggctacatctcgggg

tacttcgtgaccgacccggagcgtcaggaggcggtcctggaggacccctacatcctgctg

gtcagctccaaggtgtccactgtcaaggatctgctgccgctgctcgagaaggtcatcgga

gccggtaagccgctgctgatcatcgccgaggacgtcgagggcgaggcgctgtccaccctg

gtcgtcaacaagatccgcggcaccttcaagtcggtggcggtcaaggctcccggcttcggc

gaccgccgcaaggcgatgctgcaggatatggccattctcaccggtggtcaggtgatcagc

gaagaggtcggcctgacgctggagaacgccgacctgtcgctgctaggcaaggcccgcaag

gtcgtggtcaccaaggacgagaccaccatcgtcgagggcgccggtgacaccgacgccatc

gccggacgagtggcccagatccgccaggagatcgagaacagcgactccgactacgaccgt

gagaagctgcaggagcggctggccaagctggccggtggtgtcgcggtgatcaaggccggt

gccgccaccgaggtcgaactcaaggagcgcaagcaccgcatcgaggatgcggttcgcaat

gccaaggccgccgtcgaggagggcatcgtcgccggtgggggtgtgacgctgttgcaagcg

gccccgaccctggacgagctgaagctcgaaggcgacgaggcgaccggcgccaacatcgtg

aaggtggcgctggaggccccgctgaagcagatcgccttcaactccgggctggagccgggc

gtggtggccgagaaggtgcgcaacctgccggctggccacggactgaacgctcagaccggt

gtctacgaggatctgctcgctgccggcgttgctgacccggtcaaggtgacccgttcggcg

ctgcagaatgcggcgtccatcgcggggctgttcctgaccaccgaggccgtcgttgccgac

aagccggaaaaggagaaggcttccgttcccggtggcggcgacatgggtggcatggatttc

tga
```

SEQ ID NO: 38

```
atggctgaaaactcgaacattgatgacatcaaggctccgttgcttgccgcgcttggagcg

gccgacctggccttggccactgtcaacgagttgatcacgaacctgcgtgagcgtgcggag

gagactcgtacggacacccgcagccgggtcgaggagagccgtgctcgcctgaccaagctg

caggaagatctgcccgagcagctcaccgagctgcgtgagaagttcaccgccgaggagctg

cgtaaggccgccgagggctacctcgaggccgcgactagccggtacaacgagctggtcgag

cgcggtgaggccgctctagagcggctgcgcagccagcagagcttcgaggaagtgtcggcg

cgcgccgaaggctacgtggaccaggcggtggagttgacccaggaggcgttgggtacggtc

gcatcgcagacccgcgcggtcggtgagcgtgccgccaagctggtcggcatcgagctgcct

aagaaggctgctccggccaagaaggccgctccggccaagaaggccgctccggccaagaag

gcggcggccaagaaggcgcccgcgaagaaggcggcggccaagaaggtcacccagaagtag
```

SEQ ID NO: 37

```
gtgacgcaaaccggcaagcgtcagagacgcaaattcggtcgcatccgacagttcaactcc

ggccgctggcaagccagctacaccggccccgacggccgcgtgtacatcgcccccaaaacc

ttcaacgccaagatcgacgccgaagcatggctcaccgaccgccgccgcgaaatcgaccga

caactatggtccccggcatcgggtcaggaagaccgccccggagccccattcggtgagtac
```

-continued gccgaaggatggctgaagcagcgtggaatcaaggaccgcacccgcgcccactatcgcaaa ctgctggacaaccacatcctggccaccttcgctgacaccgacctacgcgacatcaccccg gccgccgtgcgccgctggtacgccaccaccgccgtgggcacaccgaccatgcgggcacac tcctacagcttgctgcgcgcaatcatgcagaccgccttggccgacgacctgatcgactcc aacccctgccgcatctcaggcgcgtccaccgcccgccgcgtccacaagatcaggcccgcc accctcgacgagctggaaaccatcaccaaagccatgcccgacccctaccaggcgttcgtg ctgatggcggcatggctggccatgcgctacggcgagctgaccgaattacgccgcaaagac atcgacctgcacggcgaggttgcgcgggtgcggcgggctgtcgttcgggtgggcgaaggc ttcaaggtgacgacaccgaaaagcgatgcgggagtgcgcgacataagtatcccgccacat ctgatacccgccatcgaagaccaccttcacaaacacgtcaaccccggccgggagtccctg ctgttcccatcggtcaacgaccccaaccgtcacctagcaccctcggcgctgtaccgcatg ttctacaaggcccgaaaagccgccggccgaccagacttacgggtgcacgaccttcgacac tccggcgccgtgttggctgcatccaccggcgccacactggccgaactgatgcagcggcta ggacacagcacagccggcgccgcactccgctaccagcacgccgccaagggccgggaccgc gaaatcgccgcactgttaagcaaactggccgagaaccaggagatgtga

SEQ ID NO: 38 gtgatagcgggcgtcgaccaggcgcttgcagcaacaggccaggctagccagcgggcggca ggcgcatctggtggggtcaccgtcggtgtcggcgtgggcacggaacagaggaacctttcg gtggttgcaccgagtcagttcacatttagttcacgcagcccagattttgtggatgaaacc gcaggtcaatcgtggtgcgcgatactgggattgaaccagtttcactag

SEQ ID NO: 39 atggccaccacccttcccgttcagcgccacccgcggtccctcttccccgagttttctgag ctgttcgcggccttcccgtcattcgccggactccggcccaccttcgacacccggttgatg cggctggaagacgagatgaaagaggggcgctacgaggtacgcgcggagcttcccggggtc gaccccgacaaggacgtcgacattatggtccgcgatggtcagctgaccatcaaggccgag cgcaccgagcagaaggacttcgacggtcgctcggaattcgcgtacggttccttcgttcgc acggtgtcgctgccggtaggtgctgacgaggacgacattaaggccacctacgacaagggc attcttactgtgtcggtggcggtttcggaagggaagccaaccgaaaagcacattcagatc cggtccaccaactga

SEQ ID NO: 40 atgagtggacgccaccgtaagcccaccacatccaacgtcagcgtcgccaagatcgccttt accggcgcagtactcggtggcggcggcatcgccatggccgctcaggcgaccgcggccacc gacggggaatgggatcaggtggcccgctgcgagtcgggcggcaactggtcgatcaacacc ggcaacggttacctcggtggcttgcagttcactcaaagcacctgggccgcacatggtggc ggcgagttcgccccgtcggctcagctggccagccgggagcagcagattgccgtcggtgag cgggtgctggccacccagggtcgcggcgcctggccggtgtgcggccgcgggttatcgaac gcaacaccccgcgaagtgcttcccgcttcggcagcgatggacgctccgttggacgcggcc gcggtcaacggcgaaccagcaccgctggccccgccgcccgccgacccggcgccacccgtg gaacttgccgctaacgacctgcccgcaccgctgggtgaacccctcccggcagctcccgcc gacccggcaccacccgccgacctggcaccacccgcgcccgccgacgtcgcgccacccgtg gaacttgccgtaaacgacctgcccgcaccgctgggtgaacccctcccggcagctcccgcc gacccggcaccacccgccgacctggcaccacccgcgcccgccgacctggcgccacccgcg -continued

```
cccgccgacctggcgccacccgcgcccgccgacctggcaccacccgtggaacttgccgta
aacgacctgcccgcgccgctgggtgaacccctcccggcagctcccgccgaactggcgcca
cccgccgatctggcacccgcgtccgccgacctggcgccacccgcgcccgccgacctggcg
ccacccgcgcccgccgaactggcgccacccgcgcccgccgacctggcaccacccgctgcg
gtgaacgagcaaaccgcgccgggcgatcagcccgccacagctccaggcggcccggttggc
cttgccaccgatttggaactccccgagcccgacccccaaccagctgacgcaccgccgccc
ggcgacgtcaccgaggcgcccgccgaaacgccccaagtctcgaacatcgcctatacgaag
aagctgtggcaggcgattcgggcccaggacgtctgcggcaacgatgcgctggactcgctc
gcacagccgtacgtcatcggctga
```

SEQ ID NO: 41

```
atgttgcgcctggtagtcggtgcgctgctgctggtgttggcgttcgccggtggctatgcg
gtcgccgcatgcaaaacggtgacgttgaccgtcgacggaaccgcgatgcgggtgaccacg
atgaaatcgcgggtgatcgacatcgtcgaagagaacgggttctcagtcgacgaccgcgac
gacctgtatcccgcggccggcgtgcaggtccatgacgccgacaccatcgtgctgcggcgt
agccgtccgctgcagatctcgctggatggtcacgacgctaagcaggtgtggacgaccgcg
tcgacggtggacgaggcgctggcccaactcgcgatgaccgacacggcgccggccgcggct
tctcgcgccagccgcgtcccgctgtccgggatggcgctaccggtcgtcagcgccaagacg
gtgcagctcaacgacggcgggttggtgcgcacggtgcacttgccggcccccaatgtcgcg
gggctgctgagtgcggccggcgtgccgctgttgcaaagcgaccacgtggtgcccgccgcg
acggccccgatcgtcgaaggcatgcagatccaggtgacccgcaatcggatcaagaaggtc
accgagcggctgccgctgccgccgaacgcgcgtcgtgtcgaggacccggagatgaacatg
agccgggaggtcgtcgaagacccgggggttccggggacccaggatgtgacgttcgcggta
gctgaggtcaacggcgtcgagaccggccgtttgcccgtcgccaacgtcgtggtgaccccg
gcccacgaagccgtggtgcgggtgggcaccaagcccggtaccgaggtgcccccggtgatc
gacggaagcatctgggacgcgatcgccggctgtgaggccggtggcaactgggcgatcaac
accggcaacgggtattacggtggtgtgcagtttgaccagggcacctgggaggccaacggc
gggctgcggtatgcaccccgcgctgacctcgccacccgcgaagagcagatcgccgttgcc
gaggtgacccgactgcgtcaaggttggggcgcctggccggtatgtgctgcacgagcgggt
gcgcgctga
```

SEQ ID NO: 42

```
gtgcatcctttgccggccgaccacggccggtcgcggtgcaatagacacccgatctcacca
ctctctctaatcggtaacgcttcggccacttccggcgatatgtcgagcatgacaagaatc
gccaagccgctcatcaagtccgccatggccgcaggactcgtcacggcatccatgtcgctc
tccaccgccgttgcccacgccggtcccagcccgaactgggacgccgtcgcgcagtgcgaa
tccgggggcaactgggcggccaacaccggaaacggcaaatacggcggactgcagttcaag
ccggccacctgggccgcattcggcggtgtcggcaacccagcagctgcctctcgggaacaa
caaatcgcagttgccaatcgggttctcgccgaacagggattggacgcgtggccgacgtgc
ggcgccgcctctggccttccgatcgcactgtggtcgaaacccgcgcagggcatcaagcaa
atcatcaacgagatcatttgggcaggcattcaggcaagtattccgcgctga
```

SEQ ID NO: 43

```
atgacaccgggtttgcttactactgcgggtgctggccgaccacgtgacaggtgcgccagg
atcgtatgcacggtgttcatcgaaaccgccgttgtcgcgaccatgtttgtcgcgttgttg
```

-continued ggtctgtccaccatcagctcgaaagccgacgacatcgattgggacgccatcgcgcaatgc
gaatccggcggcaattgggcggccaacaccggtaacgggttatacggtggtctgcagatc
agccaggcgacgtgggattccaacggtggtgtcgggtcgccggcggccgcgagtccccag
caacagatcgaggtcgcagacaacattatgaaaacccaaggcccgggtgcgtggccgaaa
tgtagttcttgtagtcagggagacgcaccgctgggctcgctcacccacatcctgacgttc
ctcgcggccgagactggaggttgttcggggagcagggacgattga

SEQ ID NO: 44 ttgaagaacgcccgtacgacgctcatcgccgccgcgattgccgggacgttggtgaccacg
tcaccagccggtatcgccaatgccgacgacgcgggcttggacccaaacgccgcagccggc
ccggatgccgtgggctttgacccgaacctgccgccggccccggacgctgcacccgtcgat
actccgccggctccggaggacgcgggctttgatcccaacctcccccgccgctggccccg
gacttcctgtccccgcctgcggaggaagcgcctcccgtgcccgtggcctacagcgtgaac
tgggacgcgatcgcgcagtgcgagtccggtggaaactggtcgatcaacaccggtaacggt
tactacggcggcctgcggttcaccgccggcacctggcgtgccaacggtggctcggggtcc
gcggccaacgcgagccgggaggagcagatccgggtggctgagaacgtgctgcgttcgcag
ggtatccgcgcctggccggtctgcggccgccgcggctga

SEQ ID NO: 45 atgatcgccacaacccgcgatcgtgaaggagccaccatgatcacgtttaggctgcgcttg
ccgtgccggacgatactgcgggtgttcagccgcaatccgctggtgcgtgggacggatcga
ctcgaggcggtcgtcatgctgctggccgtcacggtctcgctgctgactatcccgttcgcc
gccgcggccggcaccgcagtccaggattcccgcagccacgtctatgcccaccaggcccag
acccgccatcccgcaaccgcgaccgtgatcgatcacgaggggggtgatcgacagcaacacg
accgccacgtcagcgccgccgcgcacgaagatcaccgtgcctgcccgatgggtcgtgaac
ggaatagaacgcagcggtgaggtcaacgcgaagccgggaaccaaatccggtgaccgcgtc
ggcatttgggtcgacagtgccggtcagctggtcgatgaaccagctccgccggcccgtgcc
attgcggatgcggccctggccgccttgggactctggttgagcgtcgccgcggttgcgggc
gccctgctggcgctcactcgggcgattctgatccgcgttcgcaacgccagttggcaacac
gacatcgacagcctgttctgcacgcagcggtga

SEQ ID NO: 46 atgacggagccagcggcgtgggacgaaggcaagccgcgaatcatcactttgaccatgaac
cccgccttggacatcacgacgagcgtcgacgtggtgcgcccgaccgagaaaatgcgttgt
ggcgcacctcgctacgatcccggcggcggcggtatcaatgtcgcccgcattgtgcatgtc
ctcggcggttgctcgacagcactgttcccggccggcgggtcgaccgggagcctgctgatg
gcgctgctcggtgatgcgggagtgccatttcgcgtcattccgatcgcggcctcgacgcgg
gagagcttcacggtcaacgagtccaggaccgccaagcagtatcgtttcgtgcttccgggg
ccgtcgctgaccgtcgcggagcaggagcaatgcctcgacgaactgcgcggtgcggcggct
tcggccgcctttgtggtggccagtggcagcctgccgccaggtgtggctgccgactactat
cagcgggttgccgacatctgccgccgatcgagcactccgctgatcctggatacatctggt
ggcgggttgcagcacatttcgtccggggtgtttcttctcaaggcgagcgtgcgggaactg
cgcgagtgcgtcggatccgaactgctgaccgagcccgaacaactggccgccgcacacgaa
ctcattgaccgtgggcgcgccgaggtcgtggtggtctcgcttggatctcagggcgcgcta
ttggccacacgacatgcgagccatcgattttcgtcgattccgatgaccgcggttagcggt -continued gtcggcgccggcgacgcgatggtggccgcgattaccgtgggcctcagccgtggctggtcg ctcatcaagtccgttcgcttgggaaacgcggcaggtgcagccatgctgctgacgccaggc accgcggcctgcaatcgcgacgatgtggagaggttcttcgagctggcggccgaacccacc gaagtcgggcaggatcaatacgtttggcacccgatcgttaacccggaagcctcgccatga

SEQ ID NO: 47 atgccggacaccatggtgaccaccgatgtcatcaagagcgcggtgcagttggcctgccgc gcaccgtcgctccacaacagccagccctggcgctggatagccgaggaccacacggttgcg ctgttcctcgacaaggatcgggtgctttacgcgaccgaccactccggccgggaagcgctg ctggggtgcggcgccgtactcgaccactttcgggtggcgatggcggccgcgggtaccacc gccaatgtggaacggtttcccaaccccaacgatcctttgcatctggcgtcaattgacttc agcccggccgatttcgtcaccgagggccaccgtctaagggaggatgcgatcctactgcgc cgtaccgaccggctgcctttcgccgagccgccggattgggacttggtggagtcgcagttg cgcacgaccgtcaccgccgacacggtgcgcatcgacgtcatcgccgacgatatgcgtccc gaactggcggcggcgtccaaactcaccgaatcgctgcggctctacgattcgtcgtatcat gccgaactcttttggtggacaggggcttttgagacttctgagggcataccgcacagttca ttggtatcggcggccgaaagtgaccgggtcaccttcggacgcgacttcccggtcgtcgcc aacaccgataggcgcccggagtttggccacgaccgctctaaggtcctggtgctctccacc tacgacaacgaacgcgccagcctactgcgctgcggcgagatgctttccgccgtattgctt gacgccaccatggctgggcttgccacctgcacgctgacccacatcaccgaactgcacgcc agccgagacctggtcgcagcgctgattgggcagcccgcaactccgcaagccttggttcgc gtcggtctggccccggagatggaagagccgccaccggcaacgcctcggcgaccaatcgat gaagtgtttcacgttcgggctaaggatcaccggtag

SEQ ID NO: 48 atgaccaccgcacgcgacatcatgaacgcaggtgtgacctgtgttggcgaacacgagacg ctaaccgctgccgctcaatacatgcgtgagcacgacatcggcgcgttgccgatctgcggg gacgacgaccggctgcacggcatgctcaccgaccgcgacattgtgatcaaaggcctggct gcgggcctagacccgaataccgccacggctggcgagttggcccgggacagcatctactac gtcgatgcgaacgcaagcatccaggagatgctcaacgtcatggaagaacatcaggtccgc cgtgttccggtcatctcagagcaccgcttggtcggaatcgtcaccgaagccgacatcgcc cgacacctgcccgagcacgccattgtgcagttcgtcaaggcaatctgctcgcccatggcc ctcgccagctag

SEQ ID NO: 49 atggcaagttctgcgagcgacggcacccacgaacgctcggcttttcgcctgagtccaccg gtcttgagcggcgccatgggaccgttcatgcacaccggtctgtacgtcgctcaatcgtgg cgcgactatctgggtcaacagcccgataaactgccgatcgcacggcccactattgcctta gcggcgcaagcctttcgagacgaaatcgtcctgctgggcctcaaggcacgacgtccggtc agcaatcatcgagtgttcgagcgcatcagccaagaagtggccgctggactggagttctat gggaatcgcagatggctggagaagcctagcggatttttttgcccagcccccaccgctcacc gaggtcgcggtccgaaaggtcaaggaccgcagacgctcccttttatcgcatcttcttcgac agtgggtttacgccgcatccgggtgaaccgggcagccaacggtggctctcatacactgcg aacaatcgcgagtacgccctgttactgcggcacccagagccgcgtccctggctggtttgt gtacacggcaccgagatgggcagggccccgttggatctcgcggtgttccgcgcctggaag -continued ctgcatgacgaactcggcctgaacattgtcatgccggttcttccgatgcatggtccccgc gggcaaggtctgccgaagggcgccgtttttcccggagaagatgttctcgacgatgtgcat gggacggctcaagcggtgtgggatatccggcggctgttgtcctggatacgatcgcaggag gaggagtcgctgatcgggttgaacggtctctcgctgggcggctacatcgcgtcattggtc gccagcctcgaagaaggtctcgcctgcgcgattctcggtgtcccagtggctgatctgatc gagttgttgggccgccactgcggtcttcggcacaaagacccccgccgccacaccgtcaag atggccgaaccgatcggccgaatgatctcgccgctctcacttacgccactggtgcccatg ccgggccgctttatctacgcgggcattgccgaccgactcgtgcatccacgcgaacaggtg actcgcctctgggagcactggggcaaacccgaaatcgtgtggtatccaggcggtcacact ggcttcttccagtcgcggccggtacgacggtttgtccaggctgcgctggagcagtcgggc ctgttggacgcgccacggacacagcgcgaccgttccgcctaa

SEQ ID NO: 50 atgtccacgcaacgaccgaggcactccggtattcgggctgttggcccctacgcatgggcc ggccgatgtggtcggataggcaggtggggggtgcaccaggaggcgatgatgaatctagcg atatggcacccgcgcaaggtgcaatccgccaccatctatcaggtgaccgatcgctcgcac gacgggcgcacagcacgggtgcctggtgacgagatcactagcaccgtgtccggttggttg tcggagttgggcacccaaagcccgttggccgatgagcttgcgcgtgcggtgcggatcggc gactggcccgctgcgtacgcaatcggtgagcacctgtccgttgagattgccgttgcggtc taa

SEQ ID NO: 51

ATGGACGCCATGAAGAGGGGCCTGTGCTGCGTGCTGCTGCTGTGTGGCGCCGTGTTCGTGTCCCCCAGCCAGGAA

ATCCACGCCCGGTTCAGACGGGGCAGCATGCAGCTGGTGGACAGAGTCAGAGGCGCCGTGACCGGCATGAGCAGA

CGGCTGGTCGTGGGAGCTGTCGGAGCCGCTCTGGTGTCTGGACTCGTGGGAGCCGTGGGCGGAACAGCTACAGCC

GGCGCTTTCAGCAGACCCGGCCTGCCCGTGGAATATCTGCAGGTCCCCAGCCCCAGCATGGGCCGGGACATCAAG

GTGCAGTTCCAGTCTGGCGGAGCCAACAGCCCTGCTCTGTACCTGCTGGACGGCCTGAGAGCCCAGGACGACTTC

AGCGGCTGGGACATCAACACCCCCGCCTTCGAGTGGTACGACCAGAGCGGCCTGTCTGTGGTCATGCCTGTGGGC

GGCCAGAGCAGCTTCTACAGCGACTGGTATCAGCCCGCTTGTGGCAAGGCCGGCTGCCAGACCTACAAGTGGGAG

ACATTCCTGACCAGCGAGCTGCCCGGCTGGCTGCAGGCCAACAGACACGTGAAGCCCACCGGCTCTGCCGTCGTG

GGCCTGTCTATGGCTGCCAGCTCTGCCCTGACCCTGGCCATCTACCACCCCCAGCAGTTCGTGTACGCTGGCGCC

ATGTCTGGCCTGCTGGATCCTTCTCAGGCCATGGGACCCACCCTGATCGGACTGGCTATGGGAGATGCCGGCGGA

TACAAGGCCAGCGACATGTGGGGCCCTAAAGAGGACCCCGCCTGGCAGAGAAACGACCCCCTGCTGAACGTGGGC

AAGCTGATCGCCAACAACACCAGAGTGTGGGTGTACTGCGGCAACGGCAAGCTGAGCGACCTGGGCGGCAACAAC

CTGCCCGCCAAGTTCCTGGAAGGCTTCGTGCGGACCAGCAACATCAAGTTCCAGGACGCCTACAACGCTGGCGGC

GGACACAACGGCGTGTTCGACTTCCCCGACAGCGGCACCCACAGCTGGGAGTATTGGGGAGCCCAGCTGAATGCC

ATGAAGCCCGACCTGCAGAGAGCCCTGGGCGCCACCCCTAATACTGGACCTGCTCCTCAGGGCGCATGA

SEQ ID NO: 52

MDAMKRGLCCVLLLCGAVFVSPSQEIHARFRRGSMQLVDRVRGAVTGMSRRLVVGAVGAA

LVSGLVGAVGGTATAGAFSRPGLPVEYLQVPSPSMGRDIKVQFQSGGANSPALYLLDGLR

AQDDFSGWDINTPAFEWYDQSGLSVVMPVGGQSSFYSDWYQPACGKAGCQTYKWETFLTS

ELPGWLQANRHVKPTGSAVVGLSMAASSALTLAIYHPQQFVYAGAMSGLLDPSQAMGPTL

-continued

IGLAMGDAGGYKASDMWGPKEDPAWQRNDPLLNVGKLIANNTRVWVYCGNGKLSDLGGNN

LPAKFLEGFVRTSNIKFQDAYNAGGGHNGVFDFPDSGTHSWEYWGAQLNAMKPDLQRALG

ATPNTGPAPQGA

SEQ ID NO: 53 aagaagcagggcgacgccgacgtgtgtggcgaggtggcctacatccagagcgtggtgtccgac tgccacgtgccaaccgccgagctgcggaccctgctggaaatccggaagctgttcctggaaatc cagaaactgaaggtggaactgcagggcctgagcaaagagtga

SEQ ID NO: 54

ATGGACGCCATGAAGAGGGGCCTGTGCTGCGTGCTGCTGCTGTGTGGCGCCGTGTTCGTGTCCCCCAGCCAGGAA

ATCCACGCCCGGTTCAGACGGGGCAGCATGCAGCTGGTGGACAGAGTCAGAGGCGCCGTGACCGGCATGAGCAGA

CGGCTGGTCGTGGGAGCTGTCGGAGCCGCTCTGGTGTCTGGACTCGTGGGAGCCGTGGGCGGAACAGCTACAGCC

GGCGCTTTCAGCAGACCCGGCCTGCCCGTGGAATATCTGCAGGTCCCCAGCCCCAGCATGGGCCGGGACATCAAG

GTGCAGTTCCAGTCTGGCGGAGCCAACAGCCCTGCTCTGTACCTGCTGGACGGCCTGAGAGCCCAGGACGACTTC

AGCGGCTGGGACATCAACACCCCCGCCTTCGAGTGGTACGACCAGAGCGGCCTGTCTGTGGTCATGCCTGTGGGC

GGCCAGAGCAGCTTCTACAGCGACTGGTATCAGCCCGCTTGTGGCAAGGCCGGCTGCCAGACCTACAAGTGGGAG

ACATTCCTGACCAGCGAGCTGCCCGGCTGGCTGCAGGCCAACAGACACGTGAAGCCCACCGGCTCTGCCGTCGTG

GGCCTGTCTATGGCTGCCAGCTCTGCCCTGACCCTGGCCATCTACCACCCCCAGCAGTTCGTGTACGCTGGCGCC

ATGTCTGGCCTGCTGGATCCTTCTCAGGCCATGGGACCCACCCTGATCGGACTGGCTATGGGAGATGCCGGCGGA

TACAAGGCCAGCGACATGTGGGGCCCTAAAGAGGACCCCGCCTGGCAGAGAAACGACCCCCTGCTGAACGTGGGC

AAGCTGATCGCCAACAACACCAGAGTGTGGGTGTACTGCGGCAACGGCAAGCTGAGCGACCTGGGCGGCAACAAC

CTGCCCGCCAAGTTCCTGGAAGGCTTCGTGCGGACCAGCAACATCAAGTTCCAGGACGCCTACAACGCTGGCGGC

GGACACAACGGCGTGTTCGACTTCCCCGACAGCGGCACCCACAGCTGGGAGTATTGGGGAGCCCAGCTGAATGCC

ATGAAGCCCGACCTGCAGAGAGGCAGCAAGAAGCAGGGCGACGCCGACGTGTGTGGCGAGGTGGCCTACATCCAG

AGCGTGGTGTCCGACTGCCACGTGCCAACCGCCGAGCTGCGGACCCTGCTGGAAATCCGGAAGCTGTTCCTGGAA

ATCCAGAAACTGAAGGTGGAACTGCAGGGCCTGAGCAAAGAGTGA

SEQ ID NO: 55

MDAMKRGLCCVLLLCGAVFVSPSQEIHARFRRGSMQLVDRVRGAVTGMSRRLVVGAVGAA

LVSGLVGAVGGTATAGAFSRPGLPVEYLQVPSPSMGRDIKVQFQSGGANSPALYLLDGLR

AQDDFSGWDINTPAFEWYDQSGLSVVMPVGGQSSFYSDWYQPACGKAGCQTYKWETFLTS

ELPGWLQANRHVKPTGSAVVGLSMAASSALTLAIYHPQQFVYAGAMSGLLDPSQAMGPTL

IGLAMGDAGGYKASDMWGPKEDPAWQRNDPLLNVGKLIANNTRVWVYCGNGKLSDLGGNN

LPAKFLEGFVRTSNIKFQDAYNAGGGHNGVFDFPDSGTHSWEYWGAQLNAMKPDLQRGSK

KQGDADVCGEVAYIQSVVSDCHVPTAELRTLLEIRKLFLEIQKLKVELQGLSKE

SEQ ID NO: 56

ATGCAGCTGGTGGACAGAGTCAGAGGCGCCGTGACCGGCATGAGCAGACGGCTGGTCGTGGGAGCTGTCGGAGCC

GCTCTGGTGTCTGGACTCGTGGGAGCCGTGGGCGGAACAGCTACAGCCGGCGCTTTCAGCAGACCCGGCCTGCCC

GTGGAATATCTGCAGGTCCCCAGCCCCAGCATGGGCCGGGACATCAAGGTGCAGTTCCAGTCTGGCGGAGCCAAC

AGCCCTGCTCTGTACCTGCTGGACGGCCTGAGAGCCCAGGACGACTTCAGCGGCTGGGACATCAACACCCCCGCC

TTCGAGTGGTACGACCAGAGCGGCCTGTCTGTGGTCATGCCTGTGGGCGGCCAGAGCAGCTTCTACAGCGACTGG

TATCAGCCCGCTTGTGGCAAGGCCGGCTGCCAGACCTACAAGTGGGAGACATTCCTGACCAGCGAGCTGCCCGGC

TGGCTGCAGGCCAACAGACACGTGAAGCCCACCGGCTCTGCCGTCGTGGGCCTGTCTATGGCTGCCAGCTCTGCC

CTGACCCTGGCCATCTACCACCCCCAGCAGTTCGTGTACGCTGGCGCCATGTCTGGCCTGCTGGATCCTTCTCAG

GCCATGGGACCCACCCTGATCGGACTGGCTATGGGAGATGCCGGCGGATACAAGGCCAGCGACATGTGGGGCCCT

-continued

```
AAAGAGGACCCCGCCTGGCAGAGAAACGACCCCCTGCTGAACGTGGGCAAGCTGATCGCCAACAACACCAGAGTG

TGGGTGTACTGCGGCAACGGCAAGCTGAGCGACCTGGGCGGCAACAACCTGCCCGCCAAGTTCCTGGAAGGCTTC

GTGCGGACCAGCAACATCAAGTTCCAGGACGCCTACAACGCTGGCGGCGGACACAACGGCGTGTTCGACTTCCCC

GACAGCGGCACCCACAGCTGGGAGTATTGGGGAGCCCAGCTGAATGCCATGAAGCCCGACCTGCAGAGAGCCCTG

GGCGCCACCCCTAATACTGGACCTGCTCCTCAGGGCGCATGA
```

SEQ ID NO:57 gaagcccgacctgcaacgtggatccaa-gaagcaaggtgatgctgatg

SEQ ID NO:58 agggccctctagatgcatgctcgag eggccgcttattact ecttgctcagt ecttgc

SEQ ID NO:59 GGGGCATATGTTTTCCCGGC-CGGGCTTGCCGGTGG

SEQ ID NO:60 GGGGGGATCCGGCGC-CCTGGGGCGCGGCCCGGTGTT

LIST OF FIGURES

FIG. 1: Screening of DNA in Balb/c Mice

Balb/c mice were immunised intramuscularly (im) at weeks 0 and 2 with 50 μg of either DNA-85A or DNA-85AIMX313. IFN-γ ELISpot was used to measure the response to p15 and p11 together in the blood 12 days after each vaccination (panel a.) of each individual peptide in the spleen 14 days after the final vaccination.

Figure 2:
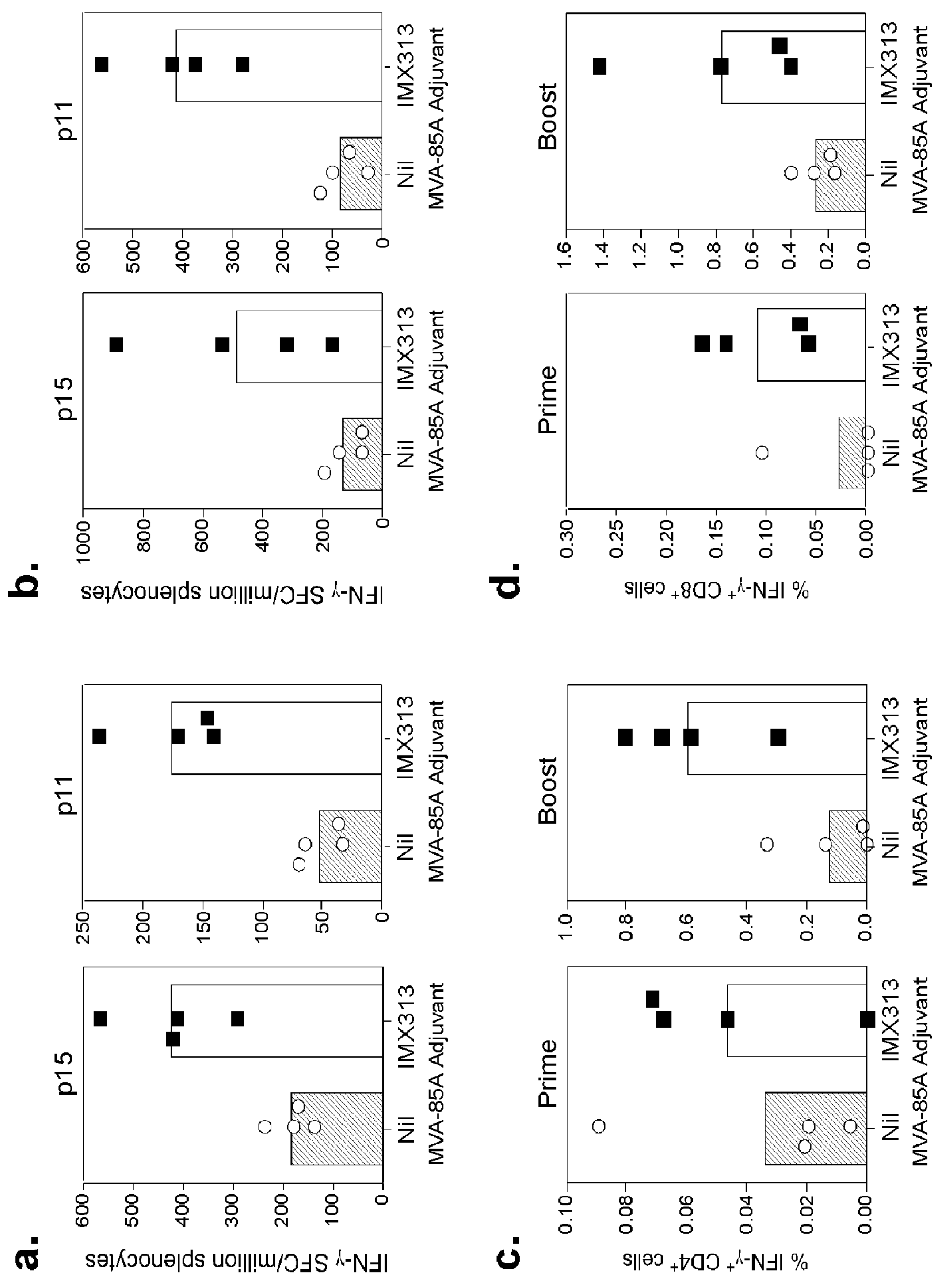

FIG. 2: Screening of MVA in Balb/c Mice

Balb/c mice were immunised with 106 PFU of MVA-85A or MVA-85AIMX313 via the intramuscular (panel a.) or intradermal (id) (panel b.) route at day 0 and the response to p15 and p11 measured in the spleen of all animals 1 week later.

Balb/c mice were immunised im with 106 PFU or MVA-85A or MVA-85AIMX313 at weeks 0 and 2. Intracellular cytokine staining was performed on blood samples taken 1 week after the prime or boost vaccination. Graphs represent the frequency of IFN-γ producing CD4+ (panel c.) or CD8+ (panel d.) cells.

For all graphs, the bar represents the mean per group with each individual animal displayed as a single point.

Figure 3:
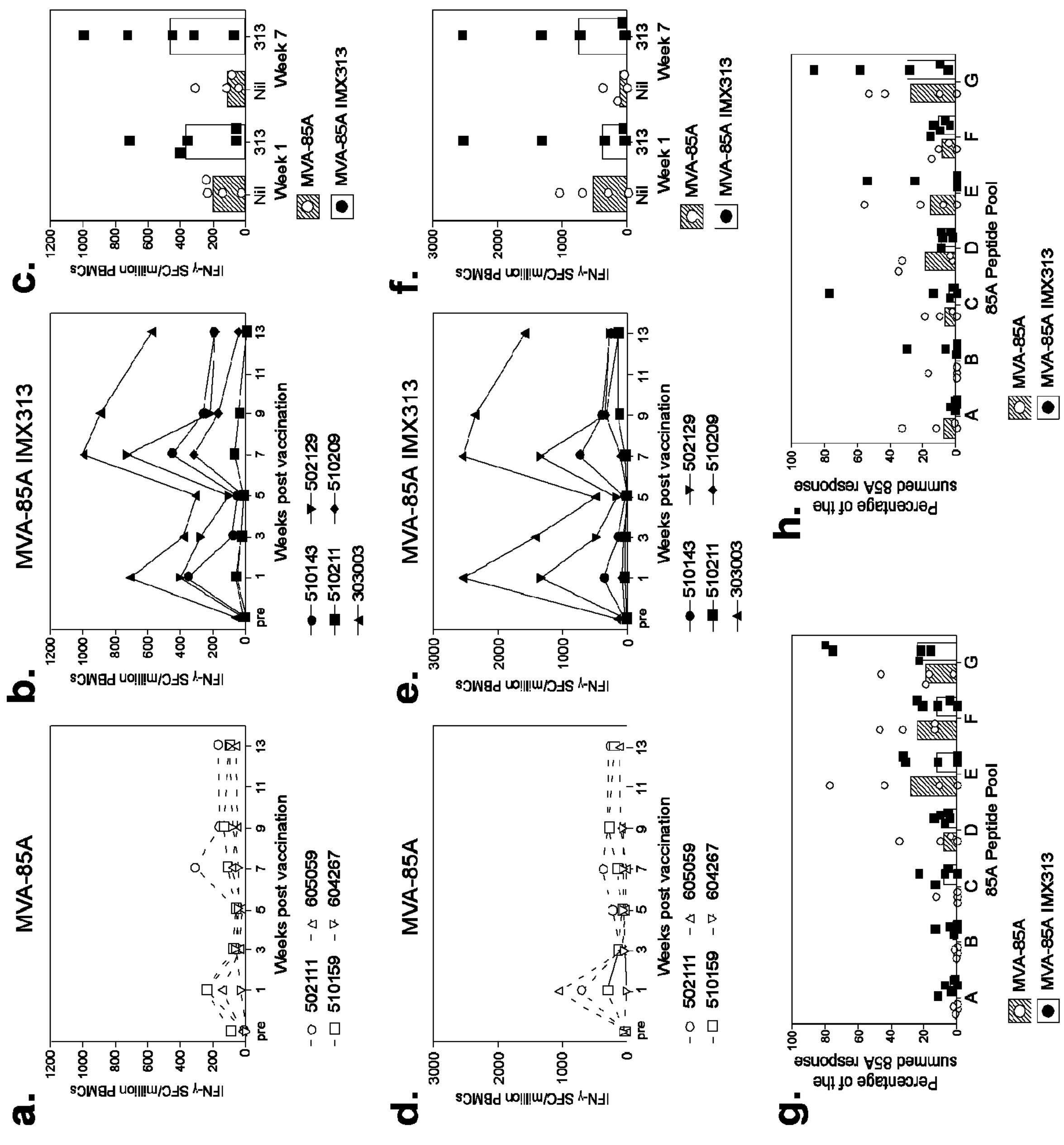

FIG. 3: IFN-γ ELISpot Responses to Antigen 85A

Male rhesus macaques were immunised at weeks 0 and 6 with either 106 PFU MVA-85A or MVA-85AIMX313 and the response to antigen 85A measured in the blood by IFN-γ ELISpot before vaccination (pre) and fortnightly from week 1 onwards. Graphs represent the response of each individual animal to a single pool containing all 85A peptides (panels a. & b.) or the sum of 7 separate peptide pools (panels d. & e.) for animals immunised with MVA-85A (panels a. & d.) or MVA-85AIMX313 (panels b. & e.).

Panels c. & f: Graphs represent the grouped response to 85A (panel c.) or the sum of all pools (panel f.) at week 1 or week 7 post vaccination Bars represent the median group response with each animal displayed as a single point.

Panels g. & h.: The graph displays the response to each peptide pool as a percentage of the summed pool response at week 1 (panel g.) or week 7 (panel h.). Bars represent the median response per group with each animal displayed as a single point.

Figure 4:
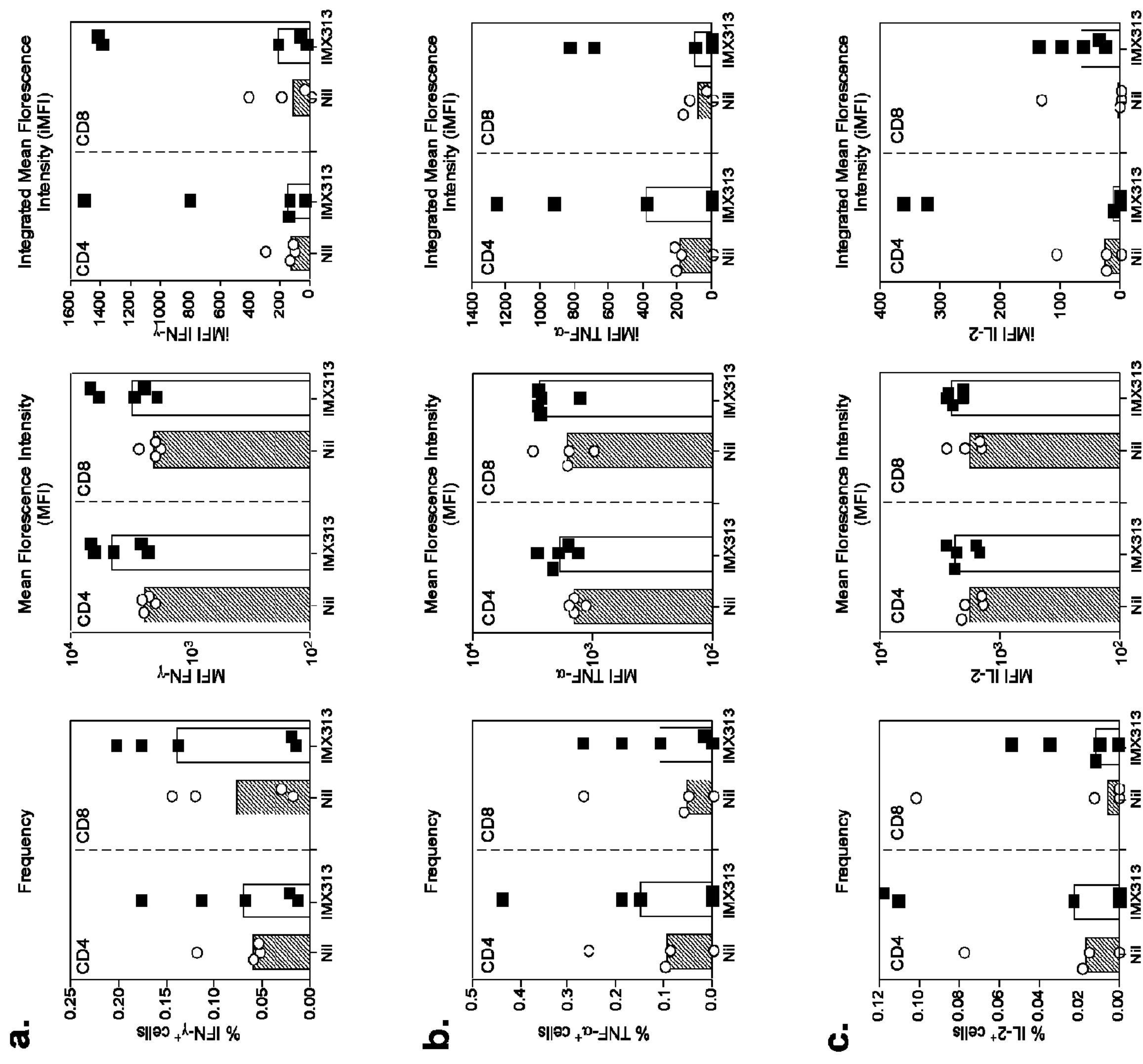

FIG. 4: Cytokine Secretion 1 Week after Boosting Vaccine

Week 7 frozen PBMCs samples were thawed rested overnight prior to restimulation for 6 hours in the presence of anti-CD28, anti-CD49d and 2μg/m1 of antigen 85A peptides with the addition of golgi-plug and golgi-stop for the final 4 hours of stimulation. Samples were surfaced stained for CD4, CD8, CD3, CD45RA, CD95, CD14 and CD20 prior to fixation and intracellular staining for IFN-γ(panel (a.)), TNF-α (panel (b.)) and IL-2 (panel (c.)). Samples were gated on size, CD14- and CD20-, CD3+prior to separation into CD4+and CD8+cells and analysis of the frequency and mean fluorescence intensity of each cytokine The frequency of antigen specific cytokine production was determined after subtraction of the frequency of cytokine positive cells in the unstimulated control. The integrated mean fluorescence intensity was calculated by multiplying the frequency by MFI and then subtracting the iMFI from the corresponding unstimulated control.

Figure 5:
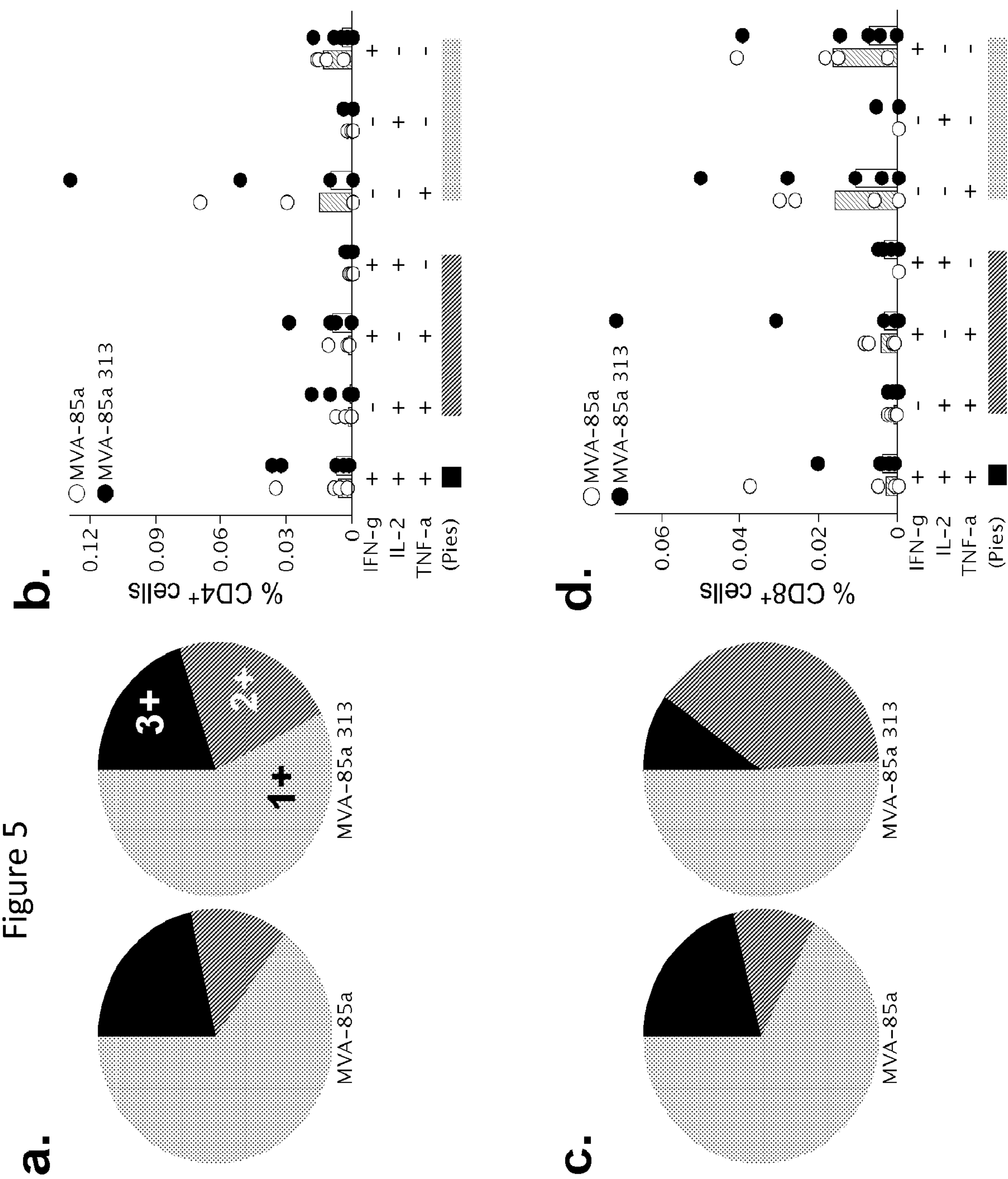

FIG. 5: Polyfunctionality of the Cytokine Response 1 Week after Boosting Vaccination.

In the same samples as described in FIG. 4, responses to each of the 3 cytokines were simultaneously analysed to determine the frequency and proportion of cells making either 1 single cytokine, a combination of 2 cytokines or all 3 cytokines.

Panels a. & c.: Pie charts represent the proportion of CD4+ (panel a.) or CD8+ (panel c.) cytokine producing cells which produce all 3 cytokines (black), a combination of 2 cytokine (darker grey) or only 1 cytokine (light grey).

Panels b.& d.: Graphs represent the frequency of each population of cytokine producing cells relative to the overall population of CD4+ (panel b.) or CD8+ (panel d.) cells. Bars represent the median per group with each animal displayed as a single point.

Figure 6:
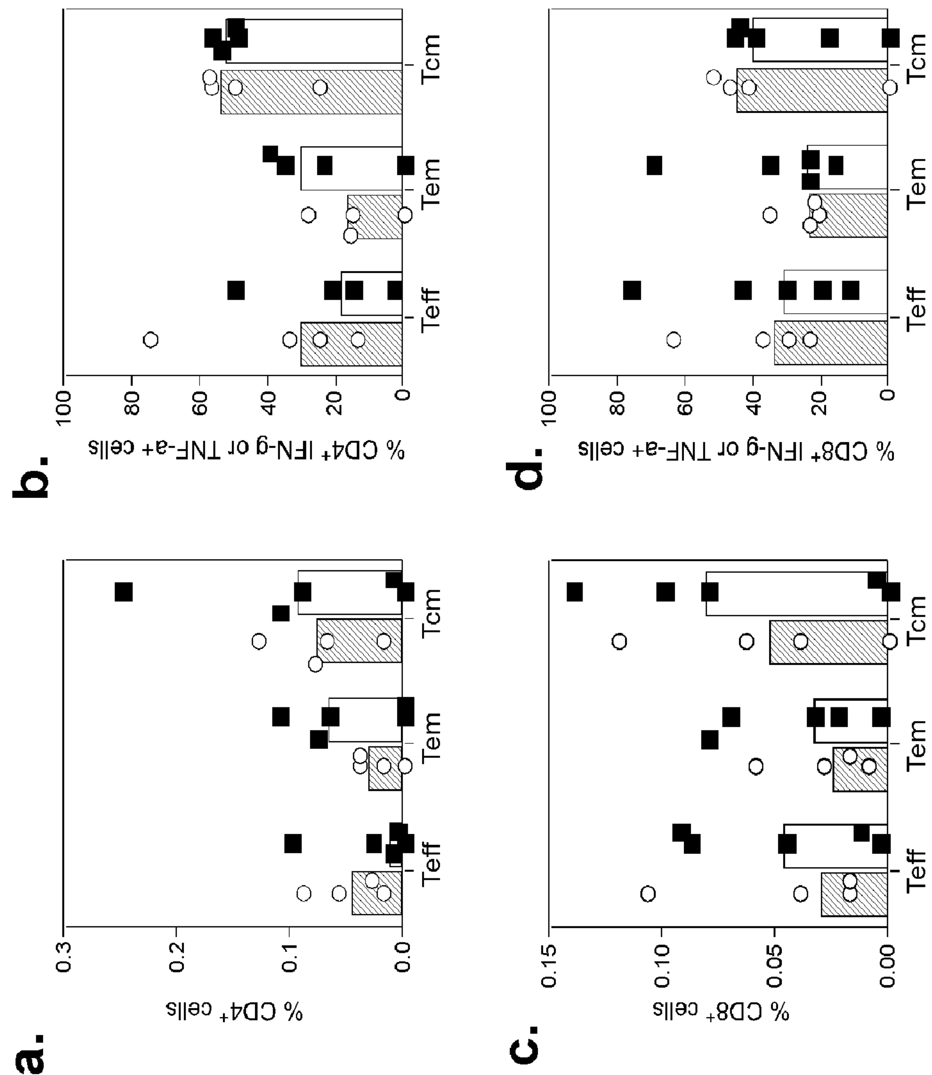

FIG. 6: Distribution of Cytokine Producing Cells into Effector and Memory Subsets.

In the same samples described in FIG. 4, cytokine producing cells (IFN-γ+ or TNF-α+ or IL-2+ cells) were further subdivided into CD45RA+, CD95− T effector cells (Teff), CD45RA+ CD95+ T effector memory cells (Tem) or CD45RA−, CD95+ T central memory cells. Graphs represent the absolute frequency of CD4+ (panel a.) or CD8+ (panel c.) Teff, Tem, Tcm or the proportion of cytokine producing CD4+ (panel b.) or CD8+ (panel d.) cells within each population. Lines represent the median per group with each animal displayed as a single point.

Figure 7:
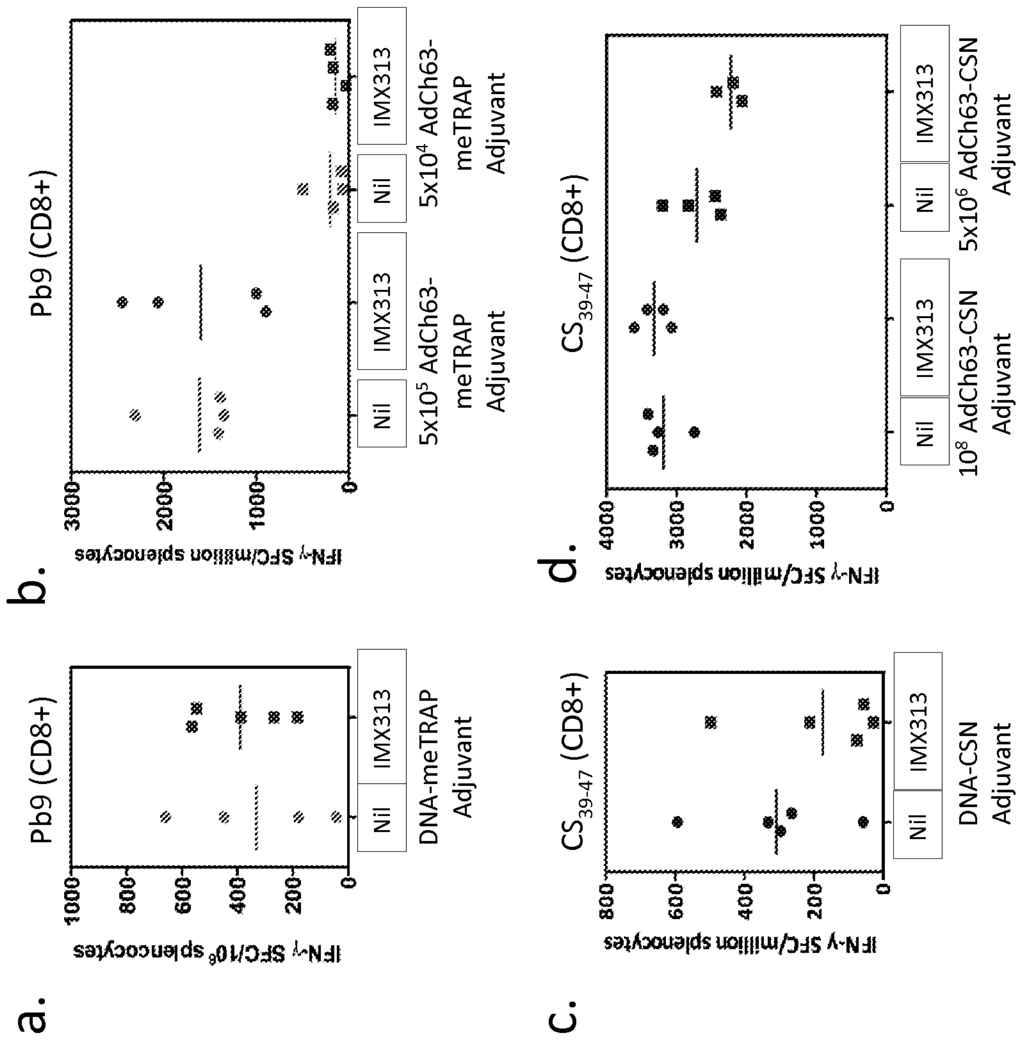

FIG. 7: IMX313 with Two Malaria Antigens

Panel a.: Balb/c mice were immunized intramuscularly on weeks 0 and 2 with 50 μg DNA-meTRAP or DNA-meTRAPIMX313 with spleen harvested 2 weeks later to determine frequency of antigen specific (Pb9) cells by IFN-γ ELISpot.

Panel b.: Balb/c mice were immunized intradermally with either AdCh63-meTRAP or AdCh63-meTRAPIMX313 at two separate doses (5×105 or 5×104 ihu). Spleen ELISpot were performed 2 weeks after immunization to determine the frequency of antigen specific IFN-γ producing cells.

Panel c.: Balb/c mice were immunized intramuscularly on weeks 0 and 2 with 50 μg DNA-CSN or DNA-CSNIMX313 with spleen harvested 2 weeks later to determine frequency of antigen specific (Pb9) cells by IFN-γ ELISpot.

Panel d.: Balb/c mice were immunized intramuscularly with either AdCh63-CSN or AdCh63-CSNIMX313 at two separate doses (108 or 5×106 ihu). Spleen ELISpot were performed 2 weeks after immunization to determine the frequency of antigen specific IFN-γ producing cells.

The invention will be further clarified by the following examples, which are intended to be purely exemplary of the invention and in no way limiting.

EXAMPLES

Example 1

Derivation of the Plasmids for Expressing the 85AIMX313 Fusion Proteins

C4bp oligomerization domains are well known in the art. The cloning, expression and purification of various C4bp oligomerization domains including murine, chicken, and human C4bp oligomerization domains is routine in the art (see for example, WO 08/122,817, EP 1795540 and WO 91/11461).

Construction of pSG2-85A313

The DNA encoding the IMX313 domain was amplified, from the plasmid pIMX313 using PCR and the following oligonucleotides:

```
oIMX1027
                                        (SEQ ID NO: 57)
5' gaagcccgacctgcaacgt ggatcc aagaagcaaggtgatgc

tgatg 3'

oIMX1028
                                        (SEQ ID NO: 58)
5' agggccctctagatgcatgctcgagcggccgcttattactccttgc

tcagtccttgc 3'
```

The 229 base pair PCR product was then inserted into the DNA vaccination vector pSG2-85A (described in Taracha et al. *Infect Immun* 71, 6904; 2003) using the site-directed mutagenesis method described by Geiser et al. (*Biotechniques* 31, 88; 2001). This replaced the nine amino acid epitope at the C-terminus of the 85A reading frame (and the TGA stop codon) by the DNA encoding the IMX313 domain (and two TAA stop codons). The entire sequence encoding the 85AIMX313 fusion protein was confirmed by DNA sequencing.

Construction of pMVA-GFP-TD-85A313

The plasmid pSG2-85A313 was partially digested with AgeI followed by complete digestion with NotI. The DNA encoding the 85AIMX313 reading frame was obtained by gel purification and then ligated into the vaccinia transfer vector pMVA-GFP-TD, which had been digested (to completion) with AgeI and NotI and dephosphorylated, before being gel purified. This results in the expression of the 85AIMX313 fusion protein from the Vaccinia P7.5 promoter after standard methods were used to transfer the plasmid insert into the TK locus in MVA. The junctions of the insert with the vector backbone and the entire 85AIMX313 open reading frame were confirmed by DNA sequencing.

Example 2

Cloning and Expression of the IMX313 Domain Fused to the Mycobacterial Antigen 85A The DNA fragment encoding the IMX313 oligomerization domain is amplified as in Example 1above, and the PCR product is digested with the restriction enzymes BamHI and NotI and cloned into the pRsetA vector from Invitrogen which is digested with the same restriction enzymes, thus creating the plasmid pRsetA313. In a second PCR, the 85A antigen is amplified from the plasmid pSG2-85A (see Example 1 above) with the following oligonucleotides:

```
85AN:
                                        (SEQ ID NO: 59)
5' GGGGCATATGTTTTCCCGGCCGGGCTTGCCGGTGG 3'
and

85AC:
                                        (SEQ ID NO: 60)
5' GGGGGGATCCGGCGCCCTGGGGCGCGGGCCCGGTGTT 3'
```

and the PCR product is digested with the restriction enzymes NdeI and BamHI and cloned into the plasmid pRsetA313, thus creating pRset85A313.

Expression.

The plasmid pRsetA85A313 is transformed into the *E. coli* strain C41(DE3). The transformed cells are grown in LB medium at 37° C. to an OD600 of approximately 0.6, then expression is induced with IPTG at a final concentration of 0.5 mM, and the culture is grown for a further four hours at 37° C. at which point the cells were harvested by centrifugation.

Purification of 85AIMX313 Protein

The protein 85AIMX313 is purified from 1 litre of C41 (DE3) cells. All of the protein is found in the soluble fraction after the cells are lysed by sonication in a buffer containing 20 mM MES pH6.5, 5 mM EDTA and a cocktail of protease inhibitors (Roche). The supernatant after centrifugation is loaded on a HitrapS column.

Cationic Column (HiTrap S)

The column is equilibrated in 20 mM MES pH 6.5, 5 mM EDTA buffer (buffer A). The protein is eluted with a gradient of 10 column volumes from Buffer A to Buffer B (buffer A plus 1M NaCl). The HiTrapS fractions containing 85AIMX313 are concentrated using a Millipore concentrator (cut-off 30 K) and then loaded on a gel filtration column, after denaturation overnight in a final volume of 10 mls in a buffer containing 50 mM Tris pH8 and 8M Urea.

First Gel Filtration Column (Superdex 200 26/60 Prep Grade) in the Presence of Urea A Superdex 200 26/60 column is equilibrated with 20 mM Tris buffer pH8, 150 mM NaCl and 8M urea, and the concentrated 85AIMX313 protein from the HiTrapS fractions is loaded. The fractions containing the 85AIMX313 are pooled, concentrated using a Millipore concentrator (cut-off 30K) and loaded onto a second Superdex 200 26/60 column, equilibrated in PBS.

Second Gel Filtration Column (Superdex 200 26/60 Prep Grade)

The concentrated 85AIMX313 protein from the first Superdex 200 26/60 column is loaded. The protein, no longer denatured, elutes as a heptamer and the fractions containing it are pooled.

Biophysical Characterisation

The oligomeric state of the 85AIMX313 protein is checked by comparing its behaviour on an SDS-PAGE gel in the presence and absence of the reducing agent beta-mercaptoethanol (BME). The 85AIMX313 protein has an apparent size of approximately 150 kDa in the absence of BME (the intra-subunit disulphide bonds have formed following exposure to air), whereas in the presence of BME, it is reduced and runs with an apparent size of just over 22 kDa (as the disulphide bonds are unable to form in the reducing environment of the bacterial cytosol).

Depending on the intended uses of the 85AIMX313 protein, the protein may be subjected to further purification steps, for example dialysis, or to concentration steps, for example freeze drying and can be administered either in PBS or formulated with adjuvants. Preferably at least two injections containing up to 100 micrograms of protein will be given subcutaneously at least two weeks apart.

Example 3

Results of Antigen-IMX313 Vaccines in Mice and Primates

Animals and Immunisations

Female Balb/c mice of 6 weeks of age or older (Harlan, UK) were used in accordance with the Home Office Animals Act Project License. Mice were immunised intramuscularly (im) into the musculus tibialis or intradermally (id) into the ear with a total volume of 50 μl of DNA or MVA diluted in PBS. For DNA immunization, mice received 50 μg of DNA per immunization and for MVA vaccinations, mice received $10^6$ plaque forming units (PFU) per immunization.

Male rhesus macaques aged between 2½ to 6 years of age received 2 immunisation with $10^8$ PFU of MVA at weeks 0 and 6 into the deltoid muscle (arms were switched between vaccinations). 15 mls of blood for PBMCs isolation and 5 mls of blood for serum were taken fortnightly from week 1 onwards. Blood samples were kept at room temperature for subsequent processing and assays.

Fusion of 85A to the IMX313 Domain Enhances CD4 and CD8 Responses in Mice

To assess the capacity of the IMX313 domain to enhance the immune response to Antigen 85A, initial screening experiments with DNA and MVA vectors were performed in mice. An increase in the response to the dominant CD4 (p15) and CD8 (p11) epitopes was observed in the blood following a single immunisation (FIG. 1*a*), which was further enhanced after a second immunisation (FIG. 1*a*). In the spleen, a small increase in the CD4 (p15) response was observed (FIG. 1*b*) and this enhancement was more apparent in the p11 specific response (CD8) where a statistically significant increase was observed (p=0.0082) (FIG. 1*b*).

Immunisation with MVA vectors displayed a similar enhancement of the response to 85A by fusion to IMX313. 1 week after intramuscular vaccination with MVA-85AIMX313, statistically significant increases in both p15 and p11 specific responses were observed in the spleen (FIG. 2*a*), a similar enhancement was also observed when mice immunised by the intradermal route (FIG. 2*b*). In agreement with the prime-boost data for DNA vaccines, the enhancement in the response to 85A observed after a single immunisation was further enhanced following a second homologous immunisation (FIG. 2*c, d*).

MVA-85AIMX313 Enhances the Immune Response in Rhesus Macaques

Following on from the significant adjuvant capacity of fusion to IMX313 observed in mice, the immune response to MVA-85A and MVA-85AIMX313 vaccines were compared in rhesus macaques. Animals were immunised intramuscularly at week 0 and week 6 with the response to Antigen 85A measured by IFN-γ ELISpot. The peak in the response to the total 85A pool or the sum of peptide pools was observed 1 weak following each vaccination (FIG. 3). When comparing the peak responses after each vaccination, a higher median 85A total pool response was observed in animals vaccinated with the MVA-85AIMX313 fusion compared to MVA-85A alone after both vaccinations (FIG. 3*c*), with the greatest fold increase observed after the second immunisation (1.86 fold prime vs 4.40 fold boost). While a similar median response to the sum of 85A peptide pools was observed at week 1, a 6.9 fold increase in the median response was observed 1 week after the second vaccination in the group of animals immunised with MVA-85AIMX313 (FIG. 3*f*). When comparing the breadth of the response to antigen 85A peptide pools, no difference between animals immunised with 85A or 85AIMX313 was seen at week 1 or week 7 (FIG. 3).

Flow cytometry analysis was used to further investigate the antigen specific response in each of these animals. 1 week after boosting these animals, a trend towards higher frequencies of IFN-γ, TNF-α and IL-2 was observed in the groups of macaques immunised with MVA-85AIMX313 (FIG. 4). On a per cell basis, animals in this same group produced higher amounts of each cytokine as measured by mean fluorescence intensity (FIG. 4).

The trend towards higher frequencies of cytokine secreting cells in animals immunised with MVA-85AIMX313 was also observed for each of the polyfunctional populations of cells producing either 1, 2 or 3 simultaneous cytokines (FIG. 5) with equal distribution of cytokine producing cells into each sub-type observed between the two groups (FIG. 5). On analysis of the effector and memory phenotype of cytokine producing cells, animals immunised with MVA-85AIMX 313 had an overall increase in the frequency of each of the T cell subtypes relative to the overall population of CD4 or CD8 cells (FIG. 5) without altering the proportion of each of these subtypes (FIG. 5). In summary, immunisation with MVA-85AIMX313 increased the overall frequency of antigen specific cells without shifting the quality of the response towards either a particular cytokine producing population or effector/memory subset. In addition, the breadth and polyfunctionality of the response observed in macaque show a striking similarity to the response observed in human volunteers immunised with MVA-85A. Based on this evidence we would predict that MVA-85AIMX313 would have similar adjuvant capacity in humans and enhance the level of the response without altering the quality.

IMX313 Does not Enhance the Immune Response to Malaria Antigens CS and meTRAP from *Plasmodium falciparum*

IMX313 was fused to two different antigens from *Plasmodium falciparum*, circumsporozoite protein (CS) and meTRAP, a multi-epitope string fused to Thrombospodin-Related Adhesion Protein (TRAP) to assess the capacity of the IMX313 domain to enhance the immune response to different antigens. Balb/c mice were immunized intramuscularly and samples were analyzed 2 weeks later. The IMX313 fusions in DNA vaccines did not display an enhancement in either the response to meTRAP (FIG. 7*a*) or CS (FIG. 7*c*). Screening in Adenovirus vaccine displayed a similar lack of IMX313 adjuvant effect; no increase in the response to meTRAP (FIG. 7*b*) or CS (FIG. 7*d*) was observed by fusion of either antigen to IMX313 at all vaccine doses tested. While a consistent enhancement in the response to Antigen 85A was observed by fusion to IMX313 (FIG. 1-6), for the two malaria antigens tested to date, no adjuvant effect of IMX313 was observed in either a DNA or Adenovirus vaccine platform.

Example 4

Construction of a Human, Simian and Chimpanzee Adenoviral Vectors Expressing the 85AIMX313 Fusion Protein The adenoviral transfer vector pENTR4-LP is described in Sridhar et al. 2008 which is incorporated herein by reference thereto (*J Virol.* 2008, volume 82, pages 3822-3833). The AgeI (partial)-NotI fragment described in Example 1 (above) encoding the 85AIMX313 fusion protein is cloned into the AgeI and NotI sites of pENTR4-LP. Using this newly obtained transfer vector, called pIMX462, the expression construct is recombined with pAd/PL-DEST to generate recombinant AdH5 adenoviruses expressing the 85AIMX313 fusion protein.

Mice are immunized as described in the cited publication and both CD4 and CD8 immune responses in these mice are measured as described in Example 3 above. Similar adenoviral vectors, derived from the human Adenoviruses 11, 26, 35, 48 and are constructed using the methods cited in the publications of Lemckert et al. 2005 (*J Virol.* 2005, volume 79, pages 9694-9701) and Abbink et al. 2007 (*J Virol.* 2007, volume 81, pages 4654-4663), both of which are incorporate herein by reference thereto, and tested as the adenoviral5 vectors are. To construct simian or chimpanzee adenoviral vectors, methods similar or identical to those published, for example by Farina et al. (*J Virol.* 2001, volume 75, pages 11603-11613), and by Roy et al. (*Hum Gene Ther.* 2004, volume 15, pages 519-530) are used. Farina et al. 2001 is incorporated herein by reference thereto.

Expression of the 85AIMX313 fusion protein in the above-described human, simian and chimpanzee vectors results in an enhanced immune response/positive immunogenicity results in both mice and primates compared to expression of 85A peptide alone.

The invention claimed is:

1. A polynucleotide sequence encoding a fusion protein comprising first and second domains, wherein the first domain of the fusion protein comprises an amino acid sequence having at least 70% sequence identity to the amino acid sequence of SEQ ID NO: 1, or a fragment of said amino acid sequence of SEQ ID NO: 1 comprising at least 20 consecutive amino acids thereof;

and wherein the second domain of the fusion protein comprises a mycobacterial antigen or an antigenic fragment thereof.

2. The polynucleotide sequence according to claim 1, wherein the second domain of the fusion protein comprises a mycobacterial antigen selected from the group consisting of 85A/Rv3804c, 85B/Rv1886c, 85C/Rv0129c, ESAT6/Rv3875, TB10.4/Rv0288, Rv0125, PPE18/Rv1196, P27/Rv1411c, HSP65/Rv0440, HBHA/Rv0475, Rv2659c, Rv2660c, HspX/Rv2031c, RPFA/Rv0867c, RPFB/Rv1009, RPFC/Rv1884c, RPFD/Rv2389c, RPFE/Rv2450c, Rv1733c, Rv2029c, Rv2032, Rv2626c, Rv2627c, Rv2628, Rv0111, Rv1806/1807, Rv0198, and Rv3812 or an antigenic fragment thereof.

3. The polynucleotide sequence according to claim 1, wherein the second domain of the fusion protein comprises an amino acid sequence having at least 70% sequence identity to an amino acid sequence selected from the group consisting of SEQ ID NOs: 3-26 and 52, or a fragment of said amino acid sequence selected from the group consisting of SEQ ID NOs: 3-26 and 52 comprising at least 10 consecutive amino acids thereof.

4. The polynucleotide sequence according to claim 1, wherein the first domain of said fusion protein comprises an amino acid sequence having at least 70% sequence identity to the amino acid sequence of SEQ ID NO: 1, or a fragment of said amino acid sequence of SEQ ID NO:1 comprising at least 20 consecutive amino acids thereof; and wherein the second domain of said fusion protein comprises an amino acid sequence having at least 70% sequence identity to an amino acid sequence selected from the group consisting of SEQ ID NOs: 3-5 and 52, or a fragment of said amino acid sequence selected from the group consisting of SEQ ID NOs: 3-5 and 52 comprising at least 10 consecutive amino acids thereof.

5. The polynucleotide sequence according to claim 1, wherein the first domain of said fusion protein is encoded by a nucleic acid sequence having at least 70% identity to a nucleic acid sequence selected from the group consisting of SEQ ID NO: 2 and SEQ ID NO: 53 or a fragment of said nucleic acid sequence selected from the group consisting of SEQ ID NO: 2 and SEQ ID NO: 53 comprising at least 60 consecutive nucleotides thereof.

6. The polynucleotide sequence according to claim 1, wherein the second domain of said fusion protein is encoded by a nucleic acid sequence having at least 70% identity to the nucleic acid sequence selected from the group consisting of SEQ ID NOs: 27-29, 51 and 56, or a fragment of said nucleic acid sequence selected from the group consisting of SEQ ID NOs: 27-29, 51 and 56 comprising at least 30 consecutive nucleotides thereof.

7. The polynucleotide sequence according to claim 1, wherein the first domain of the fusion protein is arranged C-terminal of the second domain of the fusion protein.

8. The polynucleotide sequence according to claim 1, comprising a nucleotide sequence having at least 70% identity to the nucleic acid sequence of SEQ ID NO: 54.

9. The polynucleotide sequence according to claim 1, wherein the encoded fusion protein comprises at least one additional antigen.

10. A vector comprising a polynucleotide sequence according to claim 1.

11. The vector according to claim 10, wherein the vector is selected from the group consisting of a plasmid DNA vector and a viral vector.

12. The vector according to claim 10, wherein the vector is a human adenovirus.

13. The vector according to claim 10, wherein the vector is a simian adenovirus.

14. The vector according to claim 10, wherein the vector is a chimpanzee adenovirus.

15. The vector according to claim 10, wherein the viral vector is selected from the group consisting of an adenovirus vector and a modified vaccinia Ankara virus vector.

* * * * *